(12) United States Patent
Mao et al.

(10) Patent No.: US 8,877,437 B1
(45) Date of Patent: Nov. 4, 2014

(54) METHODS OF USING DYES IN ASSOCIATION WITH NUCLEIC ACID STAINING OR DETECTION

(75) Inventors: Fei Mao, Fremont, CA (US); Wai-Yee Leung, San Ramon, CA (US); Tam Van, San Mateo, CA (US)

(73) Assignee: Biotium, Inc., Hayward, CA (US)

( * ) Notice: Subject to any disclaimer, the term of this patent is extended or adjusted under 35 U.S.C. 154(b) by 538 days.

(21) Appl. No.: 12/976,917

(22) Filed: Dec. 22, 2010

Related U.S. Application Data

(60) Provisional application No. 61/289,996, filed on Dec. 23, 2009.

(51) Int. Cl.
| | | |
|---|---|---|
| *C12Q 1/68* | (2006.01) | |
| *C12Q 1/02* | (2006.01) | |
| *C12P 19/24* | (2006.01) | |
| *C07H 21/02* | (2006.01) | |
| *C07H 21/04* | (2006.01) | |
| *C07H 19/04* | (2006.01) | |

(52) U.S. Cl.
USPC .............. 435/6.1; 435/29; 435/94; 536/23.1; 536/24.3; 536/26.6

(58) Field of Classification Search
USPC ............. 435/6.1, 29, 94; 536/23.1, 24.3, 26.6
See application file for complete search history.

(56) References Cited

U.S. PATENT DOCUMENTS

| | | |
|---|---|---|
| 4,883,867 A | 11/1989 | Lee et al. |
| 5,118,801 A | 6/1992 | Lizardi et al. |
| 5,210,015 A | 5/1993 | Gelfand et al. |
| 5,312,728 A | 5/1994 | Lizardi et al. |
| 5,321,130 A | 6/1994 | Yue et al. |
| 5,401,847 A | 3/1995 | Glazer et al. |
| 5,403,928 A | 4/1995 | Arrhenuis |
| 5,410,030 A | 4/1995 | Yue et al. |
| 5,436,134 A | 7/1995 | Haugland et al. |
| 5,445,946 A | 8/1995 | Roth et al. |
| 5,534,416 A | 7/1996 | Millard et al. |
| 5,538,848 A | 7/1996 | Livak et al. |

(Continued)

FOREIGN PATENT DOCUMENTS

| | | |
|---|---|---|
| CN | 1114359 | 1/1996 |
| EP | 1344835 A2 | 9/2003 |

(Continued)

OTHER PUBLICATIONS

Office action dated Jun. 20, 2013 for U.S. Appl. No. 13/541,313.

(Continued)

*Primary Examiner* — Jezia Riley
(74) *Attorney, Agent, or Firm* — Wilson Sonsini Goodrich & Rosati

(57) ABSTRACT

Methods of using dyes and associated technology are provided. A dye, such as a monomeric dye or a dimeric dye, may be used in a nucleic acid gel staining application and/or a nucleic acid detection application. A dimeric dye, such as a dimeric dye capable of forming a hairpin-like structure, may be used to stain and/or detect nucleic acids via a release-on-demand mechanism. A dimeric dye having low background fluorescence in the absence of nucleic acids and high fluorescence in the presence of nucleic acids, upon binding therewith, may be used to stain and/or detect nucleic acids. Buffers comprising a weak acid and a salt of the weak acid, such as a lithium salt, are also provided to allow for effective prestaining of nucleic acids.

29 Claims, 10 Drawing Sheets

(56) References Cited

U.S. PATENT DOCUMENTS

| | | | |
|---|---|---|---|
| 5,545,535 | A | 8/1996 | Roth et al. |
| 5,582,977 | A | 12/1996 | Yue et al. |
| 5,646,264 | A | 7/1997 | Glazer et al. |
| 5,656,449 | A | 8/1997 | Yue |
| 5,658,751 | A | 8/1997 | Yue et al. |
| 5,691,146 | A | 11/1997 | Mayrand |
| 5,763,162 | A | 6/1998 | Glazer et al. |
| 5,846,726 | A | 12/1998 | Nadeau et al. |
| 5,863,753 | A | 1/1999 | Haugland et al. |
| 5,925,517 | A | 7/1999 | Tyagi et al. |
| 5,977,344 | A | 11/1999 | Glazer et al. |
| 6,037,137 | A | 3/2000 | Komoriya et al. |
| 6,150,097 | A | 11/2000 | Tyagi et al. |
| 6,258,569 | B1 | 7/2001 | Livak et al. |
| 6,277,570 | B1 | 8/2001 | Wood et al. |
| 6,569,627 | B2 | 5/2003 | Wittwer et al. |
| 6,635,427 | B2 | 10/2003 | Wittwer et al. |
| 6,664,047 | B1 | 12/2003 | Haugland et al. |
| 7,166,478 | B2 | 1/2007 | Stavrianopoulos et al. |
| 7,387,887 | B2 | 6/2008 | Wittwer et al. |
| 7,601,498 | B2 | 10/2009 | Mao et al. |
| 7,776,567 | B2 | 8/2010 | Mao et al. |
| 7,803,943 | B2 | 9/2010 | Mao et al. |
| 8,530,195 | B2 | 9/2013 | Mao et al. |
| 2003/0008316 | A1 | 1/2003 | Smith et al. |
| 2003/0092062 | A1 | 5/2003 | Reddy et al. |
| 2004/0132046 | A1 | 7/2004 | Westman et al. |
| 2005/0239096 | A1 | 10/2005 | Beaudet et al. |
| 2010/0317016 | A1 | 12/2010 | Mao et al. |
| 2010/0323453 | A1 | 12/2010 | Mao et al. |
| 2013/0167309 | A1 | 7/2013 | Mao et al. |
| 2014/0073058 | A1 | 3/2014 | Mao et al. |
| 2014/0106349 | A1 | 4/2014 | Mao et al. |

FOREIGN PATENT DOCUMENTS

| | | |
|---|---|---|
| EP | 1348713 A2 | 10/2003 |
| EP | 1373250 B1 | 8/2006 |
| JP | 2002327130 | 11/2002 |
| WO | WO 2004/038038 A2 | 5/2004 |
| WO | WO 2006/020947 A2 | 2/2006 |
| WO | WO 2006/020947 A3 | 8/2008 |

OTHER PUBLICATIONS

European search report and search opinion dated Feb. 14, 2012 for Application No. 11175090.7.

U.S. Appl. No. 12/976,917, filed Dec. 22, 2010, Mao et al.

"Lab Ref: A Handbook of Recipes, Reagents, and Other Reference Tools for Use at the Bench," Electrophoresis of DNA, RNA, and Protein, Section 3A, 2002, pp. 62-80.

"Nucleic Acid Stains and Products for Genomics Studies," www.biotium.com-Fluorescent Probes and Related Biochemical Reagents for Life Science, Section 9, 2005-2006, pp. 161-173.

Adkins, et al. Visualization of DNA in Agarose Gels as Migrating Colored Bands: Applications for Preparative Gels and Educational Demonstrations. Analytical Biochemistry, vol. 240, Article No. 0325, 1996, pp. 17-23.

Albert, A. The Acridines. Their Preparation, Physical, Chemical, and Biological Properties, and Uses. Angew. Chem. internat. Edi, vol. 6, No. 10, 1967, 1 page.

Atwell, et al. Potential antitumor agents. 45. Synthesis, DNA-binding interaction, and biological activity of triacridine derivatives. J Med Chem. Jan. 1986;29(1):69-74.

Barak, et al. Fluorescent Low Density Lipoprotein for Observation of Dynamics of Individual Receptor Complexes on Cultured Human Fibroblasts, The Journal of Cell Biology, vol. 90, 1981, pp. 595-604.

Bengtsson, et al.,A New Minor Groove Binding Asymmetric Cyanine Reporter Dye for Real-Time PCR. Nucleic Acid Research, vol. 31, No. 8, 2003, pp. 1-5.

Benson, et al. Heterodimeric DNA-Binding Dyes Designed for Energy Transfer: Synthesis and Spectroscopic Properties. Nucleic Acids Research, vol. 21, No. 24, 1993, pp. 5727-5735.

Capelle, et al. Deoxyribonucleic Acid Bifunctional Intercalators: Kinetic Investigation of the Binding of Several Acridine Dimers to Deoxyribonucleic Acid. Biochemistry, vol. 18, No. 15, 1979, pp. 3354-3362.

Carreon, et al. Thiazole Orange-Peptide Conjugates: Sensitivity of DNA Binding to Chemical Structure. Organic Letters, vol. 6, No. 4, 2004, pp. 517-519.

Chakraborty, et al. Synthesis and DNA Binding Properties of Pyrrole Amino Acid-Containing Peptides. Tetrahedron Letters, vol. 46, 2005, pp. 647-651.

Dervan. Molecular Recognition of DNA by Small Molecules. Bioorganic & Medicinal Chemistry, vol. 9, 2001, pp. 2215-2235.

Eldho, et al. One Pot Synthesis of a Acridinylalkanoic Acids and Novel Bisacridines. Synthetic Communications, 29(22), 1999, pp. 4007-4014.

Fukunaga, et al. Production of Frameshift Mutations in Salmonella by Phenanthridinium Derivatives: Enzymatic Activation and Photoaffinity Labeling. Mutation Research, vol. 127, 1984, pp. 31-37.

Gaugain, et al. DNA Bifunctional Intercalators. 1. Synthesis and Conformational Properties of an Ethidium Homodimer and of an Acridine Ethidium Heterodimer. Biochemistry, vol. 17, No. 24, Nov. 28, 1978, pp. 5071-5078.

Gaugain, et al. DNA Bifunctional Intercalators. 2. Fluorescence Properties and DNA Binding Interaction of an Ethidium Homodimer and an Acridine Ethidium Heterodimer. Biochemistry, vol. 17, No. 24, 1978, pp. 5078-5088.

Gerlach, et al. Armalen Dr Physik, G Folge, Band 2, 1948, pp. 55-75.

Gong, et al., New DNA Minor-Groove Binding Molecules with High Sequence-Selectivities and Binding Affinities, Biochemical and Biophysical Communications, vol. 240, No. 3, 1997, pp. 557-560.

Guo, et al. DNA-Dye Fluorescence Enhancement Based on Shifting the Dimer-Monomer Equilibrium of Fluorescent Dye, Applied Spectroscopy, vol. 51, No. 7, 1997, pp. 1002-1007.

Hartwig, et al. Room-Temperature Palladium-Catalyzed Amination of Aryl Bromides and Chlorides and Extended Scope of Aromatic C-N Bond Formation with a Commercial Ligand. J. Org. Chem., vol. 64, 1999, pp. 5575-5580.

Haugland. Handbook of Fluorescent Probes and Research Products—Ninth Edition: Nucleic Acid Detection and Genomics Technology. Molecular Probes, Chapter 8, 2002, pp. 265-352.

Higuchi, et al. Simultaneous Amplification and Detection of Specific DNA Sequences. Bio/Technology, vol. 10, Apr. 1992, pp. 413-417.

Holland, et al. Detection of Specific Polymerase Chain Reaction Product by Utilizing the 5' →3' Exonuclease Activity of Thermus Aquaticus DNA Polymerase. Proc. Natl. Acad. Sci. USA, vol. 88, Aug. 1991, pp. 7276-7280.

Ishiguro, et al. Fluorescence Detection of Specific Sequence of Nucleic Acids by Oxazole Yellow-Linked Oligonucleotides. Homogeneous Quantitative Monitoring of in vitro Transcription. Nucleic Acids Research; vol. 24, No. 24, 1996, pp. 4992-4997.

Jackobsen, et al. Site selective bis-intercalation of a homodimeric thiazole orange dye in DNA oligonucleotides. Nucleic Acids Res. 1995; 23(5):753-60.

Joseph, et al. Tuning of Intercalation and Electron-Transfer Processes Between DNA and Acridinium Derivatives through Steric Effects. Bioconjugate Chem., vol. 15, 2004, pp. 1230-1235.

Kapuscinski, et al. Fluorescent Complexes of DNA with DAPI 4',6-diamidine-2- phenyl indole.2HCI or DCI 4',6-dicarboxyamide-2-phenyl indole. Nucleic Acid Research, vol. 5, No. 10, Oct. 1978, pp. 3775-3799.

Karsai, et al. Evaluation of a Homemade SYBR Green I Reaction Mixture for Real-Time PCR Quantification of Gene Expression. Biotechniques, Apr. 2002; 32(4): 790-2, 794-6.

Khairutdinov, et al. Photophysics of Cyanine Dyes: Subnanosecond Relaxation Dynamics in Monomers, Dimers, and H- and J-Aggregates in Solution. J. Phys. Chem. B, vol. 101, No. 14, 1997, pp. 2602-2610.

Latt, et al. Spectral Studies on 33258 HOECHST and Related Bisbenzimidazole Dyes Useful for Fluorescent Detection of Deoxyribonucleic Acid Synthesis. The Journal of Histochemistry and Cytochemistry, vol. 24, No. 1, 1976, pp. 24-33.

(56) References Cited

OTHER PUBLICATIONS

Lee, et al. Allelic Discrimination by Nick-Translation PCR with Fluorogenic Probes. Nucleic Acids Research, vol. 21, No. 16, 1993, pp. 3761-3766.
Lown, et al. Efficient Total Syntheses of the Oligopeptide Antibiotics Netropsin and Distamycin. J. Org. Chem., vol. 50, No. 20, 1985, pp. 3774-3779.
McCann, et al. Detection of Carcinogens as Mutagens in the Salmonella/Microsome Test: Assay of 300 Chemicals. Proc. Nat. Acad. Sci. USA, No. 12, Dec. 1975, pp. 5135-5139.
Nath, et al., "Effects of Ethidium Bromide and SYBR Green I on Different Polymerase Chain Reaction Systems," Journal of Biochemical and Biophysical Methods, vol. 42, 2000, pp. 15-29.
Notification of transmittal of the international search report and the written opinion of the international searching authority, International Application No. PCT/US06/09910, mailed Mar. 29, 2007, 6 pages.
Otto, et al. A Comparative Study of DAPI, DIPI, and HOECHST 33258 and 33342 As Chromosomal DNA Stains, Stain Technology, vol. 60, No. 1, 1985, pp. 7-11.
Parks, et al. Optimization of the Hairpin Polyamide Design for Recognition of the Minor Groove of DNA. J. Am. Chem. Soc., vol. 118, No. 26, 1996, pp. 6147-6152.
Perera. PCR Based Detection of Mycobacterium Tuberculosis: Effect of Sample Preparation. Southeast Asian J. Trop. Med Public Health, vol. 25, No. 4, Dec. 1994, pp. 693-697.
Rohatgi, et al. Thermodynamics of Dye Dimerization. Chemical Physics Letters, vol. 12, No. 2, Dec. 15, 1971, pp. 259-260.
Rohatgi,et al. Nature of Bonding in Dye Aggregates. The Journal of Physical Chemistry, vol. 70, No. 6, Jun. 1966, pp. 1695-1701.
Rye, et al. Stable fluorescent complexes of double-stranded DNA with bis-intercalating asymmetric cyanine dyes: properties and applications. Nucleic Acids Res. 1992; 20(11):2803-12.
Saiki, et al. Enzymatic Amplification of β-Globin Genomic Sequences and Restriction Site Analysis for Diagnosis of Sickle Cell Anemia. Science, vol. 230, Dec. 20, 1985, pp. 1350-1354.
Septinus, et al. Hydrophobic Acridine Dyes for Fluorescence Staining of Mitocondria in Living Cells: 1. Thermodynamic and Spectroscopic Properties of 10-n-Alkyl-Acridinium-Orange-Chlorides, Histochemistry, vol. 79, 1983, pp. 443-456.
Stryer, et al. Energy Transfer: A Spectroscopic Ruler. Proceedings of the National Academy of Sciences of the United States of America, vol. 58, No. 2, Aug. 15, 1967, pp. 719-726.
Sumner. Chromosome Banding and Identification. Methods in Molecular Biology: Chromosome Analysis Protocols, vol. 29, 1994, pp. 83-96.
Traganos, et al. Simultaneous Staining of Ribonucleic and Deoxyribonucleic Acids in Unfixed Cells Using Acridine Orange in a Flow Cytofluorometric System. www.jhc.org/cgi/content/abstract/25/1/46, 1 page. Accessed Mar. 2, 2005.
Tse, et al. A Fluorescent Intercalator Displacement Assay for Establishing DNA Binding Selectivity and Affinity. Accounts of Chemical Research, vol. 37, No. 1, 2004, pp. 61-69.
Ueda, et al. Single-Molecule Analysis of Chemotactic Signaling in Dictyostelium Cells. Science, vol. 294, Oct. 26, 2001, pp. 864-867.
Waring. Complex Formation Between Ethidium Bromide and Nucleic Acids. J. Mol. Biol., vol. 13, 1965, pp. 269-282.
West, et al. The Dimeric State of Cyanine Dyes. The Journal of Physical Chemistry, vol. 69, No. 6, Jun. 1965, pp. 1894-1903.
Wirth, et al. Interactions between DNA and mono-, bis-, tris-, tetrakis-, and hexakis(aminoacridines). A linear and circular dichroism, electric orientation relaxation, viscometry, and equilibrium study. J. Am. Chem. Soc. 1988; 110 (3):932-939.
Wittwer, et al. Continuous Fluorescence Monitoring of Rapid Cycle DNA Amplification. BioTechniques, vol. 22, No. 1, Jan. 1997, pp. 130-138.
Wolfe, et al. Simple, Efficient Catalyst System for the Palladium-Catalyzed Amination of Aryl Chlorides, Bromides, and Triflates, J. Org. Chem., vol. 65, 2000, pp. 1158-1174.
Yamagishi et al. Activation of Reactant Molecules by Reversed Micelles. J. Phys. Chem., vol. 85, No. 3, 1981, pp. 281-285.
Yang, et al. Palladium-Catalyzed Amination of Aryl Halides and Sulfonates, Journal of Organometallic Chemistry, vol. 576, 1999, pp. 125-146.
Yarmoluk, et al. Interaction of cyanine dyes with nucleic acids—XXVII: synthesis and spectral properties of novel homodi- and homotrimeric monomethine cyanine dyes . Dyes and Pigments. 2001; 50:21-28.
Yunjing, et al. Study on Acridine Orange Dimer as a New Fluorescnet Probe for the Determination of Protein. Anal. Commun., vol. 36, 1999, pp. 135-137.
Zimmerman, et al. Topologically constrained bifunctional intercalators: DNA intercalation by a macrocyclic biscridine. J. Am. Chem. Soc. 1989; 111 (17):6805-6809.
Zipper, et al. Investigations on DNA Intercalation and Surface Binding by SYBR Green 1, Its Structure Determination and Methodological Implications. Nucleic Acid Research, vol. 32, No. 12, 2004, pp. 1-10.
Office action dated Feb. 23, 2012 for U.S. Appl. No. 12/820,983.
Office action dated Jul. 11, 2008 for U.S. Appl. No. 11/377,254.
Office action dated Aug. 9, 2011 for U.S. Appl. No. 12/854,436.
Office action dated Sep. 14, 2012 for U.S. Appl. No. 12/820,983.
Office action dated Sep. 29, 2009 for U.S. Appl. No. 11/377,253.
U.S. Appl. No. 13/541,313, filed Jul. 3, 2012, Mao et al.
Office action dated Aug. 28, 2014 for U.S. Appl. No. 13/962,668.

A.

B.

A. SYBR Green Emission Filter

B. EtBr Emission Filter

METHODS OF USING DYES IN ASSOCIATION WITH NUCLEIC ACID STAINING OR DETECTION

CROSS-REFERENCE TO RELATED APPLICATIONS

This application claims benefit under 35 U.S.C. §119(e) to U.S. Provisional Application No. 61/289,996 filed on Dec. 23, 2009, which is hereby incorporated by reference in its entirety.

BACKGROUND

Fluorescent dyes or stains can be used in the detection of nucleic acids, such as DNA, RNA, DNA/RNA hybrid molecules, and biological samples containing the same. Nucleic acid polymers, such as DNA and RNA hold the genetic information that is transmitted from one generation to the next. These molecules are also responsible for maintaining routine function of a living organism. Nucleic acids are thus of interest and the objects of study. Fluorescent nucleic acid dyes that specifically bind to nucleic acids and form highly fluorescent complexes are useful tools for such study. These dyes can be used to detect the presence and quantities of DNA and RNA in a variety of media, including pure solutions, cell extracts, electrophoretic gels, micro-array chips, live or fixed cells, dead cells, and environmental samples.

Nucleic acid staining is generally performed using one of the three major methods: 1) prestaining; 2) in-gel or precast staining; and 3) post staining. In the pre-staining method, a nucleic acid binding dye is pre-mixed with a nucleic acid sample to form DNA- or RNA-dye complexes in a loading buffer. The resulting solution is then loaded into a well in a gel for gel electrophoresis. During electrophoresis, the DNA- or RNA-dye complexes migrate through the gel matrix and separate into bands according to their molecular sizes. In the in-gel staining method, the dye is embedded throughout the gel matrix by adding the dye to the gel-forming material (e.g., agarose powder and buffer) when the gel is poured. During gel electrophoresis, the migrating nucleic acids encounter the dye in the gel matrix to form fluorescent nucleic acid-dye complexes. In post staining method, a nucleic acid sample is first separated by gel electrophoresis. The gel containing the separated bands is then immersed in a solution containing the nucleic acid dye to allow the formation of nucleic acid-dye complex. Depending on the dye used, a washing or de-staining step may be necessary for some of the dyes in order to remove the background.

There are advantages and disadvantages associated with each of the methods. The prestaining method is generally more desirable because it requires less dye molecules and thus minimizes the chance for a handler to exposure to potentially toxic dye molecules. It also offers flexibility by permitting any unused wells in the gel to be used again later. Furthermore, it saves time by eliminating an extra staining step. However, most nucleic acid dyes when used in conventional buffer systems are not suitable for this method, either because the dyes do not have sufficient binding affinity to accompany the nucleic acid molecules during migration, or because the binding is too tight which causes retardation of nucleic acid migration. Most nucleic acid dyes are positively charged and thus they tend to migrate in the opposite direction, which makes detection of the faster-moving small nucleic acid molecules insensitive. Even for dyes that have been used for the prestaining method, the aforementioned problems still exist to a certain degree, not to mention safety issues. In theory, in-gel staining is the next best choice because no extra staining step is required. However, poor band resolution caused by dye interference to nucleic acid dye migration often limits its utility. Like prestaining, dye migrating to the opposite direction can also be a problem. Post gel staining requires an extra staining step, which is a disadvantage, especially if the dye is toxic. However, post staining also has a major advantage in that nucleic acid migration is never interfered by the dye, thus it often can result in good gel resolution even when conventional buffers are used.

A variety of nucleic acid stains have been used for detecting nucleic acids in gels. The classic and still the most widely used nucleic acid gel stain is ethidium bromide (EB). The dye is inexpensive and offers sufficient sensitivity for most applications. A major problem associated with EB, however, is its toxicity. EB is known to be a powerful mutagen. As a result, special handling and disposal are required for the dye, making the dye ultimately more expensive to use.

In recognition of the problem, alternative dyes to EB have been developed in recent years. These dyes include SYBR Green I and SYBR Safe (US patent Application No. 2005/0239096) from Invitrogen, Co. and GelRed and GelGreen (U.S. Pat. No. 7,601,498) from Biotium, Inc. These gel stains have been shown to be either weakly mutagenic or completely nonmutagenic by standard Ames test. Moreover, SYBR Safe, GelRed and GelGreen have also been tested to be safe to aquatic life, making the dyes easy to dispose. However, although SYBR Green I and SYBR Safe have improved mutagenic safety profile, they are still cytotoxic at relatively high concentrations due to their relatively small molecular sizes, which facilitate their rapid entry into cells (Briggs C and Jones M, Acta Histochem. 107(4), 301(2005)).

GelRed and GelGreen belong to a new class of dimeric nucleic acid dyes with a flexible neutral linker (U.S. Pat. No. 7,601,498). On average, these dimeric dyes have a molecular weight at least 2-3 times that of SYBR Safe or SYBR Green I and bear two positive charges as opposed to only one positive charge for SYBR Safe, for example. The much larger sizes as well as the higher charge of GelRed and GelGreen render them difficult to cross the cell membranes, thus denying the opportunity for the dyes to interfere with any intracellular activities, including activities associated with genomic DNA. Consequently, GelRed and GelGreen are not only non-mutagenic but also noncytotoxic within the dye concentration range normally used for nucleic acid gel staining. Furthermore, dimeric dyes such as GelRed and GelGreen exhibit exceptional signal-to-noise ratio because the dyes self-quench in the absence of nucleic acids to result in very low background fluorescence. The improved safety and sensitivity of GelRed and GelGreen make them some of best nucleic acid gel stains.

SUMMARY OF THE INVENTION

The present invention discloses pre-staining method that produces well resolved bands and is sensitive and minimally affected by the nature of nucleic acid samples. In one embodiment, the present invention provides a method of detecting the presence or absence of a nucleic acid in a sample, comprising:

(a) combining a sample comprising a nucleic acid with at least one fluorescent nucleic acid binding dye having the formula:

wherein BRIDGE is a substantially neutral covalent linker comprising from about 1 to about 150 non-hydrogen atoms;
$Q_1$ is a phenanthridinium dye, an acridinium dye or an asymmetric cyanine dye;
$Q_2$ is a phenanthridinium dye, an acridinium dye or an asymmetric cyanine dye;
(b) loading said sample into a gel, wherein said gel comprising a gel buffer, said gel buffer comprising at least one weak acid and a salt of said at least one weak acid;
(c) electrophoresing said sample; and
(d) detecting fluorescence associated with the sample or a lack thereof In a related embodiment, the steps involve:
(a) combining a nucleic acid sample with a loading buffer comprising at least one nucleic acid binding dye and optionally at least one loading dye, wherein the at least one nucleic acid binding dye has the formula of:

wherein BRIDGE is a substantially neutral covalent linker comprising from about 1 to about 150 non-hydrogen atoms; $Q_1$ and $Q_2$ are each independently selected from the groups consisting of a phenanthridinium dye, an acridinium dye and an asymmetric cyanine dye;
(b) loading a volume of the said loading buffer into an electrophoresis gel comprising a gel buffer, wherein the gel may optionally be bathed in a running buffer, wherein the gel buffer and running buffer each independently comprises at least one weak acid and the lithium salt of said at least one weak acid and wherein the $pK_a$ of said at least one weak acid is from about 8 to about 10.5;
(c) applying a voltage across the gel to effect electrophoresis;
(d) illuminating the gel with a light to cause the excitation of the nucleic acid bound-dye and;
(e) detecting the fluorescence of the dye either during the process of the gel electrophoresis or following the completion of the gel electrophoresis.

In various embodiments, the method further comprises a loading dye, including but not limited to xylene cyanol, cresol red, bromophenol blue, orange G and tartrazine.

The dye used in the subject method may be a dimeric dye disclosed herein, wherein $Q_1$ and $Q_2$ are different or the same. Where desired, both $Q_1$ and $Q_2$ are the same phenanthridinium dye. In one embodiment, when $Q_1$ and/or $Q_2$ is a phenanthridinium dye it has the structure of Formula I or Formula II:

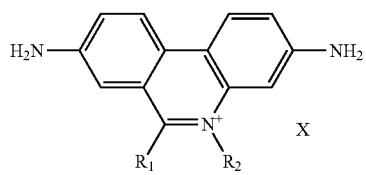

Formula I

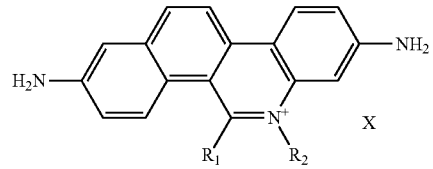

Formula II wherein $R_1$ is an aryl, a heteroaryl, an alkyl, H, -BRIDGE-$Q_1$ or -BRIDGE-$Q_2$; $R_2$ is an alkyl, -BRIDGE-$Q_1$ or -BRIDGE-$Q_2$; X is a counter ion and wherein only one of $R_1$ and $R_2$ is -BRIDGE-$Q_1$ or -BRIDGE-$Q_2$.

The phenanthridinium dye can adopt the structure of Formula I, wherein $R_1$ is a phenyl and $R_2$ is -BRIDGE-$Q_1$ or -BRIDGE-$Q_2$.

In a separate embodiment, $Q_1$ and/or $Q_2$ is a acridinium dye and it has the structure of Formula III:

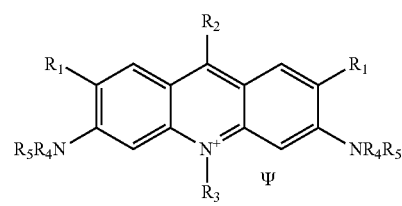

Formula III wherein each $R_1$, may be the same or different and is H, or a C1-C2 alkyl; $R_2$ is an H, a C1-C6 alkyl, a C1-C2 perfluoroalkyl, an aryl, an heteroaryl, —$NH_2$, —$NHCH_3$, —CN, —C(=O)$NH_2$, -BRIDGE-$Q_1$ or -BRIDGE-$Q_2$; $R_3$ is an H, a C1-C2 alkyl, -BRIDGE-$Q_1$ and -BRIDGE-$Q_2$; $R_4$ and $R_5$, may be the same or different and is an H, or a C1-C2 alkyl; and Ψ is a counter ion; and only one of $R_2$ and $R_3$ is -BRIDGE-$Q_1$ or -BRIDGE-$Q_2$.

The method of claim 12, wherein $R_1$ and $R_2$ are H; $R_3$ is -BRIDGE-$Q_1$ or -BRIDGE-$Q_2$; and $R_4$ and $R_5$ are —$CH_3$.

Where desired, both $Q_1$ and $Q_2$ are the same acridinium dye.

In yet another embodiment, $Q_1$ and/or $Q_2$ is a asymmetric cyanine dye and it has the structure of Formula IV:

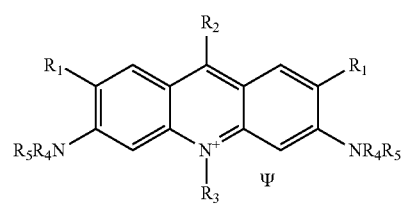

Formula IV wherein $R_1$ is a substituted or unsubstituted C1-C6 alkyl; $R_2$ is H, halogen or a substituted or unsubstituted aryl; n is 0, 1 or 2; $R_3$ is an H, a substituted or unsubstituted alkyl, a substituted or unsubstituted alkylamino, a substituted or unsubstituted dialkylamino, dialkylamino, a substituted or unsubstituted aryl, a substituted or unsubstituted heterocycle, -BRIDGE-$Q_1$ or -BRIDGE-$Q_2$; $R_4$ is a substituted or unsubstituted C1-C6 alkyl, a substituted or unsubstituted aryl, -BRIDGE-$Q_1$ and -BRIDGE-$Q_2$; $R_5$ and $R_6$ may be the same or different and are H, or —$CH_3$ or $R_5$ and $R_6$ in combination with the carbon atoms they are attached to form a fused benzene ring; $\Psi$ is a counter ion; and only one of $R_3$ and $R_4$ is -BRIDGE-$Q_1$ or -BRIDGE-$Q_2$.

In some instances, $R_1$ is —$CH_3$; $R_2$ is H; n is 0; $R_3$ is H; $R_4$ is -BRIDGE-$Q_1$ or -BRIDGE-$Q_2$; and $R_5$ and $R_6$ together with the carbon atoms they are attached to form a fused benzene ring.

In other instances, $Q_1$ and $Q_2$ can be the same asymmetric cyanine dye.

In practicing the subject method, the weak acid utilized can have a $pK_a$ of about 8.0 to about 10.5. An exemplary weak acid is boric acid. Where desired, the gel buffer has a pH of about 7.7 to about 9.0, or from about 8 to about 8.8.

One exemplary gel buffer comprises from about 0.5 mM to about 30 mM $Li^+$. Where desired, the gel buffer further comprises one or more of a magnesium chelator, a detergent, or a preservative.

The present invention further provides a composition comprising:

a fluorescent nucleic acid binding dye having the formula:

wherein BRIDGE is a substantially neutral covalent linker comprising from about 1 to about 150 non-hydrogen atoms;

$Q_1$ is a phenanthridinium dye, an acridinium dye or an asymmetric cyanine dye;

$Q_2$ is a phenanthridinium dye, an acridinium dye or an asymmetric cyanine dye;

and a buffer comprising at least one weak acid and a salt of said at least one weak acid.

Any of the dimeric dyes disclosed herein can be part of the composition.

The present invention also provides a kit comprising a gel electrophoresis buffer according to the invention, a loading buffer comprising a dimeric nucleic acid-binding dye according to the invention, and an instruction manual. Optionally, the loading buffer in the above kit further comprises at least one loading dye. The gel electrophoresis buffer in the kit is preferably at least 20× concentrated or more preferably at least 25× concentrated. Even more preferably, the gel electrophoresis buffer in the kit is provided as a lyophilized solid. Preferably, the loading buffer in kit is provided as an at least 6× concentrated solution. The kit may further optionally comprise agarose powder. Alternatively, the kit further provides precast gels comprising the buffer according to the invention. The kit may optionally further comprise a nucleic acid ladder.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A detailed description of various aspects, features and embodiments is provided herein with reference to the accompanying drawings, which are briefly described below. The drawings are illustrative and are not necessarily drawn to scale. The drawings illustrate various aspects or features and may illustrate one or more embodiment(s) or example(s) in whole or in part. A reference numeral, letter, and/or symbol that is used in one drawing to refer to a particular element or feature may be used in another drawing to refer to a like element or feature.

OmniPur (EMD) (B) gels were run in 1× sodium borate running buffer. No dye was added to the gels. Compound A was added to each DNA sample to a final concentration of 1 uM (1×) or 2 uM (2×) prior to loading onto the gels. The DNA samples for the two gels are the same and are in the same order. The samples in the lanes in (A) 1× is as followed (from left to right): (1) GeneRuler 1 kB ladder, (2) Invitrogen 1 kB ladder, (3) Promega Lambda DNA-HindIII digest, (4) Bioline HyperLadder I, (5) Bioline HyperLadder IV, (6) Axygen M-DNA-LR, and (7) Axygen M-DNA-BR. (A) 2× contains the same DNA samples and in the same loading order from left to right as (A) 1×. (B) contains the same DNA samples, loaded in the same order as (A).

Figure 6:
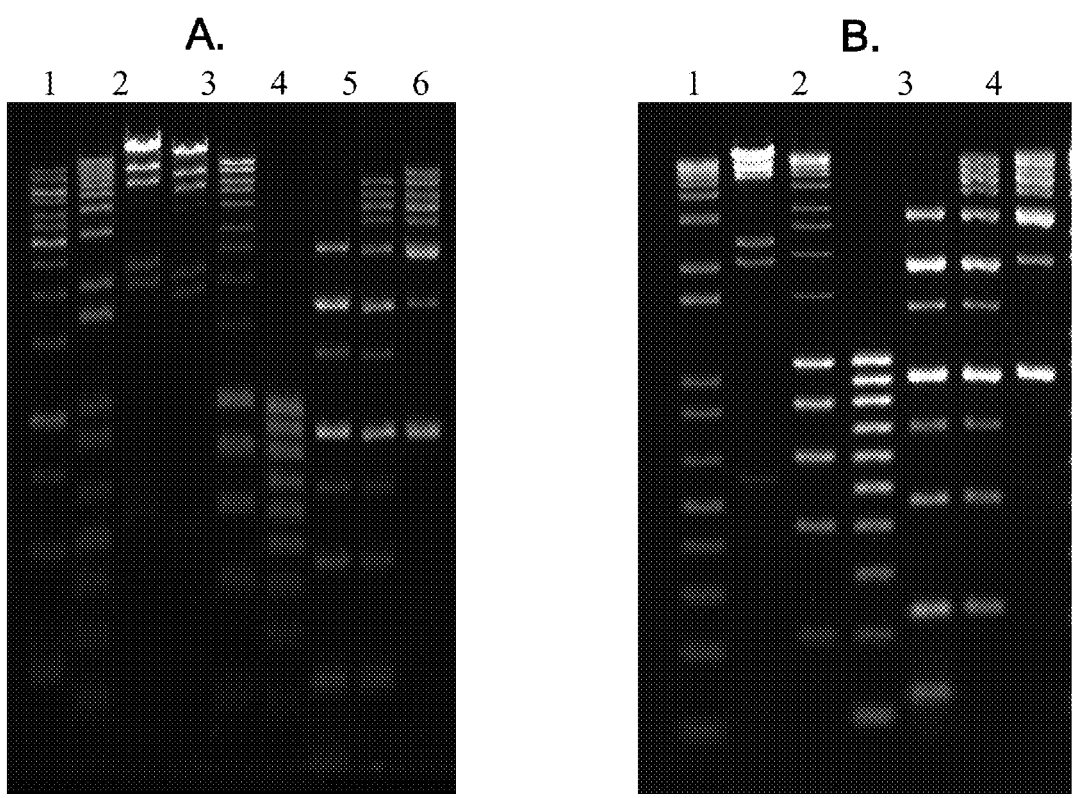

FIG. 6 (FIG. 6) illustrates pre-staining with Compound A (Table 1) in Lithium Borate. Two different agarose gels were used to test pre-staining condition with lithium borate running buffer. 0.7% OmniPur (EMD) (A) and AquaPor 3:1 (National Diagnostics) (B) agarose were run in 1× lithium borate running buffer. No nucleic acid dye was added to the gel. Compound A was pre-mix with each DNA samples to a concentration of 1 uM before loading onto the gels. Samples in the lanes for (A) are as followed (from left to right): (1) GeneRuler 1 kB ladder, (2) Invitrogen 1 kB ladder, (3) New England BioLabs Lambda DNA-HindIII digest, (4) Promega Lambda DNA-HindIII digest, (5) Bioline HyperLadder I, (6) Bioline HyperLadder IV, (7) Axygen M-DNA-LR, (8) Axygen M-DNA-BR, and (9) Axygen M-DNA-HR. For (B): (1) Invitrogen 1 kB ladder, (2) New England BioLabs Lambda DNA-HindIII digest, (3) Bioline HyperLadder I, (4) Bioline HyperLadder IV, (5) Axygen M-DNA-LR, (6) Axygen M-DNA-BR, and (7) Axygen M-DNA-HR.

Figure 7:
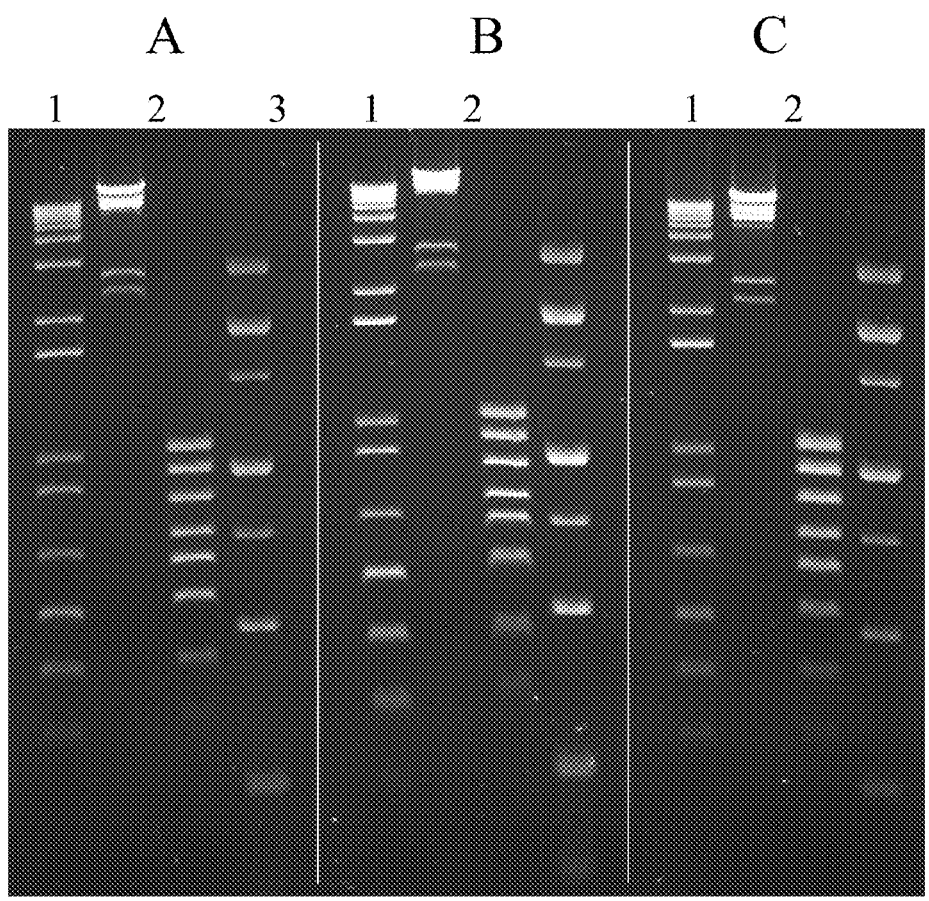

FIG. 7 (FIG. 7) illustrates pre-staining with Compounds D and F (Table 1) in Lithium Borate. Pre-staining with 2.5 uM Compound No. 4 (A), 5 uM Compound D (B), and 1 uM Compound F (C). 1% Agarose gel was run in 1× lithium borate buffer. Samples were loaded as follows (from left to right): (1) Invitrogen 1 kB ladder, (2) Promega Lambda DNA-HindIII digest, (3) Bioline HyperLadder IV, (4) Axygen M-DNA-LR, (5) BLANK, (6) Invitrogen 1 kB ladder, (7) Promega Lambda DNA-HindIII digest, (8) Bioline Hyper-Ladder IV, (9) Axygen M-DNA-LR, (10) BLANK, (11) Invitrogen 1 kB ladder, (12) Promega Lambda DNA-HindIII digest, (13) Bioline HyperLadder IV, and (14) Axygen M-DNA-LR. Gel was visualized on the UVP GelDoc-It Imaging System using the SYBR Green emission filter setting. Picture is from a 2 second exposure.

Figure 8:
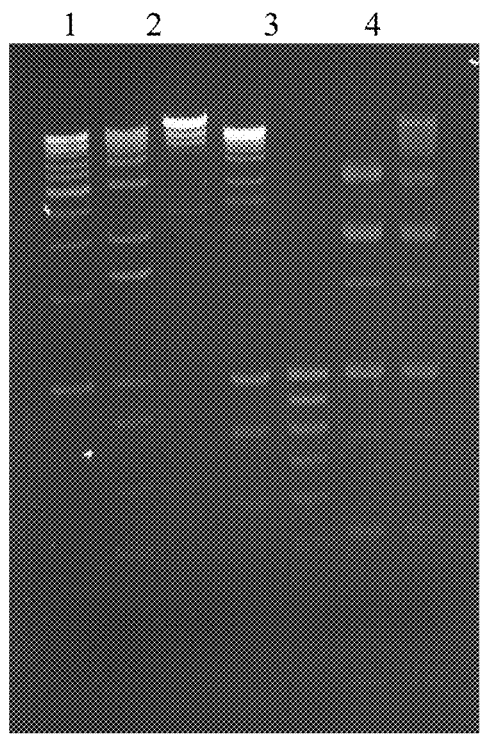
Figure 8:
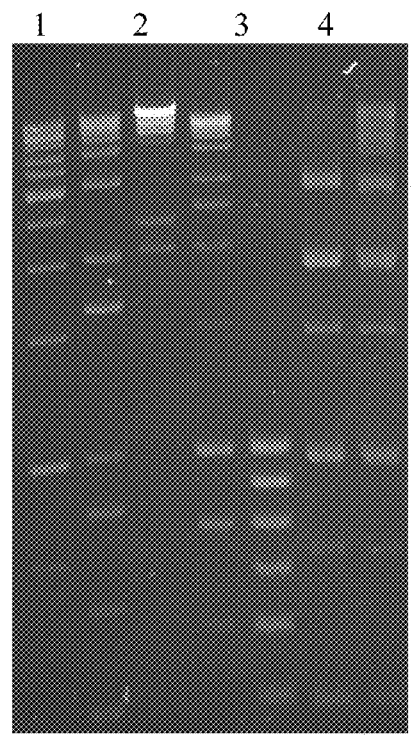

FIG. 8 (FIG. 8) illustrates pre-staining with Compound F (Table 1) in gels made from different agaroses. 1% Gels were poured using the (A) OmniPur (EMD) and (B) Seakem LE (Lonza) agarose. DNA samples were pre-stained with 1 uM Compound F. Gels were run in 1× lithium borate buffer. DNA samples were loaded as follow: (1) GeneRuler 1 kB ladder, (2) Invitrogen 1 kB, (3) Promega Lambda DNA-HindIII digest, (4) Bioline HyperLadder I, (5) Bioline HyperLadder IV, (6) Axygen M-DNA-LR, and (7) Axygen M-DNA-BR. Gels were visualized on the UVP GelDoc-It Imaging System using the SYBR Green emission filter setting. Pictures are from a 3 second exposure.

Figure 9:
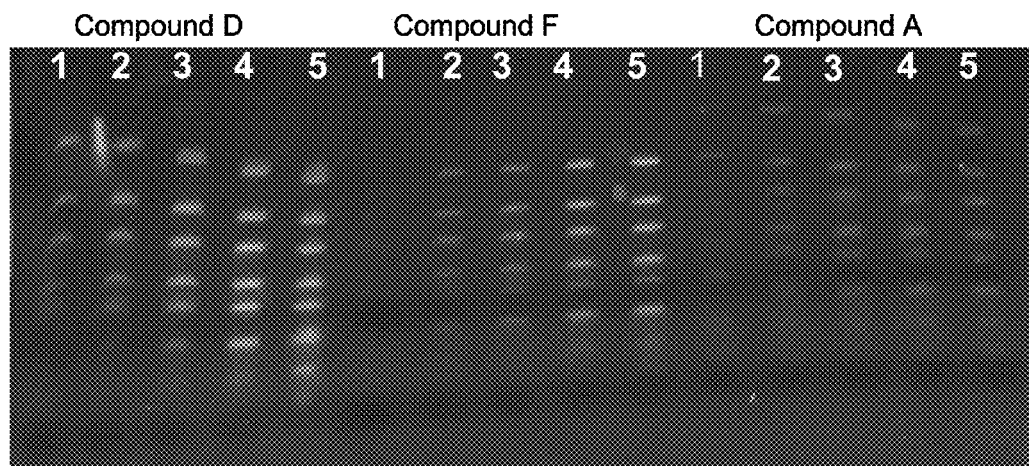
Figure 9:
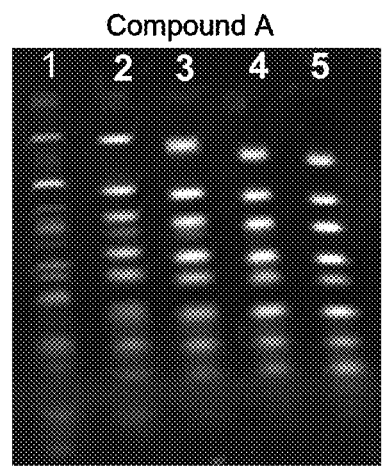

FIG. 9 (FIG. 9) illustrates a TBE Polyacrylamide Gel prestained with Compound D, Compound F or Compound A. A 4-20% TBE precast polyacrylamide gel was loaded with different concentration of the Fermentas GeneRuler Ultra Low Range DNA ladder. The gel was run in a Bio-Rad protean minigel system for one hour at 100 V. The DNA samples loaded are as follow (from left to right): (1) 31.25 ng, (2) 62.5 ng, (3) 125 ng, (4) 250 ng, (5) 500 ng of the GeneRuler Ultra Low Range DNA ladder. Picture was taken using the UVP GelDoc-It Imagining System using the (a) ethidium bromide and (b) SYBR Green emission filter settings.

DETAILED DESCRIPTION OF THE INVENTION

Herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether or not the term "inclusive" or the like appears, unless implicitly or explicitly understood or stated otherwise.

DEFINITIONS

Various terms are generally described or used herein to facilitate understanding. It will be understood that a corresponding general description or use of these various terms applies to corresponding linguistic or grammatical variations or forms of these various terms. It will also be understood that a general description or use or a corresponding general description or use of any term herein may not apply or may not fully apply when the term is used in a non-general or more specific manner. It will also be understood that the terminology used or the description provided herein, such as in relation to various embodiments, for example, is not limiting. It will further be understood that embodiments described herein or applications described herein, are not limiting, as such may vary.

Generally, the terms "stain" and "dye" may be used interchangeably and refer to an aromatic molecule capable of absorbing light in the spectral range of from about 250 nm to about 1,200 nm, inclusive. Generally, the term "dye" may refer to a fluorescent dye, a non-fluorescent dye, or both. Generally, the term "fluorescent dye" refers to a dye capable of emitting light when excited by another light of appropriate wavelength.

Generally, the term "fluorescence quencher" refers to a molecule capable of quenching the fluorescence of another fluorescent molecule. Fluorescence quenching can occur via at least one of the three ways. The first type of fluorescence quenching occurs via fluorescence resonance energy transfer (FRET) (Förster, *Ann. Phys.* (1948); and Stryer, et al., *Proc. Natl. Acad. Sci.* (1967)), wherein a quencher absorbs the emission light from a fluorescent molecule. The absorption peak of a FRET quencher usually has to have significant overlap with the emission peak of a fluorescent dye for the FRET quencher to be an efficient fluorescent quencher. A FRET quencher is typically a non-fluorescent dye, but can also be a fluorescent dye. When a quencher is a fluorescent dye, only the absorption property of the dye is utilized. A second type of fluorescence quenching occurs via photo-induced electron transfer (PET), wherein the quencher is an electron-rich molecule that quenches the fluorescence of a fluorescent molecule by transferring an electron to the electronically excited dye. A third type of fluorescence quenching occurs via dye aggregation, such as H-dimer formation, wherein two or more dye molecules are in physical contact with one another, thereby dissipating the electronic energy into the vibrational modes of the molecules. This type of contact fluorescence quenching can occur between two identical fluorescent dyes, or between two different fluorescent dyes, or between a fluorescent dye and a FRET quencher, or between a fluorescent dye and a PET quencher. Other types of fluorescence quenchers, though not used as commonly, include stable free radical compounds and certain heavy metal complexes.

The terms "polynucleotides", "nucleic acids", "nucleotides", "probes" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440.

Generally, the term "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding. Generally, the term "non-fluorescent, nucleic acid-binding molecule" refers to a nucleic acid-binding molecule that may or may not be a dye and that does not become fluorescent upon binding to nucleic acid. Generally, the term "fluorescent DNA dye" refers to a dye that becomes fluorescent upon binding to DNA. Generally, the term "fluorescent, non-nucleic acid dye" refers to a fluorescent dye that does not bind to nucleic acid. Generally, the term "non-fluorescent, non-nucleic acid dye" refers to a dye that is neither fluorescent nor nucleic acid-binding. Such a dye is commonly called a fluorescence quencher. Frequently, a fluorescence quencher is used to form a FRET pair with a fluorescent dye. Generally, the term "reporter dye" refers to a fluorescent dye whose emitted fluorescence contributes to the final detected fluorescence signal.

Generally, the term "TBE" refers to an aqueous buffer comprising about 89 mM Tris, about 89 mm borate, and about 2 mM EDTA, with a pH of about 8.3; the term "TAE" refers to an aqueous buffer comprising about 40 mM Tris, about 20 mM acetate, and about 2 mM EDTA, with a pH of about 8.1; and the term "EB" refers to ethidium bromide.

Generally, a salt that comprises a cation that is associated with a strong base and an anion that is associated with a strong acid refers to a salt that comprises such a cation and such an anion from whatever source, whether from the strong acid or strong base or from any other suitable source. The strong base may have a pKa of about 10 or greater, and the strong acid may have a pKa of about 2 or less. In this regard, "a cation that is associated with a strong base" generally refers to a cation that would be sufficient as a component of such a strong base, but need not actually be such a component, and "an anion that is associated with a strong acid" generally refers to an anion that would be sufficient as a component of such a strong acid, but need not actually be such a component. Merely by way of example, the salt may be one that when dissolved in water is sufficiently ionized, such as on the order of at least 90% ionized, for example. A concentration of such a salt in solution may be from about 5 mM to about 0.5 M, inclusive, such as about 0.05 M to about 0.2 M, or about 0.1 M, for example. Such a salt may be non-buffering. Generally, when a non-buffering salt is dissolved in water, it fully dissociates into the cation and anion without significantly changing the pH of the water. In this regard, a significant change may be a pH change of ±0.5, inclusive, such as ±0.3, inclusive, for example. Examples of such salts include, but are not limited to, sodium chloride, potassium chloride, sodium sulfate, potassium sulfate, sodium bromide, potassium bromide, tetramethylammonium chloride, magnesium choride, and/or the like.

In general, fluorescent nucleic acid dyes can be classified into two major classes: intercalators and minor groove-binders. Generally, fluorescent intercalators are dyes that bind to double-stranded DNA (dsDNA) or double-stranded RNA (dsRNA) by inserting themselves in between a neighboring base pair. Generally, minor groove-binders are dyes that bind to the minor groove of double-stranded DNA. There are still other dyes that may bind to nucleic acids via multiple modes, including electrostatic interaction between a positively charged dye and the negatively charged nucleic acid.

Disclosed herein are methods and compositions for detecting nucleic acids in gels. In some embodiments, the gels are electrophoretic gels. Nucleic acid prestaining methods, where a nucleic acid dye (including but not limited to a dimeric phenanthridinium dye, asymmetric cyanine dye, symmetric cyanine dye, and acridine dye) is mixed with a nucleic acid sample prior to loading the sample into a gel, loading the mixture in a gel, electrophoresing and visualizing are provided. The methods provided herein utilize unique loading and/or running buffers which eliminate the need for adding dyes to the gel matrix directly (e.g., in-gel or pre-cast addition), and thus reducing the needed amount of dye for efficient visualization and reduce the chance of exposure to potentially harmful dyes. Accordingly, the method of the invention offers convenience, lowers dye cost and improved safety.

In one embodiment, the present invention provides a method of detecting the presence or absence of a nucleic acid in a sample, comprising:

(a) combining a sample comprising a nucleic acid with at least one fluorescent nucleic acid binding dye having the formula:

wherein BRIDGE is a substantially neutral covalent linker comprising from about 1 to about 150 non-hydrogen atoms;

$Q_1$ is a phenanthridinium dye, an acridinium dye or an asymmetric cyanine dye;

$Q_2$ is a phenanthridinium dye, an acridinium dye or an asymmetric cyanine dye;

(b) loading said sample into a gel, wherein said gel comprising a gel buffer, said gel buffer comprising at least one weak acid and a salt of said at least one weak acid;

(c) electrophoresing said sample; and (d) detecting fluorescence associated with the sample or a lack thereof In some embodiments, a nucleic acid sample is combined with a loading buffer comprising a nucleic acid dye (e.g., a dimeric phenanthridinium dye, a dimeric acridinium dye, or a dimeric asymmetric cyanine dye). The combination of dye and nucleic acid can then be loaded into an electrophoresis gel. The gel can contain a gel buffer and/or can be submerged in a running buffer. The gel buffer and the running buffer can be the same buffer. In some embodiments, the gel buffer and the running buffer each contains a weak acid and a salt of the weak acid including but not limited to salt of lithium, tris, sodium, potassium, and cesium. A preferred running buffer comprises a weak acid and a lithium salt thereof. In other embodiments, the weak acid present in the gel buffer and the running buffer is the same weak acid. Following loading, the gel is run and illuminated during and/or after electrophoresis to visualize the dye-nucleic acid complexes.

Loading buffers can also comprise a high-density material which facilitates sinking of the nucleic acid sample into the gel matrix during sample loading. Examples of suitable high-density material include, but are not limited to, glycerol, sucrose, and Ficoll. The loading buffer optionally further comprise at least one of the following ingredients: water, a pH buffer, a metal chelator, a detergent, at least one loading dye and one or more additional agent that facilitates sample loading or electrophoresis. Generally, the loading buffer comprises at least one loading dye. The loading dye is generally a negatively charged dye that does not bind to nucleic acids but runs in the same direction as the nucleic acids do under the electric field. The loading dye gives an indication on how "fast" the gel is running. In some cases a mixture of two differently colored loading dyes are used, where one dye is used for following the migration of the relatively fast-moving small nucleic acid fragments and another dye for following the migration of the relatively slow-moving large nucleic acid fragments. Examples of suitable loading dyes include, but are not limited to, Xylene cyanol, Cresol red, Bromophenol blue, Orange G, and Tartrazine.

Electrophoresis gels suitable for the invention can include agarose gels, polyacrylamide gels or similar matrix suitable for electrophoretic separation of nucleic acids. Methods for preparing electrophoresis gels are well known to those of skill in the art. For agarose gels, agarose powder is usually mixed with a buffer (i.e., gel buffer) and then heated to form a liquid solution, which is poured into a gel tray, followed by cooling to room temperature to form a gel. The amount of agarose determines the pore size of the gel matrix, which in turn affects the nucleic acid migration rate and resolution. For most applications, a 0.7 to 1.5% (w/v) agarose gel provides good nucleic acid separation. A higher (i.e. 2-4%) agarose amount may be used for relatively small nucleic acid fragments. Polyacrylamide gels are usually used for separating small DNA or RNA fragments and are generally prepared by copolymerization of acrylamide and bisacrylamide in the presence of catalysts.

The buffer within the gels (e.g., a "gel buffer") and the optional running buffer (e.g., the buffer that bathes the gel) are a component of the present inventions disclosed herein. In some instances, the gel buffer and the running buffer can comprise the same buffer. In other instances, the gel buffer and the running buffer comprise different buffers. Where the gel buffer and the running buffer are the same, the term "gel electrophoresis buffer" is used herein. For example, a gel can be prepared from agarose powder using the same buffer as used for the running buffer. In still other instances, the gel buffer and the running buffer differ in overall composition, but contain a buffer element in common. For example, where the running buffer contains lithium borate, the gel buffer can contain other borate compounds including, but not limited to tris borate, sodium borate, cesium borate, potassium borate, or any other acceptable borate-containing compound. In some embodiments, a running buffer may not be needed, for example, using the E-Gel® system (Invitrogen) where a gel comprising a gel buffer as described herein can be directly used without a running buffer. This system also allows monitoring of electrophoresis in real time.

In general, the gel buffer and running buffer both comprise a weak acid and a salt of the acid. In a particular embodiment, the salt is a lithium salt. The $pK_a$ of a weak acid useful for practicing the methods described herein can be from about 8 to about 10.5, from about 8.5 to about 9.5, or from about 9.0 to about 9.2. An exemplary weak acid is boric acid ($H_3BO_3$), but any other appropriate weak acid can be utilized. Thus, in one embodiment of the present invention the gel buffer, the running buffer and/or the gel electrophoresis buffer comprises boric acid and lithium borate. Typically, the amount of anion released from the weak acid and the salt of the weak acid can be controlled so as to determine a pH range of a buffer. For example, in a borate buffer (e.g., a gel buffer comprising boric acid and lithium borate) can comprise an amount of borate (i.e., the total amount of borate from both lithium borate and boric acid) to render the pH of the buffer to be at about 8.5. Additionally, the amount of cation released from the salt of the weak acid (e.g., $Li^+$ from lithium borate) can be determined by adding differing amounts of the salt. In some embodiments utilizing lithium salts, the concentration of $Li^+$ is about 0.5 to about 30 mM or about 10 mM.

A buffer may optionally comprise one or more of the following components: a magnesium chelator (such as EDTA), a detergent, a preservative, and one or more additional buffers. The pH of buffers useful for practicing the methods disclosed herein can be from about 7.7 to about 9, from about 8 to about 8.8, or about 8.5. The range of pH provided can refer to the pH of a 1× buffer. A more concentrated gel electrophoresis buffer is usually prepared as a stock solution, which can be diluted to a 1× working solution by addition of a diluent (e.g., water). Stock solutions of buffers useful in the methods described herein can be at least 2×, at least 5×, at least 10×, at least 20× or at least 25×.

The voltage applied for the gel electrophoresis determines the speed of nucleic acid migration; the higher the voltage, the faster the nucleic acids migrate. Alteration of voltage to control electrophoresis is well known in the art. In general, a voltage at 5-30 volt/cm is applied. More commonly, a 10 volt/cm voltage is applied.

Visualization of electrophoresis of nucleic acid samples can be carried out during electrophoresis to monitor the progress of the nucleic acid separation. A source of light with a suitable wavelength is applied to illuminate the dye. Typically, the wavelength of the excitation light should be at, or close to, an absorption peak of the nucleic acid binding dye. Dyes of useful for the invention disclosed herein can have sufficient absorption in the UV range from about 230 nm to about 320 nm to allow the nucleic acid dye to be excited. Thus, a UV illuminator box commonly used for ethidium bromide-based gel viewing is suitable for use with some dyes disclosed herein (e.g., dimeric phenanthridinium dyes). The dimeric phenanthridinium-based dyes according to the invention are particularly suitable for UV excitation due to their good extinction coefficients in the wavelength range. Alternatively, a visible light with a wavelength close to or, even better, at the absorption peak in the visible wavelength range is used to excite the dye. Visible light excitation has the advantage of causing less damage to nucleic acid samples and also being less harmful than UV light. Visible light excitation may produce the best sensitivity on instruments equipped with a laser. Detection can be made by direct viewing with naked eyes, or by digital filming. Commercial devices, such as the E-Gel® system from Invitrogen, permit one to monitor gel electrophoresis in real-time. The method of the invention herein is fully compatible with such a system.

Visualization of stained nucleic acids can be carried out following gel electrophoresis. For example, after the electrophoresis has been completed, the gel containing the separated nucleic acid bands may be viewed/filmed on any of the commercial gel documentation instruments widely commercially available. Gel documentation instruments may include relatively inexpensive ones that comprise a simple UV box for excitation and a Polaroid camera for filming, and high-end instruments that are equipped with lasers and a CCD camera detection system. The methods of the invention are fully compatible with any of these instruments/devices.

Further disclosed herein is a kit comprising a gel electrophoresis buffer according to the invention, a loading buffer comprising a dimeric nucleic acid-binding dye according to the invention, and an instruction manual. Optionally, the loading buffer in a kit further comprises at least one loading dye. A gel electrophoresis buffer in the kit can be at least 2×, 5×, 10×, 20× or 25×. In some instances, a gel electrophoresis buffer in a kit is provided as a lyophilized solid. Loading buffers present in the kit can be provided at different concentrations, for example, about 2×, 3×, 4×, 5×, 7×, 8×, 9×, 10×, 15×, 20×, 25× or higher. A kit may further comprise a gel-forming substance (e.g., agarose powder) for production of electrophoretic gels. Alternatively, a kit can contain one or more precast gels comprising a buffer disclosed herein. The kit may optionally further comprise a nucleic acid ladder or other control sample.

A variety of nucleic acid binding dyes can be used for practicing the subject methods. One exemplary class of dyes are dimeric dyes, which possess several desirable characteristics. By way of example, such a dye may have a background fluorescence that is reduced relative to that of its monomeric dye constituents. Relatively low background fluorescence generally corresponds to relatively enhanced nucleic acid detection sensitivity. Thus, such a dimeric dye is generally associated with enhanced nucleic acid detection sensitivity. Further by way of example, a dimeric dye may be more thermally and/or hydrolytically stable than SYBR Green I. Still further by way of example, a dimeric dye may be less toxic, particularly less mutagenic, than some of the dyes previously used in nucleic acid gel stains.

Dimeric dyes comprising a substantially neutral linker have been demonstrated to be superior to monomeric dyes in detecting nucleic acid in electrophoresis gels (U.S. Pat. No. 7,601,498). The dimeric dyes have several advantages over the monomeric dyes. First, dimeric dyes can form an intramolecular dimer in the absence of nucleic acids and as a result have very low background fluorescence. Additionally, dimeric dyes have high nucleic acid binding affinity, permitting both nucleic acid binding and separation of the dyes from nucleic acid samples for potential recovery and/or manipulation after separation (e.g., by elelctrophoresis). Furthermore, dimeric dyes are generally nonmutagenic or only weakly mutagenic because of their inability to cross cell membranes.

Figure 1:
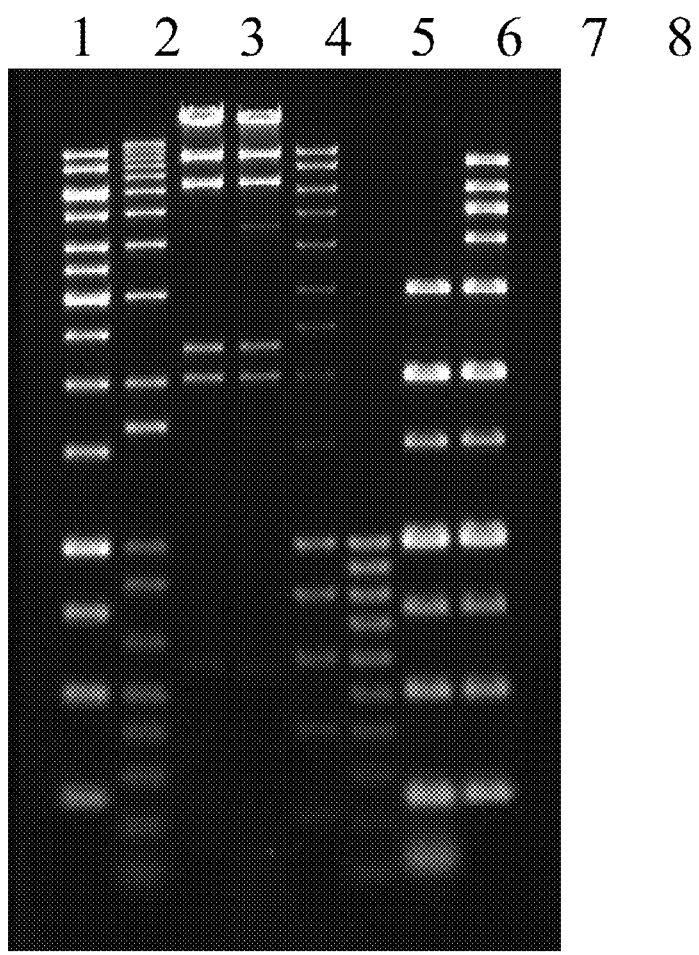
FIG. 1 (FIG. 1) illustrates post-staining of different samples with Compound A (Table 1). 1% OmniPur agarose (EMD) gel was ran in 1×TBE running buffer. Post-staining of the gel was performed using Compound A (3 uM) for 30 minutes. Samples in the lanes from left to right are as followed: (1) GeneRuler 1 kB ladder, (2) Invitrogen 1 kB ladder, (3) New England BioLabs Lambda DNA-HindIII Digest, (4) Promega Lambda DNA-HindIII Digest, (5) Bioline HyperLadder I, (6) Bioline HyperLadder IV, (7) Axygen M-DNA-LR, and (8) Axygen M-DNA-BR.

The sensitivity of dimeric dyes in detecting nucleic acids in gels is demonstrated in FIG. 1, where DNA ladders from various suppliers are first electrophoretically separated in an agarose gel and then post-stained with Compound A (Table 1). Compound A also demonstrates low background fluorescence, such that destaining or washing is not necessary. While post-gel staining prevents the possibility that nucleic acid migration is affected by the dye, the extra staining step involved in this method is not only more time-consuming but also makes the procedure less safe.

TABLE 1

Selected examples of dimeric phenanthridinium dyes

| Compound | Structure |
|---|---|
| A | 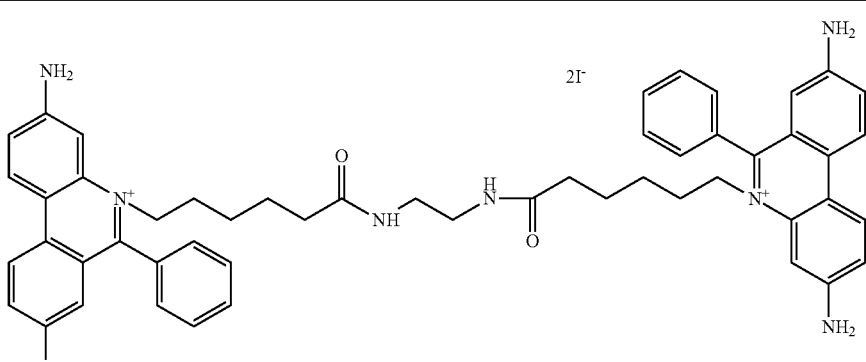 |

TABLE 1-continued
Selected examples of dimeric phenanthridinium dyes
| Compound | Structure |
|---|---|
| B | 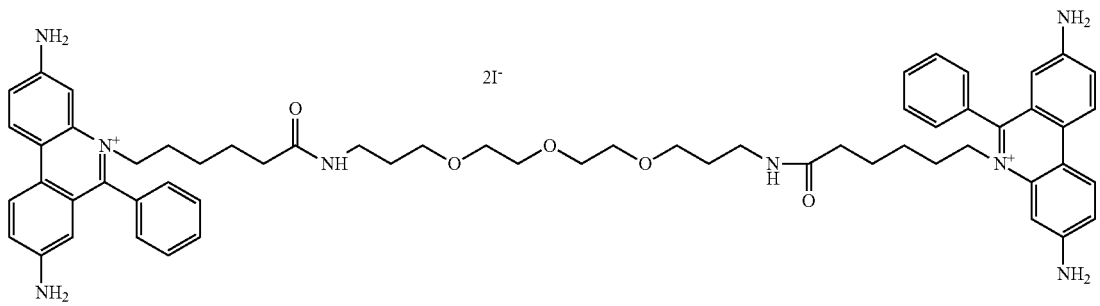 [SMILES: Nc1ccc2c(c1)c(-c1ccccc1)[n+](CCCCCC(=O)NCCCOCCOCCOCCCNC(=O)CCCCC[n+]1c(-c3ccccc3)c3cc(N)ccc3c3ccc(N)cc31)c1cc(N)ccc21] |
| C | 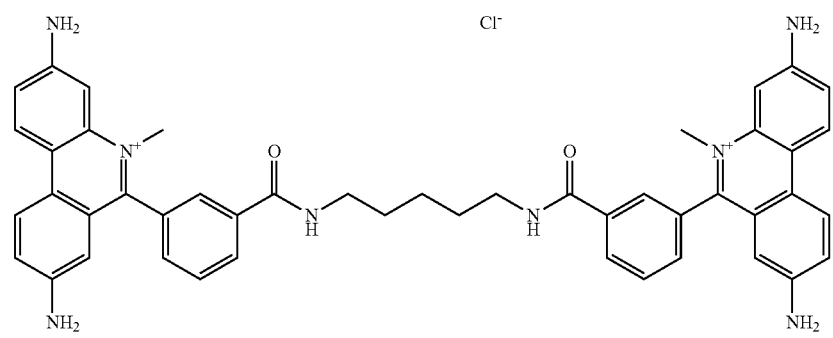 [SMILES: [Cl-] ; C[n+]1c(-c2cccc(C(=O)NCCCCCNC(=O)c3cccc(-c4c5cc(N)ccc5c5ccc(N)cc5[n+]4C)c3)c2)c2cc(N)ccc2c2ccc(N)cc21] |
| D | 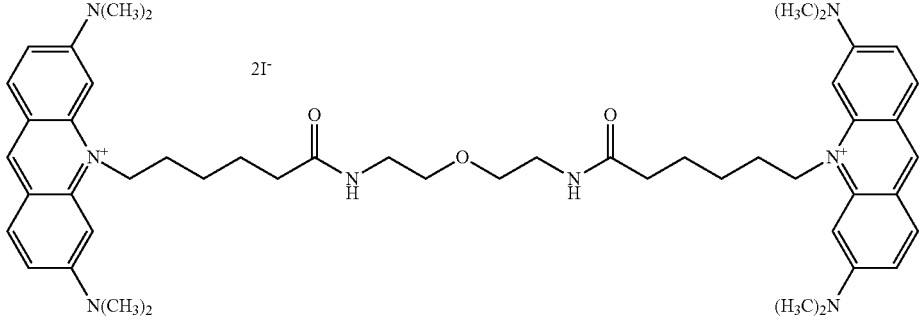 |
| E | 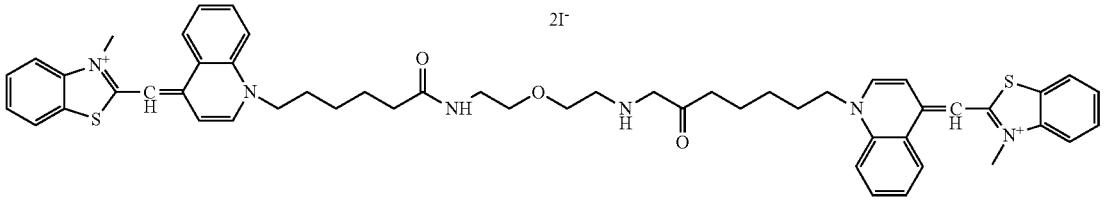 [SMILES: C[n+]1c(C=C2C=CN(CCCCCC(=O)CNCCOCCNC(=O)CCCCCN3C=CC(=Cc4sc5ccccc5[n+]4C)c4ccccc43)c3ccccc32)sc2ccccc21] |
| F | 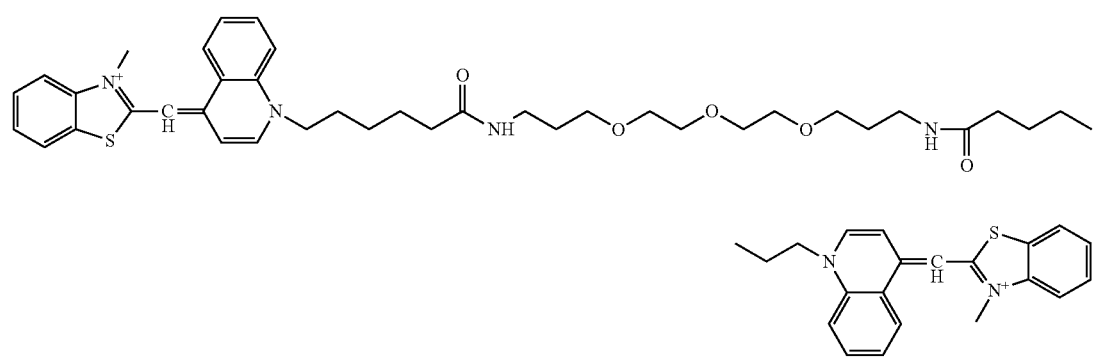 |

TABLE 1-continued

Selected examples of dimeric phenanthridinium dyes

| Compound | Structure |
|---|---|
| G | 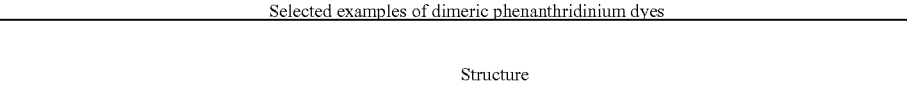 |

A fluorescent dimeric nucleic acid dye to be utilized in the subject method may have the general structure (Structure 1) set forth directly below.

Structure 1

In relation to the brief summary and the description, references to a dimeric dye are to a dimeric dye of Structure 1. In Structure 1, each of $Q_1$ and $Q_2$ is a fluorescent nucleic acid dye. $Q_1$ and $Q_2$ may be selected and combined in a manner to encourage or to ensure desired properties of the resulting dimeric dye. BRIDGE may be positively charged to a relatively limited extent or substantially neutral in charge, and may be a substantially flexible constituent that facilitates intramolecular dimer formation to produce the dimeric dye.

BRIDGE may be a substantially flexible linker molecule, having no more than one positive charge. BRIDGE may be a substantially neutral and substantially flexible linker molecule. The constituents of BRIDGE may be selected to provide such limited positive charge or substantial neutrality. The property of substantial neutrality, which includes actual neutrality, is discussed further below. The property of substantial flexibility is generally related to the substantially aliphatic nature, which includes actual aliphatic nature, of BRIDGE. This substantial aliphatic nature generally refers to the non-aromaticity of BRIDGE, or non-rigidity of BRIDGE. Herein the term "substantially neutral" means that the BRIDGE moiety may comprise no more than one positive charge. When the amount of charge is between 0 and +1, it means that the BRIDGE moiety comprises a single weak base moiety, which may become protonated to form a positive charge. However, since the moiety is a weak base, only a fraction of the total molecules having such a moiety will become protonated. As a result, on average, that moiety will produce a positive charge between 0 and +1. Examples of a weak base moiety include a primary amine, a secondary amine, a tertiary amine or a $SP^2$-hybridized nitrogen. Preferably, the BRIDGE moiety is neutral, i.e., zero charge on the BRIDGE.

In Structure 1, BRIDGE is covalently attached to $Q_1$ and $Q_2$. In a dimeric dye, BRIDGE may generally have from about 8 to about 150 non-hydrogen atoms, inclusive; from about 10 to about 100 non-hydrogen atoms, inclusive; from about 15 to about 80 non-hydrogen atoms, inclusive; or from about 20 to about 50 non-hydrogen atoms, inclusive.

BRIDGE may incorporate at least one independent nucleic-acid-binding-enhancing-group (NABEG). A NABEG is a moiety capable of binding to nucleic acids in the form of electrostatic, hydrophobic, or hydrogen-bonding interactions. Merely by way of example, a NABEG may be selected from primary amines; secondary amines; tertiary amines; ammoniums; amidines; aryl groups optionally comprising hetero atoms selected from N, O, S, and any combination thereof; moieties having bonds comprising hetero atoms of high electronegativity; and any combination thereof.

Primary, secondary and tertiary amines and amidines are basic groups and therefore are positively charged or at least partially positively charged at physiological pH. Ammonium groups, or quaternized nitrogen groups, are permanently positively charged. Generally speaking, positively charged or partially positively charged groups enhance the nucleic acid binding of the dye via electrostatic interaction, a property that may be exploited in the development of highly sensitive fluorescent nucleic acid stains. It is generally undesirable to use BRIDGE having excessive positive charges to produce a dimeric dye. A suitable BRIDGE of a dimeric dye may comprise no more than one positive charge. BRIDGE may be a substantially flexible and neutral or substantially neutral linker. In this context, substantially neutrality refers to slight charge. By way of example, BRIDGE could comprise a weakly basic constituent, such as a pyridine group or a pyrazine group, for example, such that when it is in aqueous solution, a very small amount of positive charges may be present. Further by way of example, in a case in which BRIDGE comprises at least one neutral NABEG, the exact amount of positive charge is generally related to the $pK_a$ of the NABEG. Generally, the higher the $pK_a$ of the NABEG, the more likely the NABEG is protonated and thus, positively charged. By way of example, a suitable weakly basic NABEG group may have a $pK_a$ of about 11 or less, inclusive; about 8 or less, inclusive; or about 7 or less, inclusive.

There may be a tendency to form an intramolecular dimer, primarily H-dimer, which may be a particularly useful property in the nucleic acid dye produced. For example, in the case of a dimeric dye, H-dimer formation produces a hairpin-like structure, wherein H-dimer forms a stem portion of the hairpin and BRIDGE forms a curved portion, as schematically illustrated in FIG. 1. The phenomenon of H-dimer formation in connection with certain dyes has been described in West, et al., *J. Phys. Chem.* (1965); Rohatgi, et al., *J. Phys. Chem.* (1966); Rohatgi, et al., *Chem. Phys. Lett.* (1971); and Khairutdinov, et al., *J. Phys. Chem.* (1997). Formation of an intramolecular H-dimer may be facilitated when BRIDGE is a flexible and neutral or substantially neutral hydrocarbon linker, optionally comprising one or more neutral NABEG(s).

H-dimer formation in a dimeric dye may be associated with another major benefit. This unexpected benefit is that H-dimer formation in a dimeric dye may significantly reduce the toxicity, particularly mutagenicity, of the dye. In this regard, a significant reduction in mutagenicity may be on the order of at least about 20% relative to EB, as measured using the Ames Test or an equivalent test. It is believed that reduced mutagenicity may be at least partly attributable to reductions in the cell membrane-permeability and the effective concentration of the dye. The molecular weight of a dimeric dye is generally substantially or significantly larger, such as about two times larger, for example, than the molecular weights of known nucleic acid gel stains. Generally, a molecule having a larger molecular weight has more difficulty penetrating cell membranes than a molecule having a smaller molecular weight. As such, a molecule having a large molecular weight may be relatively less likely to enter a cell and cause cell damage. As to a dimeric dye molecule that successfully enters a cell, the effective concentration of the dye associated with the molecule is generally relatively small because of H-dimer formation. As such, the dimeric dye molecule may be relatively less likely to cause cell damage once it enters a cell.

BRIDGE may have the formula (Formula 1) set forth directly below.

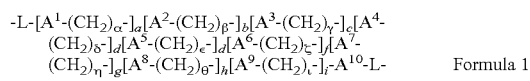
Formula 1

In Formula 1, each L is part of BRIDGE and is covalently linked to $Q_1$ or $Q_2$. Each L is independently a moiety comprising a single bond; a polymethylene unit having 1 carbon to about 12 carbons, inclusive, optionally comprising at least one hetero atom selected from N, O and S; or an aryl group optionally comprising at least one hetero atom selected from N, O and S. The subscripts associated with the (CH$_2$) methylene units, namely, $\alpha, \beta, \gamma, \delta, \epsilon, \zeta, \eta, \theta$, and $\iota$, may be the same or different, each independently indicating the size of the associated methylene unit and, independently, being zero or an integer from 1 to about 20, inclusive, or from 1 to about 12, inclusive. The subscripts associated with the bracketed portions of Formula 1, namely, a, b, c, d, e, f, g, h, and i, may be the same or different, each independently indicating the size of the associated bracketed portion of the formula and, independently, being zero or an integer from 1 to about 20, inclusive, or from 1 to about 10, inclusive, or from 1 to about 5, inclusive.

$A^1, A^2, A^3, A^4, A^5, A^6, A^7, A^8, A^9$, and $A^{10}$ may be the same or different, each, independently, being a nucleic-acid-binding-enhancing-group (NABEG); a branched alkyl optionally comprising at least one hetero atom selected from N, O and S; or at least one saturated 5- or 6-membered ring optionally comprising at least one hetero atom selected from N, O and S. $A^1, A^2, A^3, A^4, A^5, A^6, A^7, A^8, A^9$, and $A^{10}$ may be such that BRIDGE comprises at most one positive charge, or is substantially neutral, and in the latter case, each of these constituents, independently, may itself be substantially neutral, which includes actual neutrality. NABEGs may be selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond.

$A^1, A^2, A^3, A^4, A^5, A^6, A^7, A^8, A^9$, and $A^{10}$, which may be the same or different, may, independently, be NABEGs selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond. $A^1, A^2, A^3, A^4, A^5, A^6, A^7, A^8, A^9$, and $A^{10}$ may be such that BRIDGE comprises at most one positive charge, or is substantially neutral, and in the latter case, each of these constituents may itself be substantially neutral, which includes actual neutrality.

BRIDGE may comprise any suitable number of non-hydrogen atoms, as previously described, such as from about 10 to about 100 non-hydrogen atoms, inclusive, merely by way of example.

Merely by way of example, BRIDGE may have the formula (Formula 2) set forth directly below.

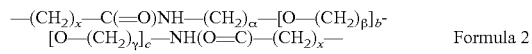
Formula 2

In one such case, for example, each L of BRIDGE is —(CH$_2$)$_x$—, where each x, independently, is an integer selected from 1 to 11, inclusive; $A^1$ of BRIDGE is —C(=O)NH—; a of BRIDGE is 1; $A^2$ of BRIDGE is —O—; $A^3$ of BRIDGE is —O—; $\alpha$ may be an integer selected from 2 to about 20, inclusive; each of $\beta$ and $\gamma$, independently, may be 2 or 3; b may be zero or an integer selected from 2 to about 20; and c may be zero or 1; each of d, e, f, g, h and i of BRIDGE is 0; and $A^{10}$ of BRIDGE is —NH(O=C)C—. Merely by way of example, BRIDGE may be as just described, wherein c is 1. Further, merely by way of example, BRIDGE may be as just described, wherein c is 1, and further, wherein x may be 5; $\alpha$ and $\gamma$ may be the same and may be 2 or 3; $\beta$ may be 2; and b may be 0, 1, 2 or 3.

Each of the constituent monomeric dyes, Q1 and Q2, of the dimeric dye is a fluorescent nucleic acid dye. In general, Q1 and Q2 are selected and covalently linked via BRIDGE in a manner to encourage or to ensure intramolecular dimer formation in the absence of DNA and formation of highly fluorescent DNA-dye complexes upon DNA binding. A dimeric dye may have a tendency to form an intramolecular dimer as may be associated with the formation of a useful hairpin-like structure, as previously described. Such a dimeric dye may possess desirable properties, such as low background fluorescence and low toxicity, for example.

Intramolecular dimer formation may be confirmed by comparing absorption spectra of a dimeric dye in an aqueous solution and absorption spectra of the related monomeric dye or dyes also in an aqueous solution. Any intramolecular dimer formation should cause the spectra of the component monomeric dyes in the dimeric dye to be shifted significantly relative to the spectra of the related monomeric dye(s). In this regard, a significant shift may be about 10 nm or more, by way of example.

When the intramolecular dimer formation is an H-dimer formation, the spectra will usually undergo a significant blue shift. In this regard, a significant shift may be about 10 nm or more, by way of example. Other types of intramolecular dimer formation are also possible and may result in spectral shift in another direction, in insignificant spectral shift, or the like. In this regard, an insignificant shift may be about 5 nm or less, by way of example. Additional analytical methods for detecting intramolecular dimer formation may include nuclear magnetic resonance (NMR), infrared spectroscopy (IR), or the like. Any intramolecular dye aggregation that results in a hairpin structure is generally desirable.

The constituent monomeric dyes Q1 and Q2 are independently selected from a phenanthridinium, acridinium dye, an asymmetric cyanine dye and derivatives thereof. In most of the cases, $Q_1$ and $Q_2$ are the same.

Various combinations of $Q_1$ and $Q_2$ may be useful or desirable. By way of example, examples of dimeric dyes and associated intermediates are listed below in Table 2.

TABLE 2

Exemplary Fluorescent Nucleic Acid Dyes

| No. | Name | Structure | MWt. | SPACER LENGTH (ATOMS) |
|---|---|---|---|---|
| 1 | DMAO | 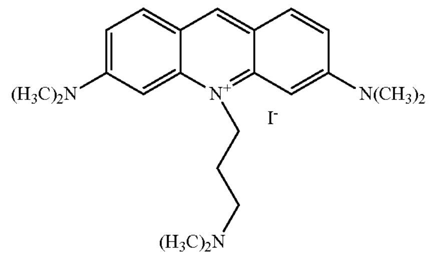 | 478.41 | N/A |
| 2 | TMAO | 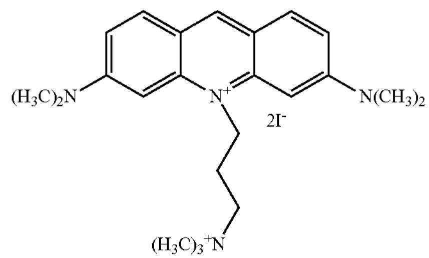 | 620.35 | N/A |
| 3 | AO-3N | 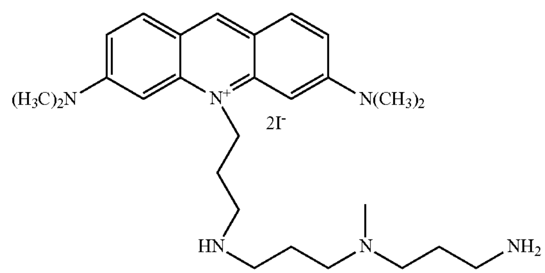 | 705.16 | N/A |

TABLE 2-continued

Exemplary Fluorescent Nucleic Acid Dyes

| No. | Name | Structure | MWt. | SPACER LENGTH (ATOMS) |
|---|---|---|---|---|
| 4 | AO-2N | 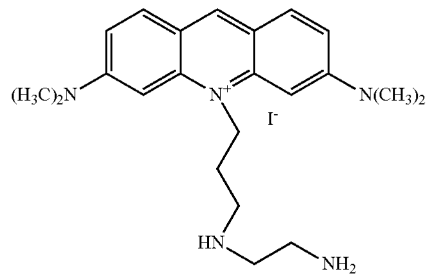 | 493.43 | N/A |
| 5 | PMAO | 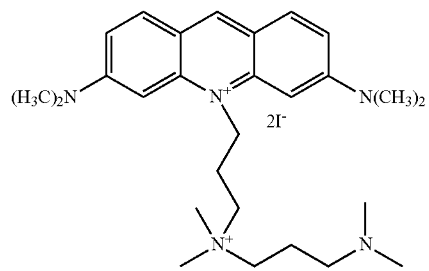 | 691.47 | N/A |
| 6 | AOAO-1 | 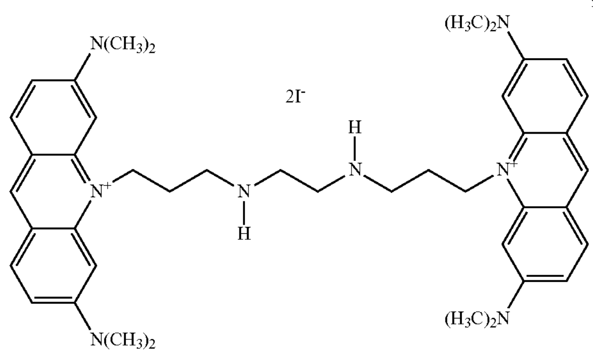 | 926.76 | 10 |

TABLE 2-continued
Exemplary Fluorescent Nucleic Acid Dyes
| No. | Name | Structure | MWt. | SPACER LENGTH (ATOMS) |
|---|---|---|---|---|
| 7 | AOAO-2 | 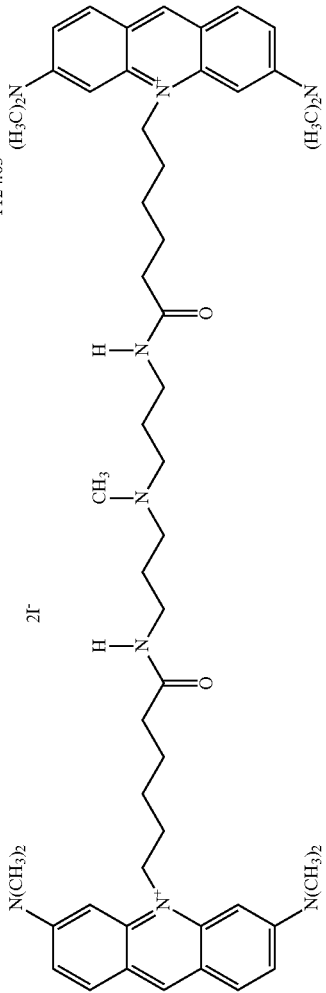 | 1124.03 | 21 |
| 8 | AOAO-3 | 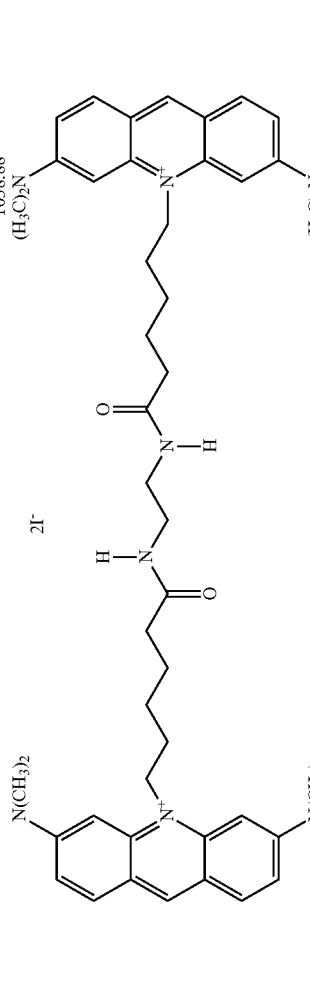 | 1038.88 | 16 |

TABLE 2-continued
Exemplary Fluorescent Nucleic Acid Dyes
| No. | Name | Structure | MWt. | SPACER LENGTH (ATOMS) |
|---|---|---|---|---|
| 9 | AOAO-2Q | 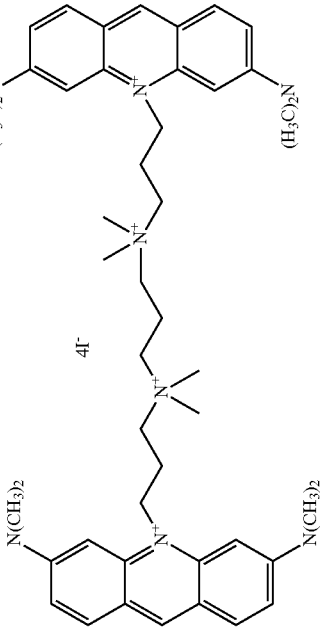 | 1252.71 | 11 |
| 10 | AOAO-4 | 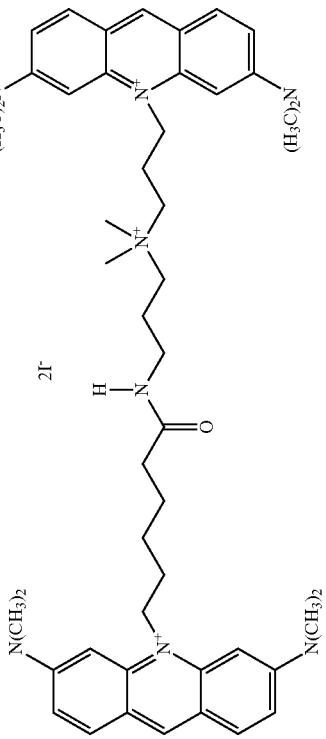 | 1041.95 | 14 |

TABLE 2-continued
Exemplary Fluorescent Nucleic Acid Dyes
| No. | Name | Structure | MWt. | SPACER LENGTH (ATOMS) |
|---|---|---|---|---|
| 11 | AOAO-5 | 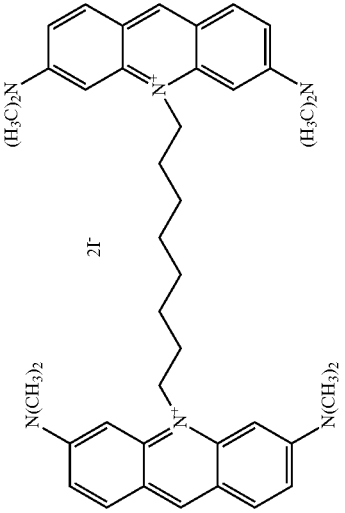 | 896.73 | 8 |
| 12 | AOAO-6 | 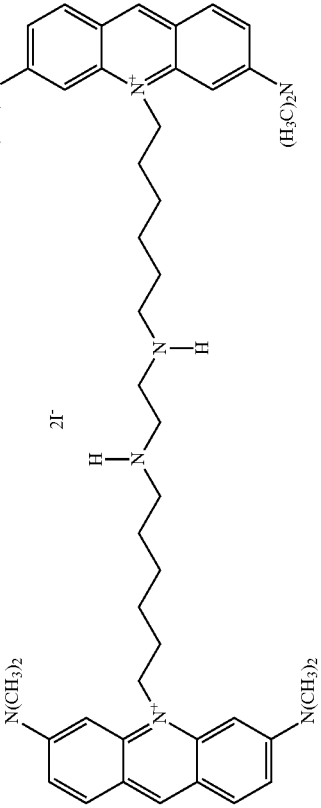 | 1010.92 | 16 |

TABLE 2-continued
Exemplary Fluorescent Nucleic Acid Dyes
| No. | Name | Structure | MWt. | SPACER LENGTH (ATOMS) |
|---|---|---|---|---|
| 13 | AOAO-7 | 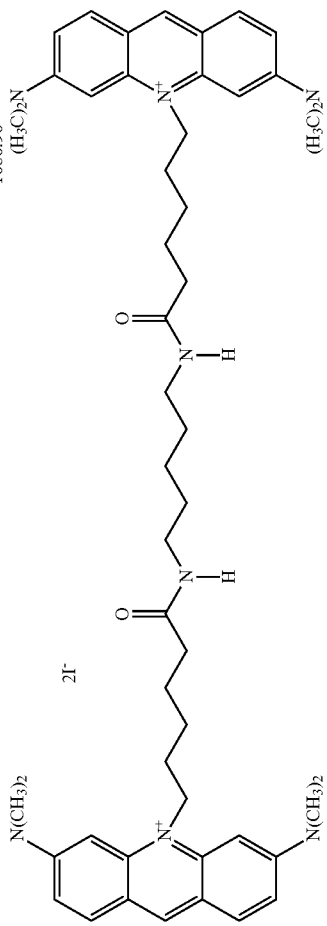 | 1080.96 | 19 |
| 14 | TOTO-3 | 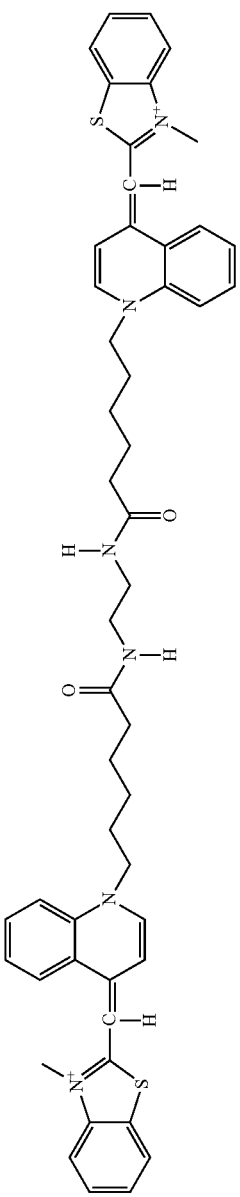 | 1088.94 | 16 |
| 15 | AOAO-8 | 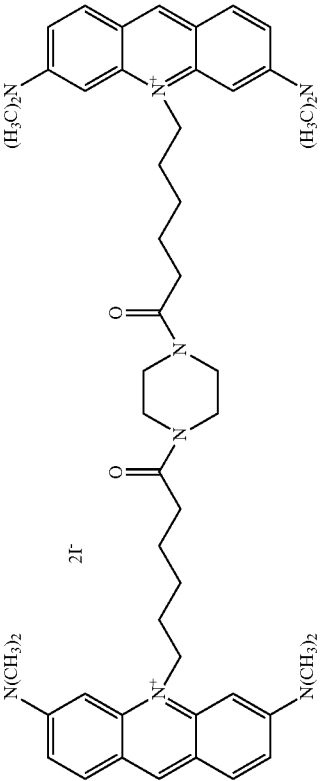 | 1064.92 | 16* |

TABLE 2-continued

Exemplary Fluorescent Nucleic Acid Dyes

| No. | Name | Structure | MWt. | SPACER LENGTH (ATOMS) |
|---|---|---|---|---|
| 16 | AOAO-9 | 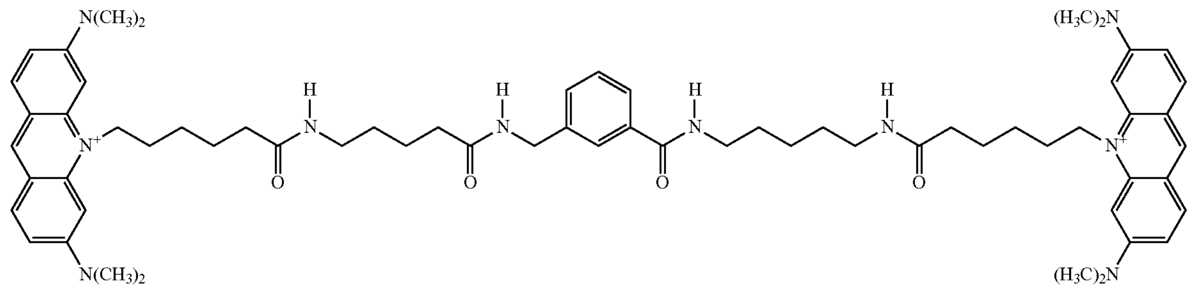 | | 25 |
| 17 | AOAO-10 | 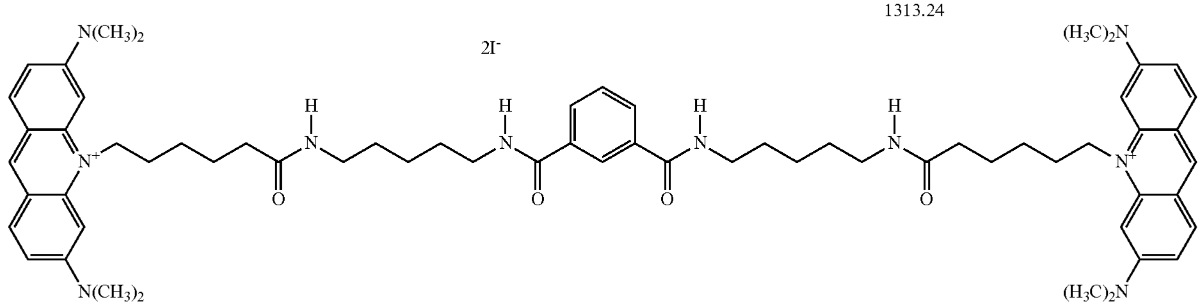 | 1313.24 | 31 |

TABLE 2-continued
Exemplary Fluorescent Nucleic Acid Dyes
| No. | Name | Structure | MWt. | SPACER LENGTH (ATOMS) |
|---|---|---|---|---|
| 18 | AOAO-11 | 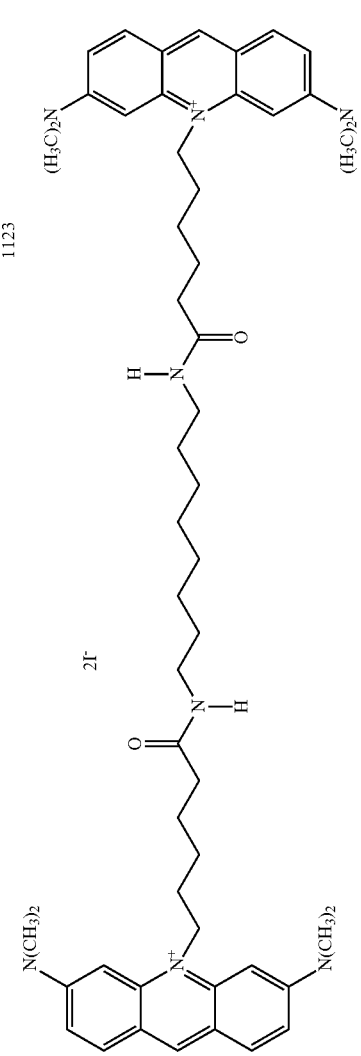 | 1123 | 22 |
| 19 | AOAO-12 | 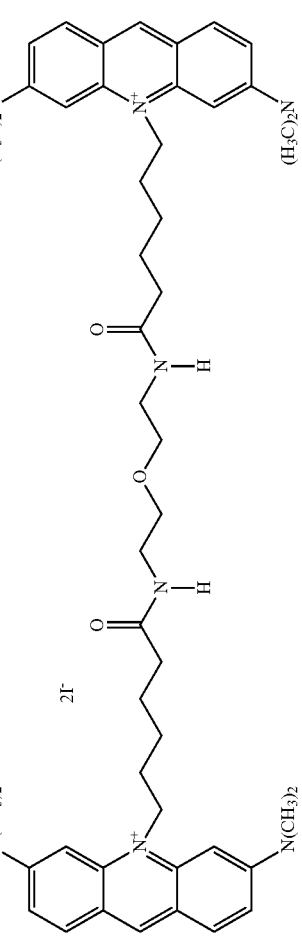 | 1082.94 | 19 |

TABLE 2-continued

Exemplary Fluorescent Nucleic Acid Dyes

| No. | Name | Structure | MWt. | SPACER LENGTH (ATOMS) |
|---|---|---|---|---|
| 20 | AOAO-13 | 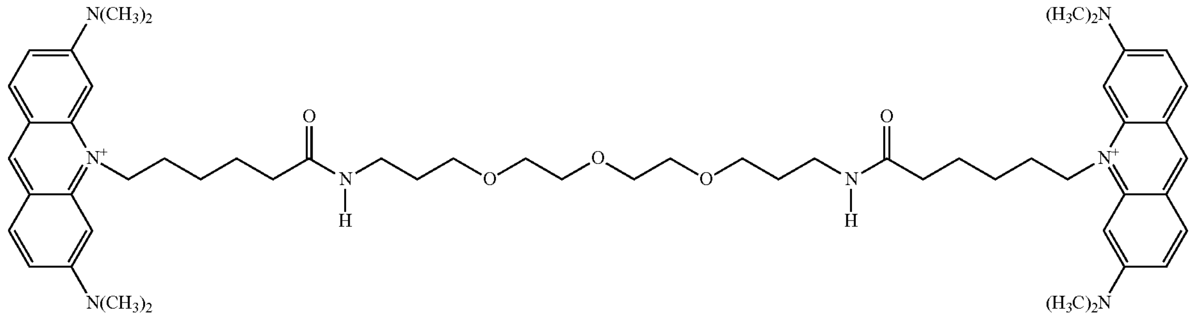 | 1215.14 | 27 |
| 21 | AOAO-14 | 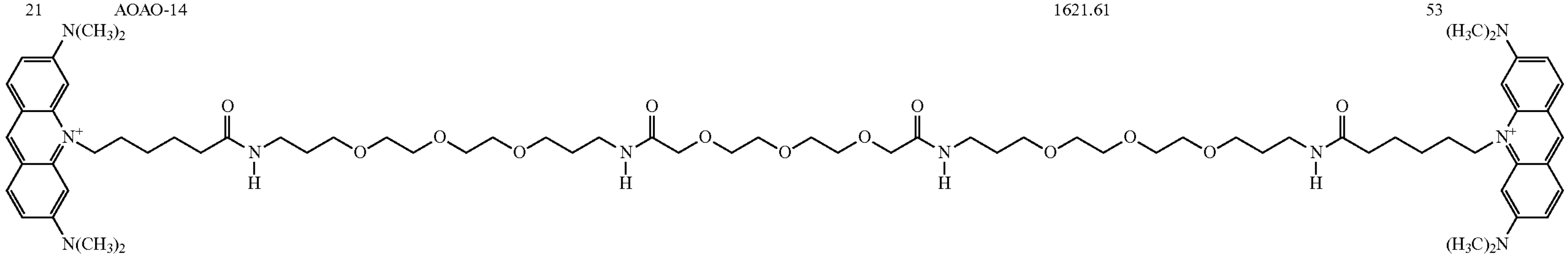 | 1621.61 | 53 |
| 22 | AOAO-12R | 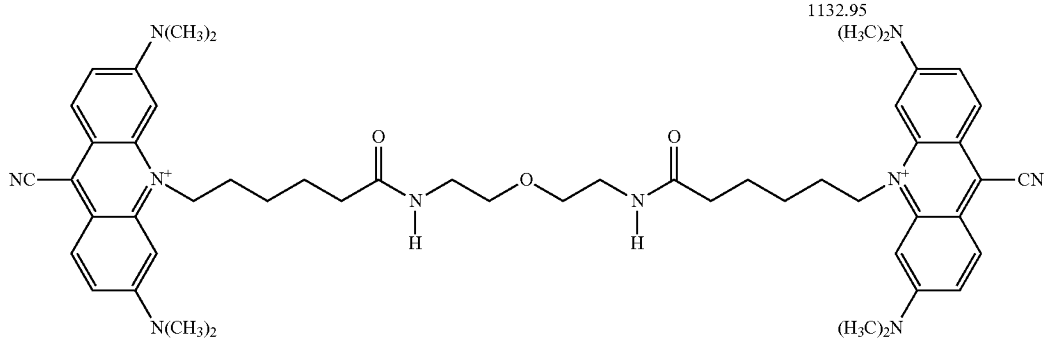 | 1132.95 | 19 |

TABLE 2-continued

Exemplary Fluorescent Nucleic Acid Dyes

| No. | Name | Structure | MWt. | SPACER LENGTH (ATOMS) |
|---|---|---|---|---|
| 23 | AOTO-3 | 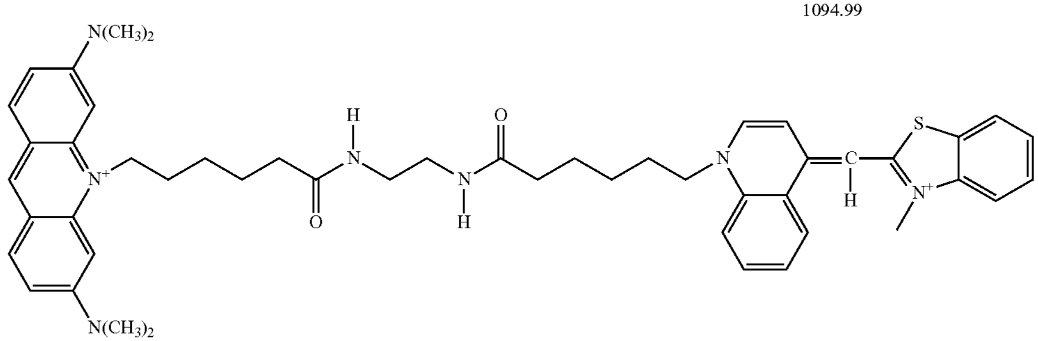 | 1094.99 | 16 |
| 24 | TOTO-12 | 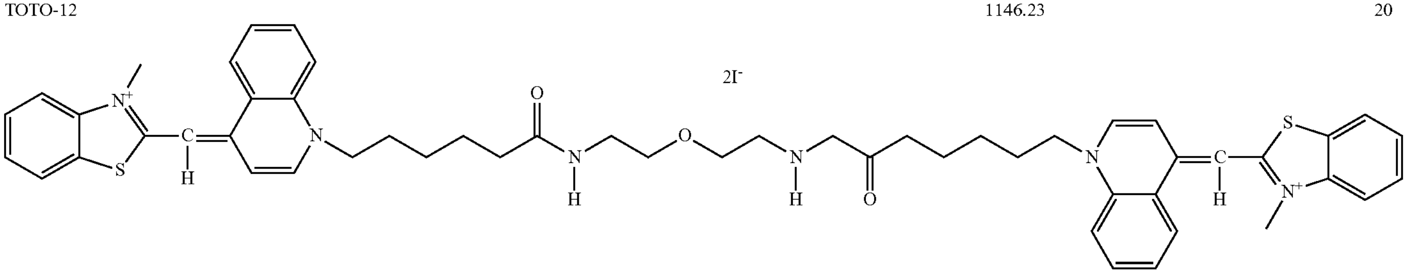 | 1146.23 | 20 |
| 25 | TO(3)TO(3)-12 | 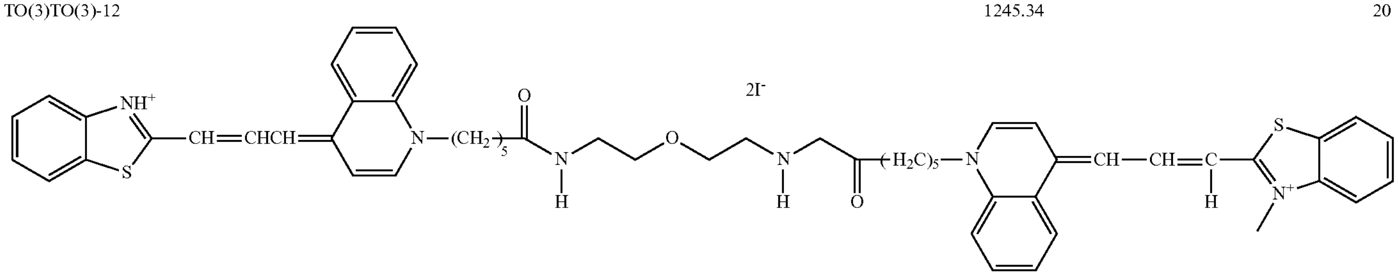 | 1245.34 | 20 |

TABLE 2-continued

Exemplary Fluorescent Nucleic Acid Dyes

| No. | Name | Structure | MWt. | SPACER LENGTH (ATOMS) |
|---|---|---|---|---|
| 26 | TO(3)TO(3)-2 | 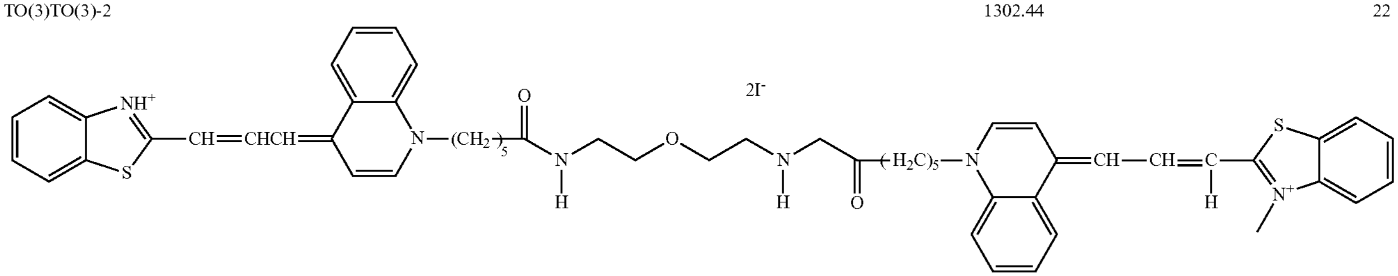 | 1302.44 | 22 |
| 27 | AORO-7 | 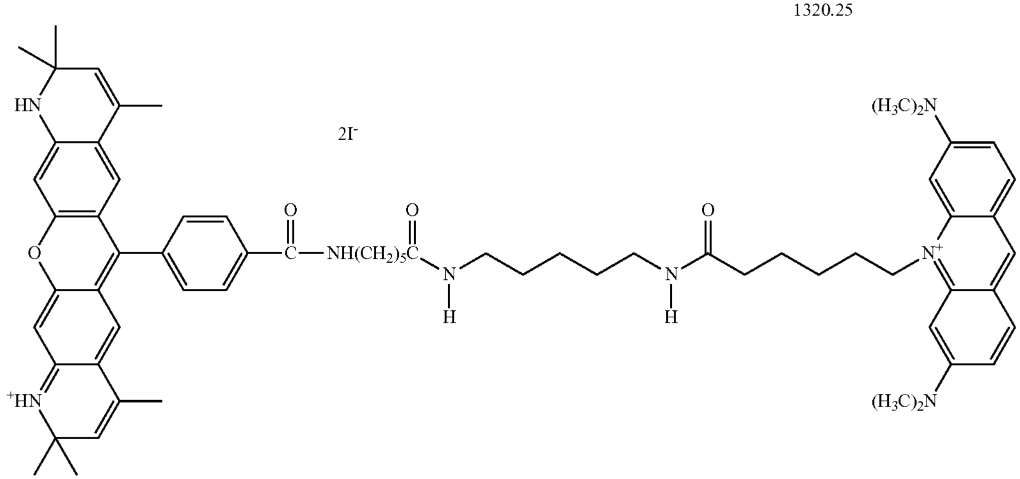 | 1320.25 | 21 |

TABLE 2-continued

Exemplary Fluorescent Nucleic Acid Dyes

| No. | Name | Structure | MWt. | SPACER LENGTH (ATOMS) |
|---|---|---|---|---|
| 28 | RORO-12 | 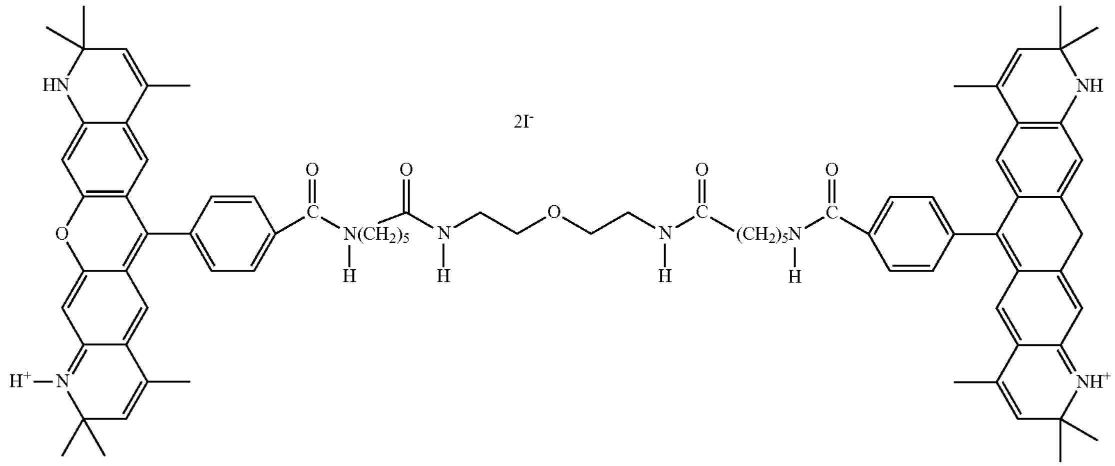 | 1550.51 | 22 |
| 29 | TOTO-13 | 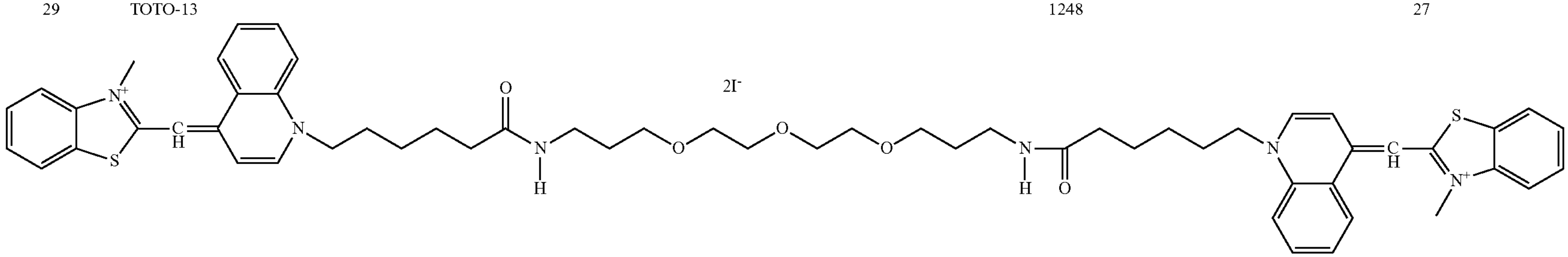 | 1248 | 27 |
| 30 | STST-27 | 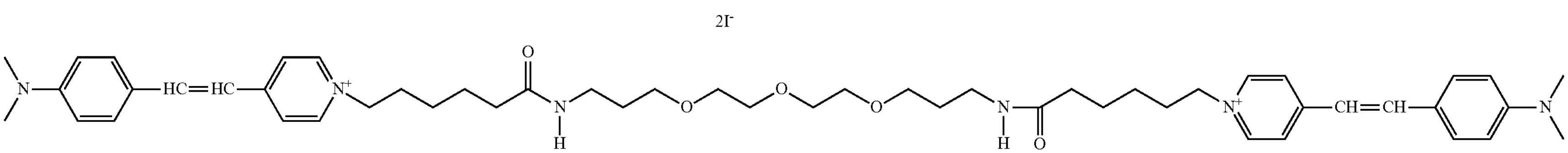 | 1116 | 27 |

TABLE 2-continued
Exemplary Fluorescent Nucleic Acid Dyes
| No. | Name | Structure | MWt. | SPACER LENGTH (ATOMS) |
|---|---|---|---|---|
| 31 | STST-19 | 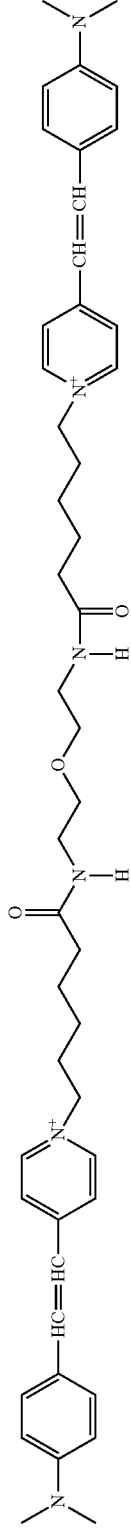 | 1000.8 | 19 |
| 32 | AOAO-47 | 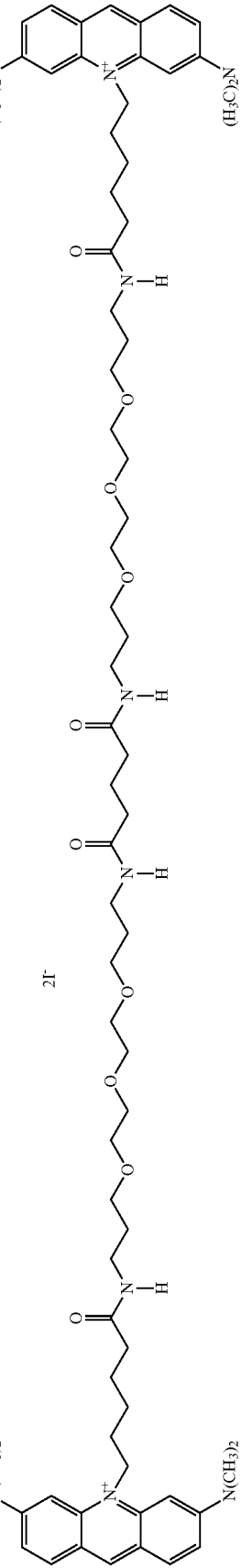 | 1547.6 | 47 |

TABLE 2-continued
Exemplary Fluorescent Nucleic Acid Dyes
| No. | Name | Structure | MWt. | SPACER LENGTH (ATOMS) |
|---|---|---|---|---|
| 33 | AOAO-67 | 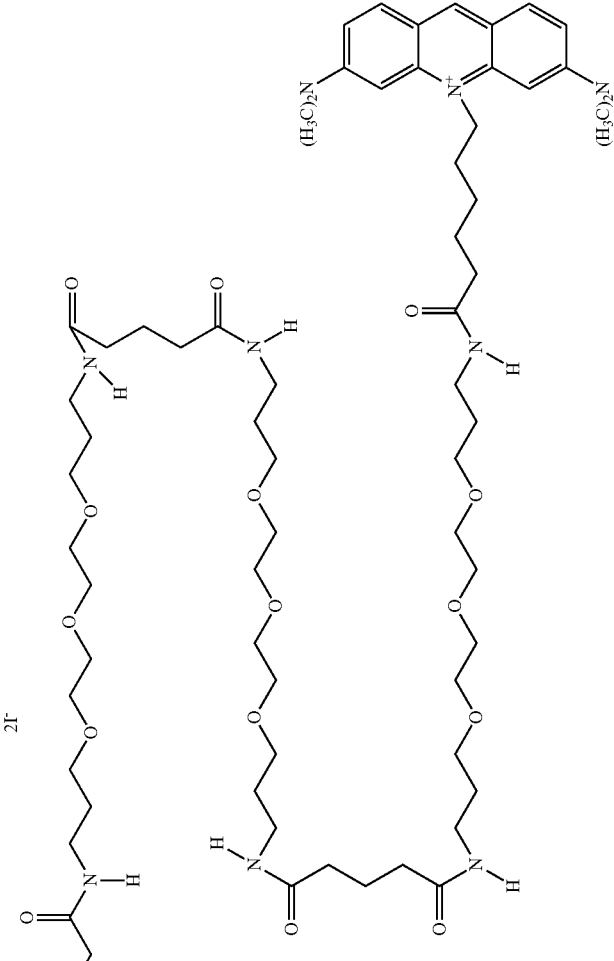 | 1864 | 67 |

TABLE 2-continued

Exemplary Fluorescent Nucleic Acid Dyes

| No. | Name | Structure | MWt. | SPACER LENGTH (ATOMS) |
|---|---|---|---|---|
| 34 | AOAO-113 | 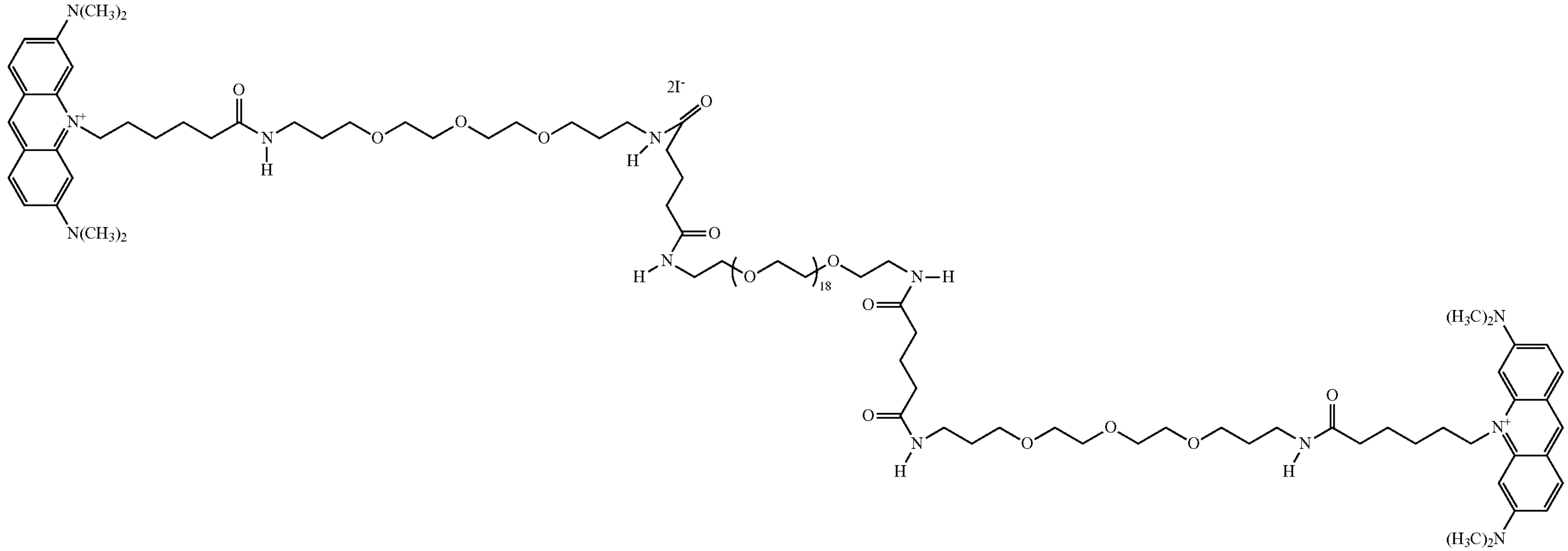 | 2541 | 113 |
| 35 | ET-27 | 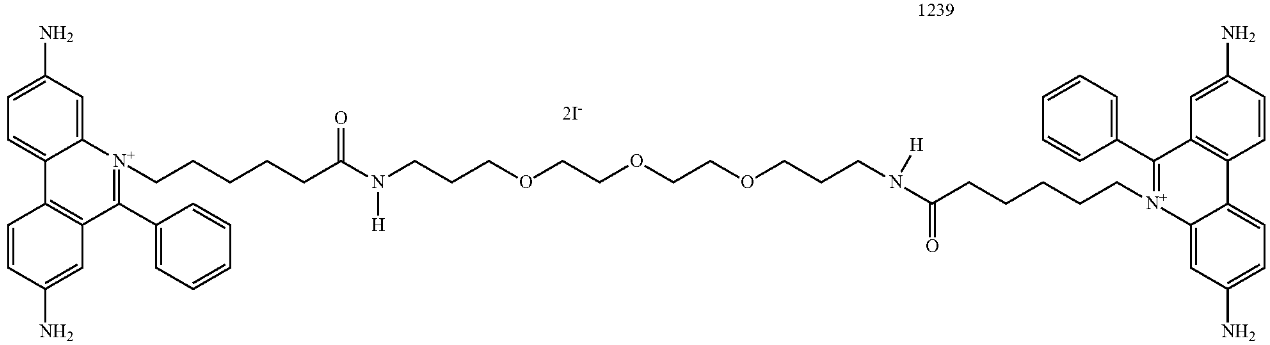 | 1239 | 27 |

TABLE 2-continued
Exemplary Fluorescent Nucleic Acid Dyes
| No. | Name | Structure | MWt. | SPACER LENGTH (ATOMS) |
|---|---|---|---|---|
| 36 | STST-21N | 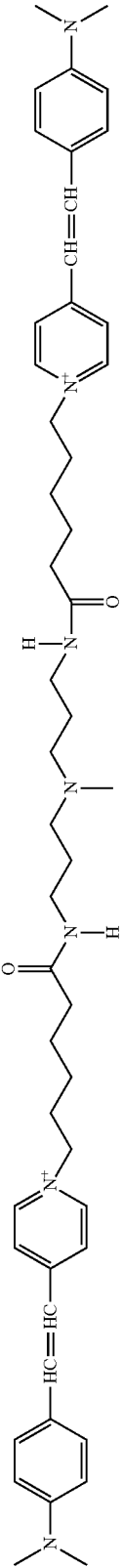 2r | 1041 | 21 |

While many of the structures shown in Table 2 show one or more iodide anion(s), any other appropriate anion(s), such as those described herein, such as chloride anion(s), merely by way of example, may be used in place of the iodide anions shown.

A dimeric dye may comprise a fluorescent nucleic acid dye $Q_1$ and a fluorescent nucleic acid dye $Q_2$, wherein $Q_1$ and $Q_2$ may be the same, or different. A dimeric dye may comprise a pair of identical fluorescent monomeric nucleic acid dyes. When $Q_1$ and $Q_2$ are the same, the resulting dye is a homodimer, such as any of Dye Nos. 6-22, 24-26, and 28-36 of Table 2, merely by way of example. When $Q_1$ and $Q_2$ are different fluorescent nucleic acid dyes that have similar absorption and emission spectra, the resulting dimer is a heterodimer, such as that of Dye No. 23 of Table 2, merely by way of example. Such a heterodimer is functionally similar to a homodimer. In either of the foregoing cases, both $Q_1$ and $Q_2$ are reporter dyes, such that upon DNA binding, they both contribute to the detected fluorescent signal. When $Q_1$ and $Q_2$ are different fluorescent nucleic acid dyes that have substantially different absorption and emission spectra, the resulting dimer is a heterodimer. In this latter case, only one of the two dyes, $Q_1$ and $Q_2$, is selected as a reporter dye.

Fluorescent nucleic acid dyes and examples thereof are now described. Examples of a monomeric fluorescent nucleic acid dye suitable for constructing dimeric dyes include, but are not limited to, an acridine dye, an asymmetric cyanine-based nucleic acid stain, a phenanthridinium dye, a symmetric cyanine nucleic acid stain, a pyronin dye, a styryl dye, a derivative of DAPI, and a derivative of a Hoechst dye. DAPI and Hoechst dyes generally cannot be directly attached to BRIDGE because they do not possess a reactive group for bond formation. In this context, a derivative refers to a base dye, such as DAPI or a Hoechst dye, that is modified sufficiently for bond formation, such as by addition of a reactive group, by way of example.

The monomeric fluorescent nucleic acid dye may be an acridine dye having the general structure (Structure 2) set forth directly below.

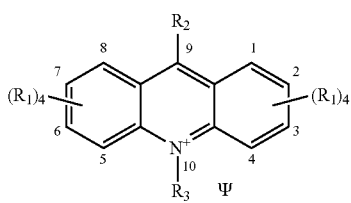

Structure 2

Acridine orange (AO) is an acridine dye that stains dsDNA with green fluorescence and stains RNA with red fluorescence. Traganos, et al., *J. Histochem. Cytochem.* 25(1), 46 (1977). Unlike some other acridine dyes, AO has a high extinction coefficient (>50,000) and a long absorption wavelength ($\lambda_{abs}$=500 nm (DNA bound)). However, the affinity of AO for nucleic acid is very low and the dye has significant intrinsic fluorescence in the absence of nucleic acids. In this regard, the level of intrinsic fluorescence may be significant in that it precludes the dye from being used in detecting nucleic acid at a low level, such as in the low nanogram/mL range, for example, or in detecting nucleic acid in gels without a destaining step, for example. Consequently, AO itself is of little utility for DNA or RNA quantification.

An acridine dye may comprise any of a variety of substituents at various positions on the ring structure. The nature of a substituent and its substitution position may strongly affect the spectral properties of the dye produced. In general, electron-donating substituents at the 3- and 6-positions and an electron-withdrawing substituent at the 9-position typically red-shift the absorption and emission spectra of the dye. Examples of a typical electron-donating group include, but are not limited to, an amino group, a hydroxyl group, an alkoxy group, and an alkylmercapto group. Examples of a typical electron-withdrawing group include, but are not limited to, a cyano group, a perfluoroalkyl group, a carboxamido group, a sulfonamide group, a nitro group, and a halogen group. Any additional ring structure fused with the core structure will also increase the wavelengths of the dye produced.

Various portions of Structure 2 are now described. In Structure 2, as in various other monomeric dye structures provided or described herein, a symbol of "R" followed by a subscript, such as $R_1$, merely by way of example, may indicate a substituent of the structure that is not part of BRIDGE, or may represent where BRIDGE attaches to the structure, in which case, it is not a substituent of the structure. Each $R_1$, independently, may be H; an alkyl or alkenyl having 1 carbon to 6 carbons, inclusive; a halogen; —$OR_4$; —$SR_5$; —$NR_6R_7$; —CN; —NH(C=O)$R_8$; —NHS(=O)$_2R_9$; or —C(=O)NH$R_{10}$; and any adjacent pair of $R_1$s optionally form a 5- or 6-membered saturated or unsaturated ring, which further optionally comprises at least one hetero atom selected from N, O and S. One of the $R_1$s may represent where BRIDGE attaches to the structure, in which case, that $R_1$ is merely representative and not actually a substituent of the monomeric dye. In any case where $R_1$ involves at least one of $R_4$, $R_5$, $R_6$, $R_7$, $R_8$, $R_9$, and $R_{10}$, any applicable one of same is independently H or an alkyl having 1 carbon to 6 carbons, inclusive, and for any applicable pair of adjacent $R_6$ and $R_7$, independently, $R_6$ and $R_7$ may in combination form a 5- or 6-membered saturated or unsaturated ring, which optionally comprises at least one hetero atom selected from N and O.

Typically, $R_2$ is H; an alkyl or alkenyl having 1 carbon to 6 carbons, inclusive; an aryl optionally comprising at least one hetero atom selected from halogens, N, O and S; a halogen; —$OR_{11}$; —$SR_{12}$; —$NHR_{13}$; —CN; or —C(=O)NH$R_{14}$; or represents where BRIDGE attaches to the structure. In any case where $R_2$ involves at least one of $R_{11}$, $R_{12}$, $R_{13}$ and $R_{14}$, any applicable one of same is independently H or alkyl having 1 carbon to 6 carbons, inclusive.

Typically, $R_3$ is H; or an alkyl having 1 carbon to 6 carbons, inclusive; or represents where BRIDGE attaches to the structure.

Ψ is an anion, such as an anion that balances positive charge(s) associated with the dye, for example. Ψ may be biologically compatible. Examples of a suitable anion include, but are not limited to, a halide, a sulfate, a phosphate, a perchlorate, a tetrafluoroborate, and a hexafluorophosphate. Merely by way of example, the anion may be chloride or iodide.

Only one of $R_1$, $R_2$ and $R_3$ must represent where BRIDGE attaches to the structure. Merely by way of example, one of $R_2$ and $R_3$ may represent where BRIDGE attaches to the structure. As described herein, BRIDGE may be covalently linked to a monomeric acridine dye, such as any such dye described herein, and to another suitable monomeric dye, to form a dimeric dye.

The monomeric acridine dye may have the structure (Structure 3) set forth directly below.

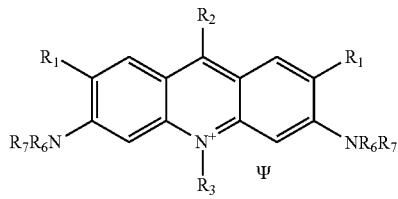

Structure 3

In Structure 3, generally, each $R_1$, independently, is H, or a C1-C2, inclusive, alkyl; one of $R_2$ and $R_3$ represents where BRIDGE attaches to the structure; when $R_2$ represents where BRIDGE attaches to the structure, $R_3$ is H or —$CH_3$; when $R_3$ represents where BRIDGE attaches to the structure, $R_2$ is selected from H, —$CH_3$, —$NH_2$, —$NHCH_3$, —CN, and —C(=O)$NH_2$; each of $R_6$ and $R_7$, independently, is H, or a C1-C2, inclusive, alkyl; and $\Psi$ is an anion, as previously described. Merely by way of example, for each pair of adjacent $R_6$ or $R_7$ and $R_1$, independently, $R_6$ or $R_7$ and $R_1$ may in combination form a 5- or 6-membered, saturated or unsaturated ring. Further, merely by way of example, two monomeric acridine dye molecules of Structure 3 in combination with BRIDGE of Formula 2 may form a dimeric dye.

In one example, the monomeric acridine dye, as represented by Structure 3, may be such that each $R_1$ is H; $R_2$ is H; $R_3$ represents where BRIDGE attaches to the structure; each $R_6$ is —$CH_3$; each $R_7$ is —$CH_3$; and $\Psi$ is an anion, as previously described.

A dimeric dye, such as a dimeric acridine dye, for example, may be useful for detecting nucleic acids immobilized relative to a matrix, such as a solid matrix, a semi-solid matrix, or a gel matrix, for example, or a surface, such as a solid surface, a membrane surface, a glass surface, a plastic surface, or a polysilicon surface, for example. A dimeric acridine dye may be useful for nucleic acid gel staining, such as pre-cast nucleic acid gel staining or post-nucleic acid gel staining. In such an application, there is no need for a de-staining step. In general, nucleic acid gel staining using a dimeric acridine dye is associated with relatively high sensitivity and relatively low background fluorescence. In this regard, sensitivity generally refers to an ability to detect a low level of nucleic acids and low background fluorescence generally refers to an ability to detect nucleic acid presence without having to destain the gel.

The monomeric fluorescent nucleic acid dye may be an asymmetric cyanine dye having the general structure (Structure 4) set forth directly below.

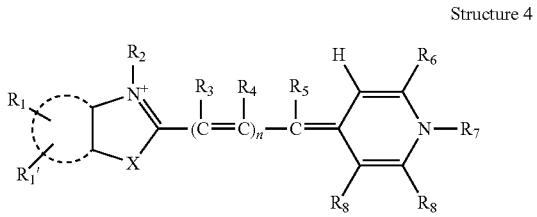

Structure 4

The general structure (Structure 4, above) of an asymmetric cyanine dye may be divided into three parts: 1) a heterocyclic ring that is a substituted benzazolium ring; 2) a methane or polymethine bridge; and 3) a heterocyclic ring that is a substituted pyridinium or quinolinium ring. The dotted line in the structure represents the atoms necessary to form one or more fused aromatic ring(s), optionally incorporating one or more nitrogen(s), which may or may not be quaternized. When the dotted line represents a 6-membered ring comprising one or more nitrogen atom(s), the resulting fused ring is called an aza-benzole ring.

In Structure 4, in general, each of $R_1$ and $R_1'$ on the benzazolium ring, independently, is H; alkyl or alkenyl having 1 carbon to 6 carbons, inclusive; a halogen; —$OR_9$; —$SR_{10}$; —$NR_{11}R_{12}$; —CN; —NH(C=O)$R_{13}$; —NHS(=O)$_2R_{14}$; or —C(=O)$NHR_{15}$. Merely by way of example, one of $R_1$ and $R_1'$ may be a substituent that is meta to X or to the benzazole nitrogen, wherein the substituent confers at least one desirable property as further described below. In any case where $R_1$ or $R_1'$ involves at least one of $R_9$, $R_{10}$, $R_{11}$, $R_{12}$, $R_{13}$, $R_{14}$ and $R_{15}$, any applicable one of same, independently, is H; or alkyl having 1 carbon to 12 carbons, inclusive, optionally incorporating 1 to 2 nitrogen(s), inclusive; or an aryl; and any applicable $R_{11}$ and $R_{12}$ may in combination form a 5- or 6-membered saturated or unsaturated ring, which optionally comprises at least one hetero atom selected from N and O.

As mentioned above, one of $R_1$ and $R_1'$ of Structure 4 may be a substituent that confers at least one desirable property to the dye. One such desirable property is DNA minor groove-binding. A minor groove-binding molecule typically has a structure with a crescent shape that fits into the minor groove of a double-stranded DNA. Examples of a DNA minor groove-binding dye molecule or non-dye molecule, which may include a natural molecule, include, but are not limited to, DAPI, a Hoechst dye, distamycin A, netropsin, and any of numerous synthetic minor groove-binders based on polyamides of N-methylpyrrole and N-methylimidazole. Catalog of Biotium, Inc. (Hayward, Calif. (CA)), 2005-2006; Boger, et al., *Acc. Chem. Res.* 37, 61 (2004); and Dervan, P. B., *Bioorg. & Med. Chem.* 9, 2215 (2001). The crescent shape of a minor groove-binder is typically created by meta-substitution of a 5- or 6-membered ring with a minor groove-binder substituent, which includes, but is not limited to, a substituted or an unsubstituted benzoxazol-2-yl, a substituted or an unsubstituted benzimidazol-2-yl, a substituted or an unsubstituted benzothiazol-2-yl, a substituted or an unsubstituted imidazol-2-yl, a substituted or an unsubstituted oxazol-2-yl, a substituted or an unsubstituted thiazol-2-yl, a substituted or an unsubstituted N-methylpyrrolyl-2-aminocarbonyl, a substituted or an unsubstituted N-methylpyrrolyl-3-carboxamido, a substituted or an unsubstituted 1-methylimidazol-2-carboxamido, a substituted or an unsubstituted 1-methylimidazol-4-aminocarbonyl, a substituted or an unsubstituted phenyl, a substituted or an unsubstituted pyridyl, a substituted or an unsubstituted pyrazinyl, and a substituted or an unsubstituted triazinyl. A DNA dye may be meta-substituted by a minor groove-binder substituent as described in U.S. Patent Application Publication No. 2004/0132046.

One of $R_1$ and $R_1'$ may represent where BRIDGE attaches to the structure.

X is selected from O and S. In general, a dye wherein X is S has longer absorption and emission wavelengths than a similar dye wherein X is O.

$R_2$ may be methyl or ethyl, or may represent wherein BRIDGE attaches to the structure. Merely by way of example, $R_2$ may be methyl or ethyl.

The subscript n represents a number of double bond units in any methine bridge and is selected from 0, 1, and 2. Typically, a dye with a longer methine bridge will have longer wavelengths than a dye with a shorter methine bridge. Merely by way of example, n may be 0 or 1.

Substitutents $R_3$, $R_4$, and $R_5$ are independently H or —$CH_3$. Optionally, any adjacent pair of these substitutents may form a 5- or 6-membered ring. Merely by way of example, $R_3$, $R_4$, and $R_5$ may be H.

Independently, each of substituents $R_6$, $R_8$, and $R_8'$ may be H; an alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or unsubstituted aryl, optionally comprising 1 to 3 hetero atom(s), inclusive, selected from halogens, N, O, and S. $R_8$ and $R_8'$ may in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen. In any case in which any of $R_6$, $R_8$, and $R_8'$ involve at least one of $R_{16}$ and $R_{17}$, any applicable one of same, independently, is H; or alkyl having 1 carbon to 12 carbons, inclusive, optionally incorporating 1 to 2 nitrogen(s), inclusive; or an aryl; and any applicable $R_{16}$ and $R_{17}$ may in combination form a 5- or 6-membered saturated or unsaturated ring, which optionally comprises at least one hetero atom selected from N and O.

$R_6$ may represent where BRIDGE attaches to the structure. $R_7$ is selected from H; an alkyl or alkenyl having 1 carbon to 10 carbons, inclusive, optionally comprising an aryl and at least one hetero atom selected from N, O, and S; or a substituted or unsubstituted aryl optionally comprising 1 to 3 hetero atom(s), inclusive, selected from halogens, N, O, and S; or may represent where BRIDGE attaches to the structure.

Ψ is an anion, as previously described herein.

Only one of $R_1$, $R_1'$, $R_6$, $R_7$ and $R_8$ must represent where BRIDGE attaches to the structure. As described herein, BRIDGE may be covalently linked to a monomeric asymmetric cyanine dye, such as any such dye described herein, and to another suitable monomeric dye, to form a dimeric dye.

An asymmetric cyanine dye may have the structure (Structure 5) set forth directly below, wherein each of $R_1'$, $R_6$, $R_7$, $R_8$ and $R_8'$ is as previously described in connection with Structure 4.

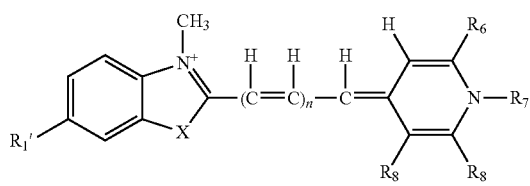

Structure 5

By way of example, the asymmetric cyanine dye, as represented by Structure 5, may be such that $R_1'$ is H; alkyl or alkenyl having 1 carbon to 6 carbons, inclusive; a halogen; —$OR_9$; —$SR_{10}$; —$NR_{11}R_{12}$; —CN; —$NH(C=O)R_{13}$; —$NHS(=O)_2R_{14}$; —$C(=O)NHR_{15}$; or a substituent associated with minor groove binding; or represents where BRIDGE attaches to the structure. Further, when $R_1'$ comprises at least one of $R_9$, $R_{10}$, $R_{11}$, $R_{12}$, $R_{13}$, $R_{14}$ and $R_{15}$, any said one of $R_9$, $R_{10}$, $R_{11}$, $R_{12}$, $R_{13}$, $R_{14}$ and $R_{15}$, independently, is H or alkyl having 1 carbon to 12 carbons, inclusive, optionally incorporating 1 to 2 nitrogen(s), inclusive, or an aryl; and when $R_1'$ comprises $R_{11}$ and $R_{12}$, $R_{11}$ and $R_{12}$ may in combination form a 5- or 6-membered, saturated or unsaturated ring, which optionally comprises at least one hetero atom selected from N and O. X may be selected from O and S and n may be selected from 0, 1, and 2. $R_6$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from halogens, N, O, and S; or may represent where BRIDGE attaches to the structure. $R_7$ may be H; alkyl or alkenyl having 1 carbon to 10 carbons, inclusive, optionally comprising an aryl and at least one hetero atom selected from N, O, and S; or a substituted or an unsubstituted aryl optionally comprising 1 to 3 hetero atom(s), inclusive, selected from halogens, N, O, and S; or may represent where BRIDGE attaches to the structure. $R_8$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from halogens, N, O, and S; or may represent where BRIDGE attaches to the structure. $R_8'$ may be H; alkyl or alkenyl having 1 carbon to 10 carbons, inclusive, optionally comprising at least one hetero atom selected from N, O, and S; a halogen; —$OR_{16}$; —$SR_{16}$; —$NR_{16}R_{17}$; or a substituted or an unsubstituted aryl, optionally comprising 1 to 3 hetero atom(s), inclusive, selected from halogens, N, O, and S. $R_8$ and $R_8'$ may in combination form a fused aromatic ring, which may be further substituted 1 to 4 time(s), inclusive, independently, by C1-C2, inclusive, alkyl, C1-C2, inclusive, alkoxy, C1-C2, inclusive, alkylmercapto, or a halogen. For any $R_6$, $R_8$, or $R_8'$ that comprises at least one of $R_{16}$ and $R_{17}$, any said one of $R_{16}$ and $R_{17}$ thereof, independently, may be H; alkyl having 1 carbon to 12 carbons, inclusive, optionally incorporating 1 to 2 nitrogen(s) or an aryl. For any $R_6$, $R_8$, and $R_8'$ that comprises $R_{16}$ and $R_{17}$, $R_{16}$ and $R_{17}$ thereof may in combination form a 5- or 6-membered saturated or unsaturated ring, which optionally comprises at least one hetero atom selected from N and O. Only one of $R_1'$, $R_6$, $R_7$ and $R_8$ represents where BRIDGE attaches to the structure. Ψ is an anion, as previously described.

An asymmetric cyanine dye may have the structure (Structure 6) set forth directly below, wherein $R_7$ represents where BRIDGE attaches to the structure and Ψ is an anion, as previously described.

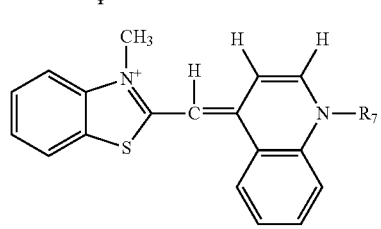

Structure 6

Merely by way of example, two monomeric asymmetric cyanine dye molecules of Structure 6 in combination with BRIDGE of Formula 2 may form a dimeric dye.

A dimeric asymmetric cyanine dye may be useful for detecting nucleic acids immobilized relative to a matrix or a surface, as previously described in connection with another dye, or the like, and for nucleic acid gel staining, such as pre-cast nucleic acid gel staining or post nucleic acid gel staining. In general, nucleic acid gel staining using a dimeric cyanine dye is associated with high sensitivity and low background fluorescence. In such an application, there is no need for a de-staining step. Unlike SYBR Green 1, Dye No. 20 of Table 2 is relatively stable is in buffers that are commonly used in connection gel electrophoresis, such as TBE, at room temperature for about 3 months or more.

A dimeric asymmetric cyanine dye comprising monomeric asymmetric cyanine dyes of Structure 6 may be excited by UV light or by visible light, such as the blue light equipped in a Dark Reader transilluminator from Clare Chemical Research (Dolores, Colo.) and a 488 nm argon laser equipped in some of the commercial laser-based gel scanners, for example. Relatively new gel readers, such as the Dark Reader transilluminator, which use a visible light source, have been developed as a safer alternative to traditional UV light-based transilluminators. These alternative gel readers may employ a blue light with a peak centered around 470 nm. There are also gel readers that use light from 488 nm argon lasers. A gel stain must absorb light sufficiently within a wavelength range of 460-510 nm, inclusive, in order to be read using the various visible light-based gel readers. As such, a gel stained with EB cannot be read using a visible light-based gel reader because the absorption peak of EB is not within the appropriate wavelength range. Dye No. 29 of Table 2 has a very strong and broad absorption or excitation peak centered around 500 nm.

The monomeric fluorescent nucleic acid dye may be a phenanthridinium derivative, having the general structure (Structure 7) set forth directly below.

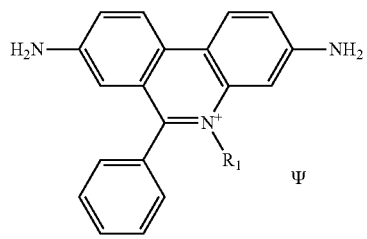

Structure 7

In general, $R_1$ may represent where BRIDGE attaches to the structure, although it will be understood that many variations of Structure 7 above are possible and contemplated herein, via a variety of techniques, such as synthesis techniques that may provide for the attachment of BRIDGE to the structure elsewhere or that may modify the structure to provide a dye with any of various desirable wavelengths. $\Psi$ is an anion, as previously described.

Merely by way of example, two monomeric phenanthridinium dye molecules of Structure 7 in combination with BRIDGE of Formula 2 may form a dimeric dye.

A dimeric phenanthridinium dye may be useful for detecting nucleic acids immobilized relative to a matrix or a surface, as previously described in relation to another dye, or the like, and for nucleic acid gel staining, such as pre-cast nucleic acid gel staining or post-nucleic acid gel staining. In general, nucleic acid gel staining using a dimeric phenanthridinium dye is associated with high sensitivity and low background fluorescence. In such an application, there is no need for a de-staining step.

A dimeric phenanthridinium dye may be relatively stable, even exceptionally so, relative to an SYBR dye, such as those mentioned herein, which may be relatively unstable. Dye No. 35 is generally stable in an electrophoresis buffer, such as a lithium borate buffer, at room temperature for at least about 6 months. Further, this dye in TBE buffer may be heated in a microwave oven for at least about 10 minutes without decomposition.

In a gel electrophoresis application, an agarose gel may be prepared by heating (via microwave, for example) a suspension of agarose powder in an electrophoresis buffer, such as lithium borate buffer, thereby producing a hot agarose solution, pouring the solution onto a slab, and cooling the solution, thereby producing a useful gel. In a pre-cast gel staining application, an EB dye may be added directly to the agarose powder suspension prior to the heating of the suspension, as EB is generally sufficiently stable, both hydrolytically and thermally. This is generally not the case with a SYBR Green dye, as such a dye is generally of limited hydrolytic and thermal stability. For example, in a pre-cast gel staining application, SYBR Green I dye is generally combined with an agarose solution after the initial agarose suspension has been heated and the resulting agarose solution has been cooled as much as possible. Combining the SYBR Green I dye with the agarose solution in this manner may be a delicate task, as if the temperature of the agarose solution is too high, the dye my decompose, and if the temperature of the agarose solution is too low, the agarose solution may gel up such that the dye and the solution are inadequately combined or mixed. Further by way of example, in a pre-cast gel staining application, a pre-cast gel prepared with SYBR Green I is generally used within 24 hours, as it may lose utility thereafter. As SYBR Gold is even less stable than SYBR Green, it generally cannot be used to make a precast gel. Dye No. 35 of Table 2 is of sufficient hydrolytic and thermal stability to be used in the preparation of a pre-cast gel, such as a pre-cast gel that may be stored for at least about 3 months without loss of performance, for example. This dye may offer sufficient to exceptional stability, as well as low or minimal background fluorescence relative to EB and low or minimal toxicity relative to EB, as further described below.

The monomeric fluorescent nucleic acid dye may be a xanthene derivative, having the general structure (Structure 8) set forth directly below.

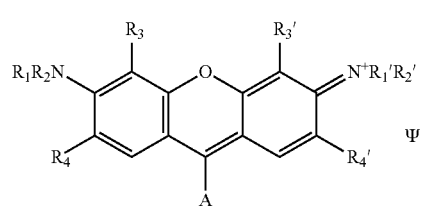

Structure 8

Certain cationically charged xanthene dyes are known to bind to nucleic acids. For example, pyronin Y, in which $R_1$, $R_2$, $R_1'$, and $R_2'$ are methyl and $R_3$, $R_3'$, $R_4$, $R_4'$, and A are H, is a known fluorescent DNA binding dye that has been used for DNA gel staining. Adkin et al., *Anal. Biochem.* 240(1), 17(1996). A dye having the general skeleton shown in Structure 8 above is expected to have similar nucleic acid staining properties and to provide other fluorescent colors. For example, pyronin Y has an absorption maximum at 548 nm and an emission maximum at 565 nm, providing a red fluorescent color.

Merely by way of example, in general, each of $R_1$, $R_2$, $R_1'$, and $R_2'$, independently, may be H, or C1-C6, inclusive, alkyl, optionally incorporating 1 to 2 hetero atom(s) selected from N and O. Further merely by way of example, independently, at least one of the pair $R_1$ and $R_2$ and the pair $R_1'$ and $R_2'$ may in combination form a 5- or 6-membered ring, optionally comprising one hetero atom selected from N and O. $R_1$ and $R_1'$ may be the same and $R_2$ and $R_2'$ may be the same.

One of $R_1$, $R_2$, $R_1'$, and $R_2'$ may represent where BRIDGE attaches to the structure. It may be that one of $R_1$, $R_2$, $R_1'$, $R_2'$ and A may represent where BRIDGE attaches to the structure.

Merely by way of example, $R_3$, $R_3'$, $R_4$, and $R_4'$, independently, may be H or C1-C3, inclusive, alkyl. $R_3$, $R_3'$, $R_4$, and $R_4'$ may be the same. Independently, at least one of the pair $R_3$ and $R_1$, the pair $R_2$ and $R_4$, the pair $R_3'$ and $R_1'$, and the pair $R_4$ and $R_2'$ may in combination form a 5- or 6-membered ring, which may be saturated or unsaturated, substituted or unsubstituted.

A is a C1-C3, inclusive, alkyl, or represents where BRIDGE attaches to the structure.

Ψ is an anion, as previously described.

Two monomeric xanthene dye molecules of Structure 8 in combination with BRIDGE of Formula 2 may form a dimeric dye.

Other monomeric fluorescent nuclei acid stains, such as DAPI, DIPI, a Hoechst dye, LDS 751, hydroxystilbamidine, a styryl dye, a merocyanine dye, a cyanine dye, or FluoroGold, merely by way of example, may be suitable for use or may be derivatized to be suitable for use as described herein. Haugland, R. P., *Handbook of Fluorescent Probes and Research Products*, 9$^{th}$ edition. It will be understood that a large number of other monomeric nucleic acid dyes may be suitable for use or may be derivatized to be suitable for use as described herein. The dyes may either be directly conjugated to BRIDGE or be derivatized so that they can be conjugated to BRIDGE using synthesis knowledge.

Dimeric nucleic acid dyes may be useful for detecting nucleic acids immobilized relative to a matrix or a surface, as previously described herein in connection with various dyes, or as nucleic acid gel stains.

There are generally two methods for staining nucleic acids in gels using a fluorescent nucleic acid dye. The first method is post-gel staining, wherein a nucleic acid sample is separated by gel electrophoresis, the gel comprising the separated nucleic acids is bathed in a solution comprising the dye, the gel may be destained, if desirable or necessary to remove background fluorescence, and the resulting gel is viewed and/or documented using a transilluminator and/or a photographing device. The second method is pre-cast gel staining, wherein a gel is premixed or pre-embedded with the dye, the nucleic acid sample is separated by electrophoresis using the pre-cast gel, and the stained gel is viewed and/or documented using a transilluminator and/or a photographing device. In general, a dimeric nucleic acid dye can be used for post-gel staining, pre-cast gel staining, or variations thereof. As such a dye is generally associated with low background fluorescence, destaining is usually not required.

Post-nucleic acid gel staining may be carried out using a dimeric nucleic acid dye. Generally, post-nucleic acid gel staining may comprise preparation of a gel, electrophoretic separation of a nucleic acid sample, preparation of a dye solution, staining of the gel comprising separated nucleic acid molecules, and/or visualization of the stained gel, as now generally described.

The gel may be prepared by a known method or any appropriate method. The gel may be an agarose gel, a polyacrylamide gel, or the like. In general, the density of a gel, which is determined by the amount of agarose or acylamide monomer per volume unit, affects DNA migration, and thus separation of DNA bands. By way of example, for suitable or optimal DNA band resolution, a gel with a relatively lower percentage of agarose, such as 0.3-0.7% (weight/volume), may be used for relatively longer DNA samples, such as DNA of 5-60 kb. Further by way of example, a gel with a relatively higher percentage of agarose, such as 1.5-3% (weight/volume), may be used for relatively shorter DNA fragments, such as DNA of 0.1 to 1 kb. In general, an agarose gel comprising about 1% of agarose may be used for separating DNA of relatively common lengths or sizes, such as from about 0.5 to about 6 kb.

A nucleic acid sample may be prepared, loaded onto a gel, and then separated by electrophoresis. The process may involve the preparation of a dye stock solution. A dye stock solution may be prepared by dissolving a solid dimeric dye in an aqueous solvent, such as water or a buffer or a water-miscible organic solvent, such as DMSO or DMF. In general, the concentration of the stock solution is about 100-fold to about 10,000-fold greater relative to the concentration of a working dye solution. The working dye solution may be prepared by diluting the dye stock solution to an effective dye concentration with an aqueous solvent selected from water; a solution of at least one salt that comprises an anion that is associated with a strong acid and a cation that is associated with a strong base, such as a salt previously described herein, for example; and a buffer selected from phosphate buffered saline (PBS), tris acetate (TAE), and tris borate (TBE); and any combination thereof. Merely by way of example, the dye stock solution may be so diluted in an aqueous solution comprising a salt that comprises an anion that is associated with a strong acid and a cation that is associated with a strong base. Examples of such a salt include, but are not limited to, sodium chloride, sodium bromide, sodium sulfate, potassium chloride, potassium bromide, potassium sulfate, magnesium choride, and tetramethylammonium chloride. In such a case, the salt concentration may be from about 5 mM to about 0.5 M, inclusive, about 0.05 M to about 0.2 M, inclusive, or about 0.1 M. In general, an effective working concentration of the dye is from about 0.1 μM to about 100 μM, inclusive, or from about 0.5 μM to about 10 μM, inclusive.

The gel and the working dye solution may be placed in contact in an appropriate manner, such as by immersing the gel in the working dye solution for a sufficient amount of time, such as from about 10 to about 90 minutes, inclusive, or about 30 minutes. Once the gel is stained by the working dye solution, the stained gel may be illuminated with a light of suitable wavelength to generate a fluorescence signal. Equipment useful for illuminating a stained gel includes, but is not limited to, a UV transilluminator, a laser scanner, a Dark Reader from Clare Chemical Research, Inc. (Dolores, Colo.), or the like, merely by way of example. The fluorescence signal may be detected in any appropriate manner, such as via visual inspection, a camera, a photographic film, or the like, merely by way of example.

Pre-cast nucleic acid gel staining may be carried out using a dimeric nucleic acid dye. Generally, this pre-cast nucleic acid gel staining may comprise preparation and casting of a stained gel, electrophoretic separation of a nucleic acid sample, and/or visualization of the stained gel, as now generally described.

A gel solution comprising a dimeric dye may be prepared in various ways. A dye stock solution may be prepared as generally described above in relation to post-gel staining. In one example, a gel solution comprising a dimeric dye may be prepared by combining or mixing an aliquot of the dye stock solution with a suitable amount of agarose powder in an electrophoresis buffer, such as lithium borate buffer, and heating the resulting solution under conditions suitable for producing an approximately homogeneous gel solution, such as via a microwave oven, for example, at a suitable setting or temperature, for example, and for a sufficient amount of time, such as a few minutes, for example. In another example, a gel solution comprising a dimeric dye may be prepared by preparing an agarose gel solution as just described, but without the dye, and combining or mixing the resulting solution with an aliquot of the dye stock solution sufficient to provide an effective working concentration of the dye. In either example or any suitable preparation, the effective working concentration of the dye in the gel solution may generally be from about 0.1 µM to about 100 µM, inclusive, or from about 0.5 µM to about 10 µM, inclusive. Further, in either example or any suitable preparation, the amount of agarose in the gel solution may generally be from about 0.5% to about 8%, inclusive. Other gel solutions, such as gel solutions comprising a suitable component other than agarose, may be similarly prepared.

A gel may be cast using the heated gel solution. A nucleic acid sample may be prepared, loaded onto the gel, and then electrophoretically separated in a known manner or any appropriate manner. The gel comprising the separated nucleic acid sample may be illuminated in any appropriate manner to generate a fluorescence signal, which may then be detected or visualized in any appropriate manner, such as that generally described above in connection with post-gel staining.

Any suitable variation of the above-described nucleic acid detection schemes may be employed and is contemplated herein. Merely by way of example, a nucleic acid sample to be detected may be present and/or immobilized in a sieving matrix, in a sedimentation or buoyant density gradient, on an inert matrix such as a blot, on a testing strip, on any other solid or semi-solid support, or the like.

A post-gel staining solution may comprise an aqueous solution that comprises a nucleic acid stain and at least one salt that comprises an anion that is associated with a strong acid and a cation that is associated with a strong base. The concentration of the stain relative to the solution may be from about 0.1 µM to about 100 µM, inclusive, or from about 0.5 µM to about 10 µM, inclusive, for example. The stain or dye component may be any useful staining dye, such as a monomeric or dimeric nucleic acid dye, merely by way of example. The salt may have a concentration of from about 5 mM to about 0.5 M, inclusive, about 0.05 M to about 0.2 M, inclusive, or about 0.1 M, for example. The salt component may enhance, perhaps significantly so, the staining quality of a post-nucleic acid staining solution. The salt may be selected from the sodium chloride, sodium bromide, sodium sulfate, potassium chloride, potassium bromide, potassium sulfate, tetramethylammonium chloride, and/or magnesium chloride for example. The aqueous solution may further comprise, optionally, a buffer.

A post-gel staining solution comprising a salt that comprises an anion that is associated with a strong acid and a cation that is associated with a strong base provides better results in a nucleic acid gel-staining application than does a post-gel staining solution that comprises a buffer, but no such salt. This holds true when the post-gel staining solution comprises a dimeric nucleic acid dye, such as those described herein, or a monomeric nucleic acid dye, such as an asymmetric cyanine nucleic acid dye, such as SYBR Green I, SYBR Safe, SYBR Gold and GelStar, merely by way of example.

A dimeric nucleic acid dye may be included in a kit. A kit may comprise the dye, information or a protocol regarding use of the dye or the kit, and/or other useful or necessary materials or reagents, such as any materials or reagents suitable for the detection of nucleic acids, for example, such as a buffer, a DNA or RNA ladder, and/or agarose, for example. A kit may comprise the dye impregnated into paper, such as paper provided by Edvotek (Bethesda, Md.) or disclosed in European Patent Office Publication No. EP 1 057 001 A2 or World Intellectual Property Organization International Publication No. WO 99/42620.

A dimeric nucleic acid dye may be synthesized via synthesis of monomeric dye constituents, synthesis of BRIDGE, and conjugation of the monomeric dye constituents to BRIDGE. Syntheses of monomeric dyes and monomeric dyes comprising a functional group or a reactive group are now described.

Suitable monomeric dyes and monomeric dyes comprising a functional group or a reactive group may be prepared from scratch by a known procedure or any suitable procedure, or by modifying commercially available material that already has a suitable or desirable core structure. Many monomeric acridine dyes may be prepared from commercially available acridine dyes. A few examples of a commercially available acridine dye that may serve as suitable starting material for synthesis are set forth directly below.

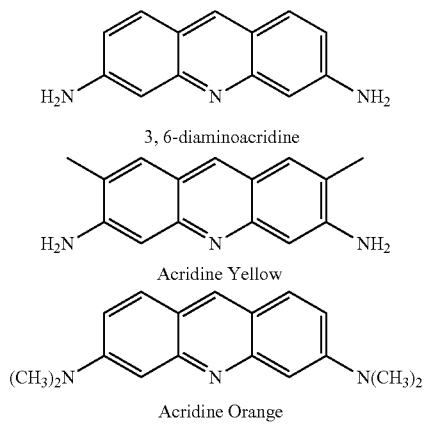

Other acridine core structures may be prepared according to known procedures or any suitable procedures. Albert, A., *The acridines: their preparation, physical, chemical, and biological properties and uses*, Edward Arnold Ltd., London; Eldho, et al., *Synth. Commun.* 29, 4007 (1999); and Joseph, et al., *Bioconjugate Chem.* 15, 1230 (2004). An acridine core structure may be formed by condensing a suitable diphenylamine with a suitable carboxylic acid or a carboxylic acid equivalent in the presence of a Lewis acid, as schematically illustrated in Reaction 1 directly below.

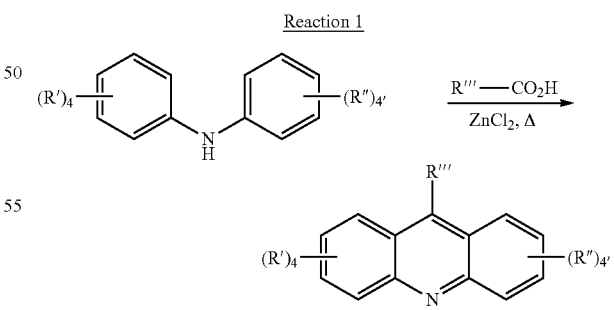

In Reaction 1, R', R" and R''' are suitable substituents, as further described below. The diphenylamine starting material is either commercially available or may be synthesized from a suitable arylhalide and a suitable arylamine using a known method or any suitable method. Yang, et al., *J. Organomet. Chem.* 576, 125 (1999); Hartwig, et al., *J. Org. Chem.* 64, 5575 (1999); and Wolfe, et al., *J. Org. Chem.* 65, 1158 (2000).

The nature of the substituents and the position where the substituents are attached may have a profound effect on the spectral property of the dye. In general, electron-donating groups at the 2-, 3-, 6- and 7-positions will increase the absorption and emission wavelengths of the dye. A typical electron-donating group may be an amino group, an alkylamino group, a dialkylamino group, a hydroxyl group, an alkoxy group, a thiol group, or an alkylthio group, by way of example. A more typical electron-donating group may be an amino group, an alkylamino group, a dialkylamino group, or an alkoxy group, by way of example. In general, an electron-withdrawing group at the 9-position will increase the absorption and emission wavelengths of the dye. A typical electron-withdrawing group may be a cyano group, a perfluoroalkyl group, an aminocarbonyl group, an alkylaminocarbonyl group, an alkylcarbonyl group, an aldehyde group, an alkoxycarbonyl group, an aminosulfonato group, an alkylaminosulfonato group, or a halide group, by way of example. A more typical electron-withdrawing group may be a cyano group, a perfluoroalkyl group, or a halide group.

In general, once the acridine core structure is built, the 10-nitrogen is alkylated with a haloalkyl group, which typically comprises an additional reactive group or a functional group that can be converted to a reactive group. The additional reactive group serves to conjugate the acridine dye to BRIDGE. Several ways of making monomeric acridine orange dyes with a suitable reactive group are schematically illustrated in Scheme 1 directly below.

Scheme 1

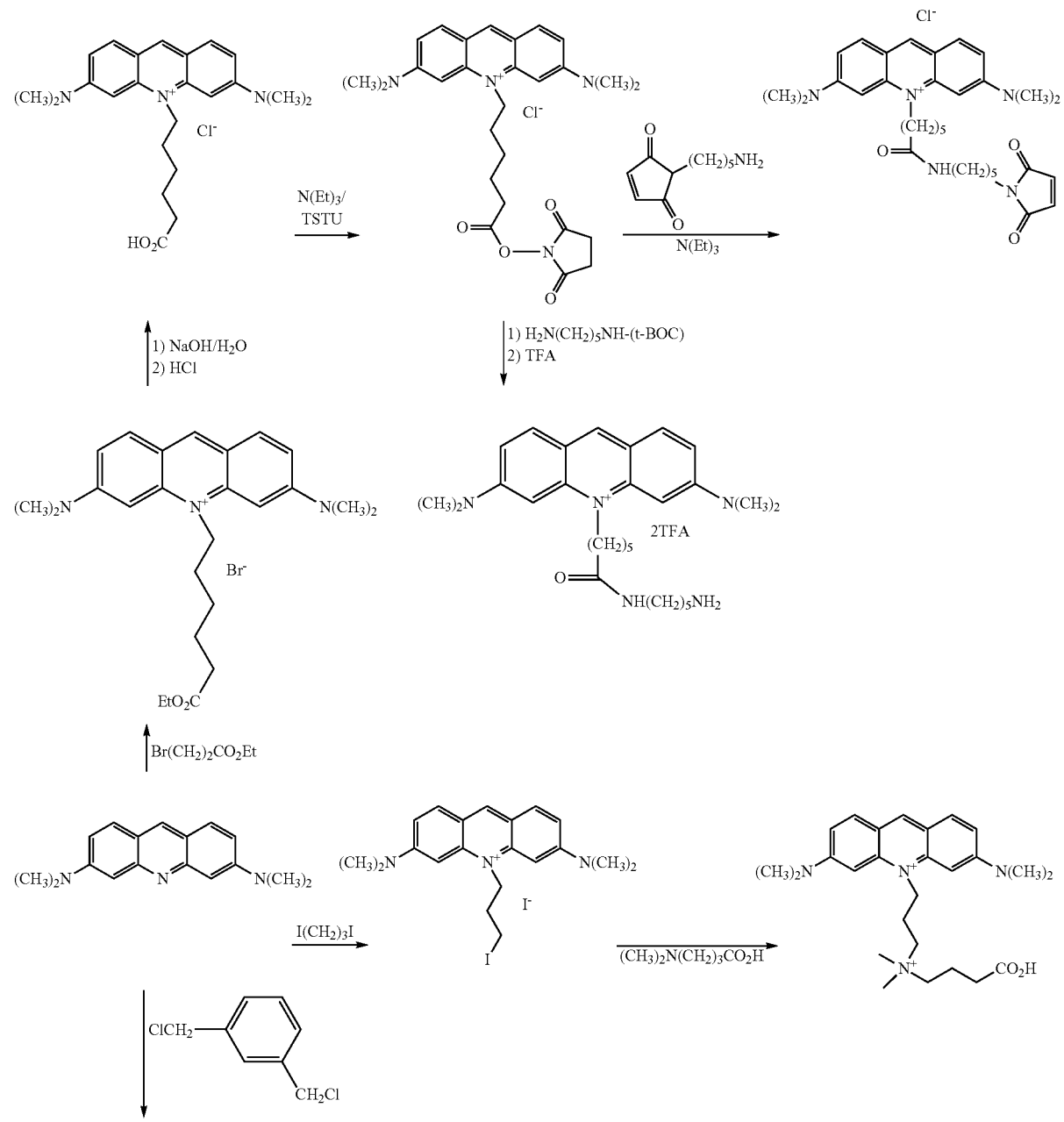

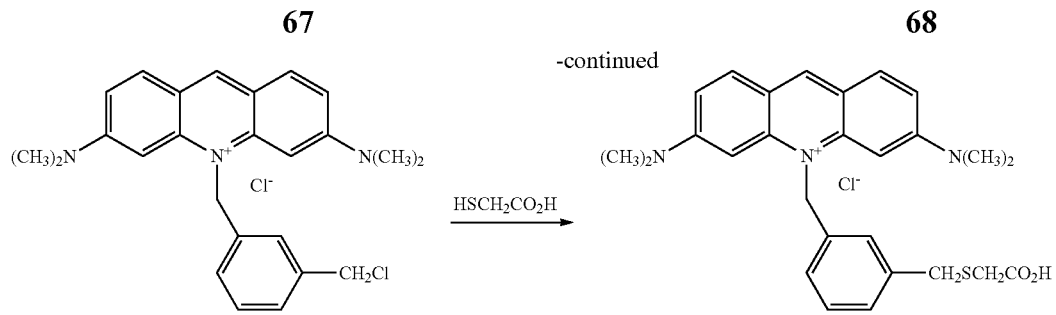

The 9-position of 10-alkylated acridine may be substituted with a cyano group, which may be further hydrolyzed to a carboxamide group, as schematically illustrated in Scheme 2 directly below.

Scheme 2

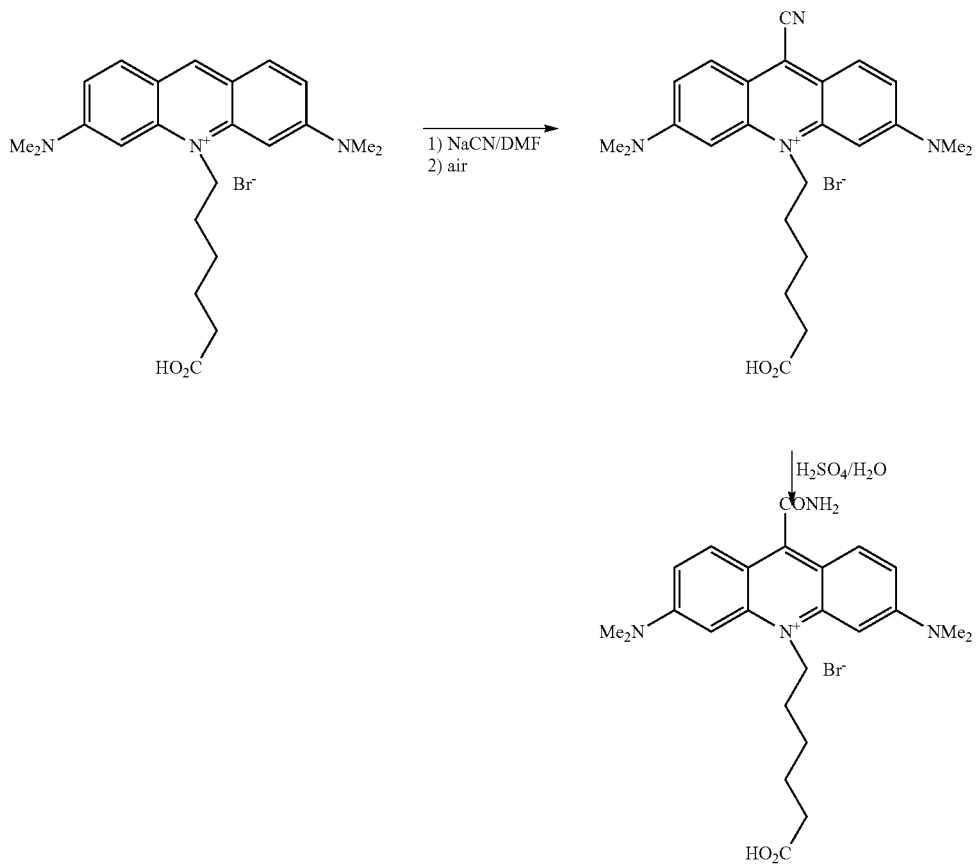

Methods of preparing reactive monomeric asymmetric cyanine dyes have been described. Carreon, et al., *Org. Lett.* 6(4), 517 (2004). Such a dye may have the structure (Structure 9) set forth directly below.

Structure 9

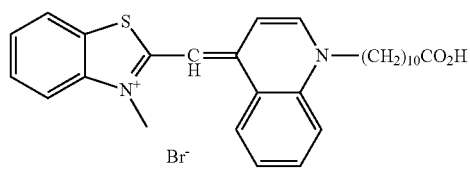

U.S. Pat. No. 5,863,753 discloses the preparation of a series of reactive asymmetric cyanine dyes, including ones that have a substituent ortho to the quinolinium or pyridinium nitrogen. Such a substituent, especially a cyclic substituent, ortho to the quinolinium or pyridinium nitrogen, is said to confer desired properties to the asymmetric cyanine dyes, according to U.S. Pat. No. 5,436,134. These cyclically substituted asymmetric cyanine dyes are commonly referred to as SYBR dyes. Zipper, et al., *Nucleic Acids Res.* 32(12), e103 (2004). Some of the reactive SYBR dyes are commercially available from Molecular Probes, Inc. (Eugene, Oreg.), although the exact structures of these dyes are not known. Haugland, R. P., *Handbook of Fluorescent Probes and Research Chemicals*, 9th edition.

U.S. Patent Application Publication No. 2004/0132046 discloses methods for preparing monomeric asymmetric cyanine dyes with minor groove-binding capability. In general, these dyes possess a crescent-shaped structure by virtue of having an additional benzazolyl substitutent on the benzazolyl ring of the dyes. Similar monomeric dyes having a suitable reactive group may be prepared using similar methods, for example, as schematically illustrated in Scheme 3 directly below.

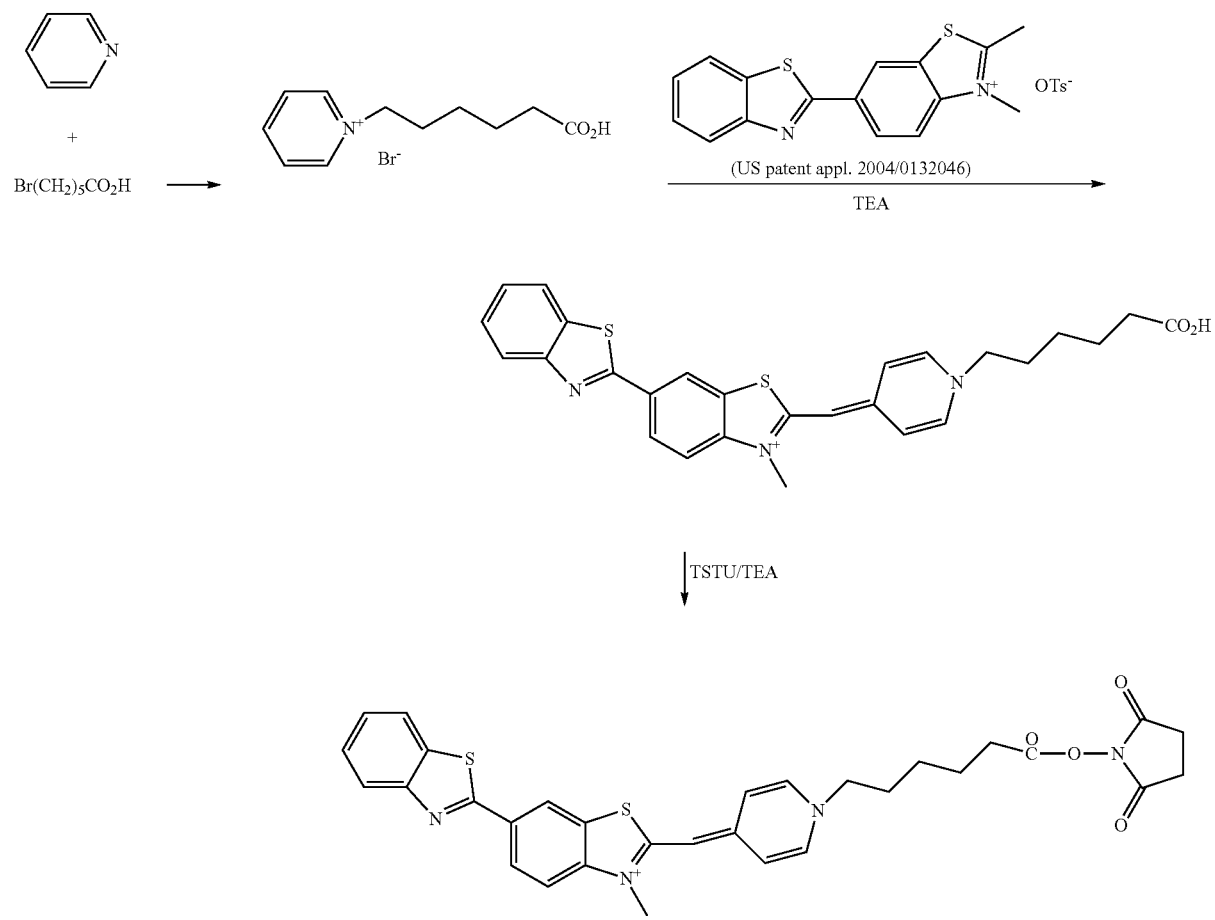

Reactive phenanthridinium dyes may be prepared from the commercially available 3,8-diamino-6-phenylphenanthridine, as schematically illustrated in Scheme 4 directly below.

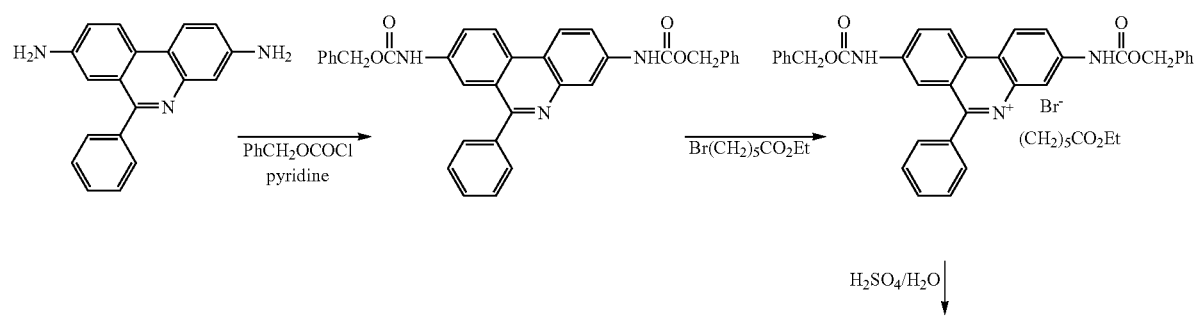

71 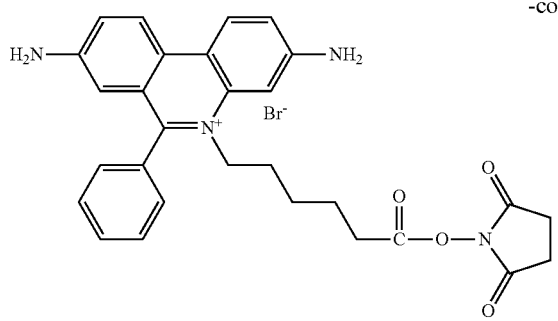 72 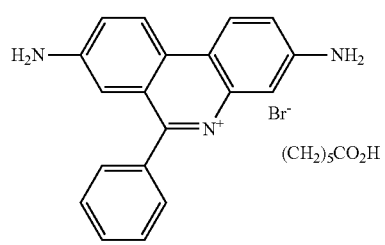

-continued

TSTU/TEA

Preparations of pyronin derivatives with a reactive group at the 9-position may be carried out by condensing two equivalents of m-aminophenol derivative with one equivalent of dicarboxylic anhydride, as schematically illustrated in Scheme 5 directly below.

significant portion of BRIDGE, such as up to about 90%, for example, may be pre-attached to the monomeric dyes prior to the final assembly of the dimeric dye. In some other cases, most of BRIDGE may be prepared separately before the monomeric dyes are attached. In the case of heterodimer Scheme 5

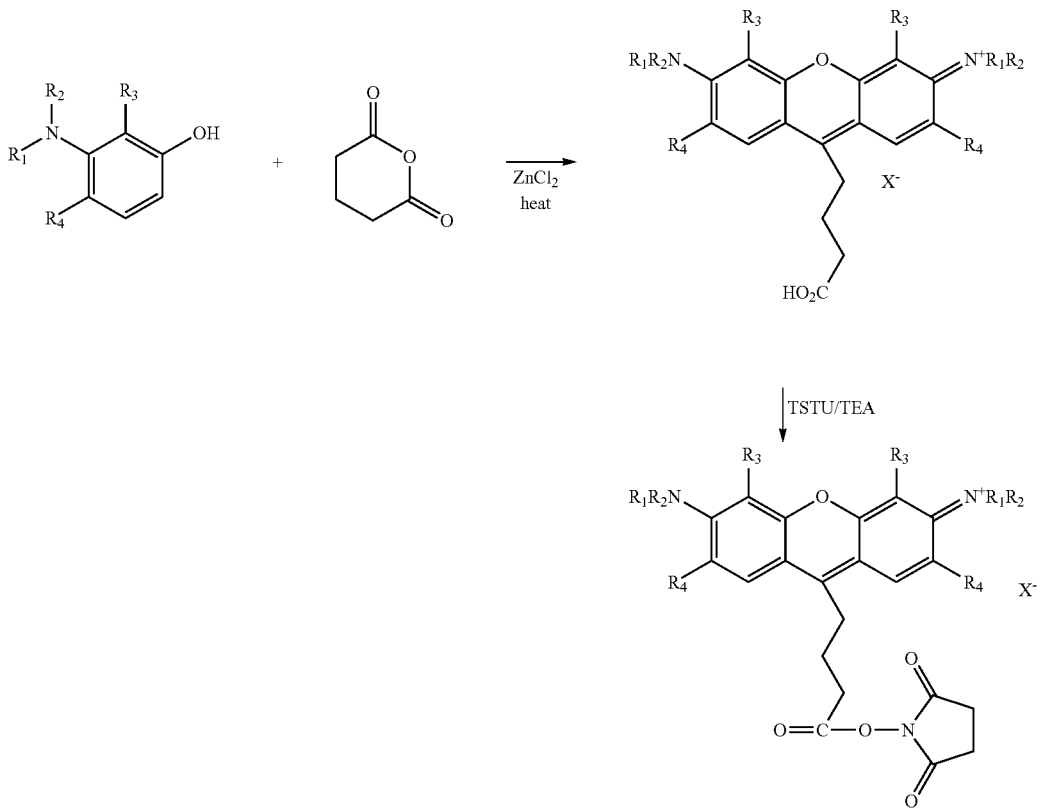

Many monomeric non-fluorescent nucleic acid-binding dyes are known pigments used in textile and ink industries and are commercially available. References for preparations of these dyes can be found in the literature. Many suitable reactive monomeric fluorescent non-nucleic acid dyes and non-fluorescent non-nucleic acid dyes are commercially available or may be prepared using known methods.

BRIDGE is usually formed when the monomeric dyes are coupled to a bi-functional group, which is often commercially available. In general, the terminal portions of BRIDGE are from the monomeric dyes themselves, while the middle portion of BRIDGE is from a bi-functional molecule available from a commercial source. In some cases, a portion or a synthesis, a mono-protected bi-functional linker group is usually first attached to one monomeric dye, followed by de-protection and coupling to the second monomeric dye.

In general, dimeric may be assembled by conjugating monomeric dyes having a suitable reactive group with a bi-functional linker in a one-step coupling reaction for some of the homodimers, or in multi-step reactions for heterodimers or some of the homodimers comprising multiple bridge element A. Examples of synthetic routes to selected homodimer and heterodimers are schematically illustrated in Scheme 6 directly below.

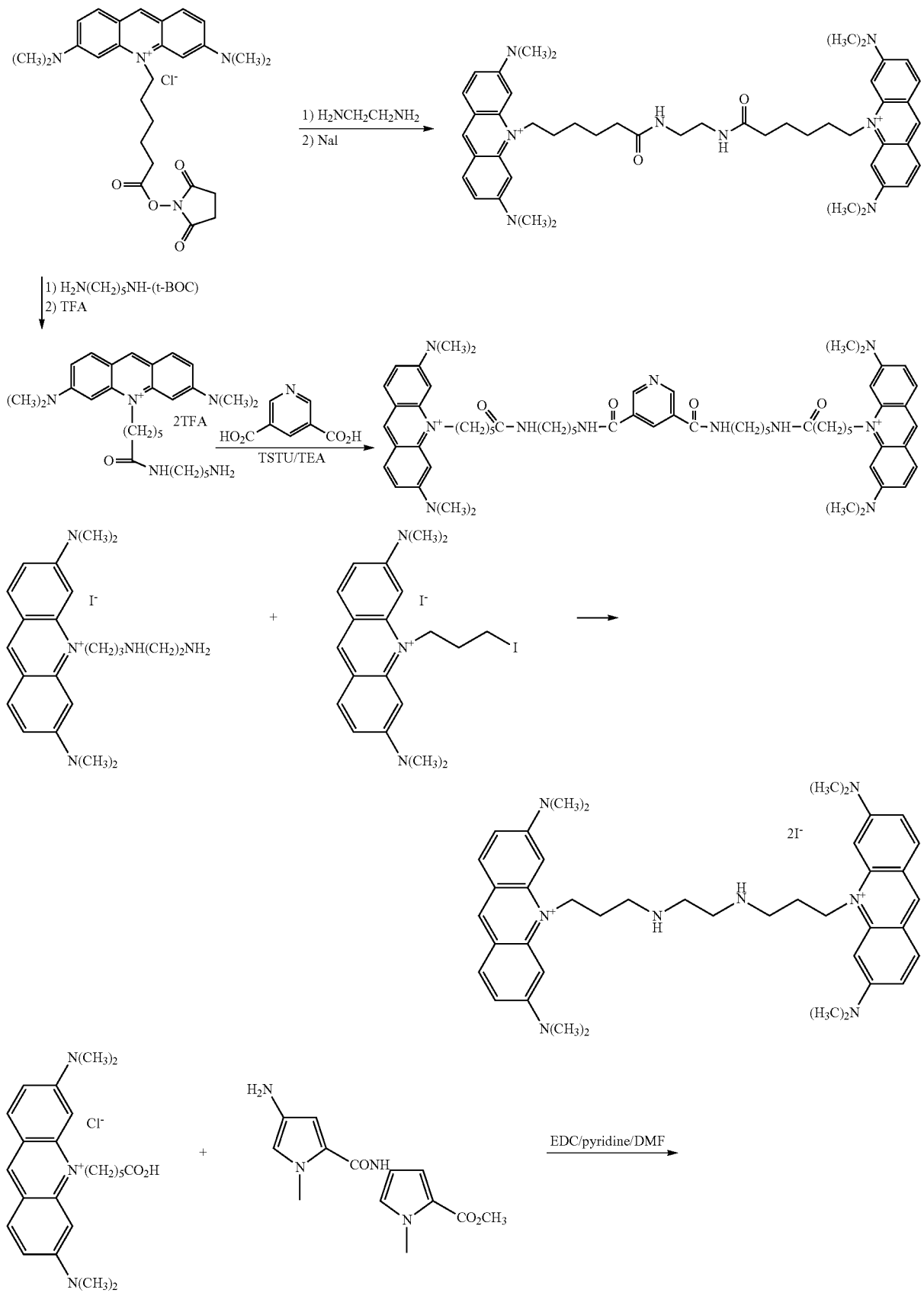

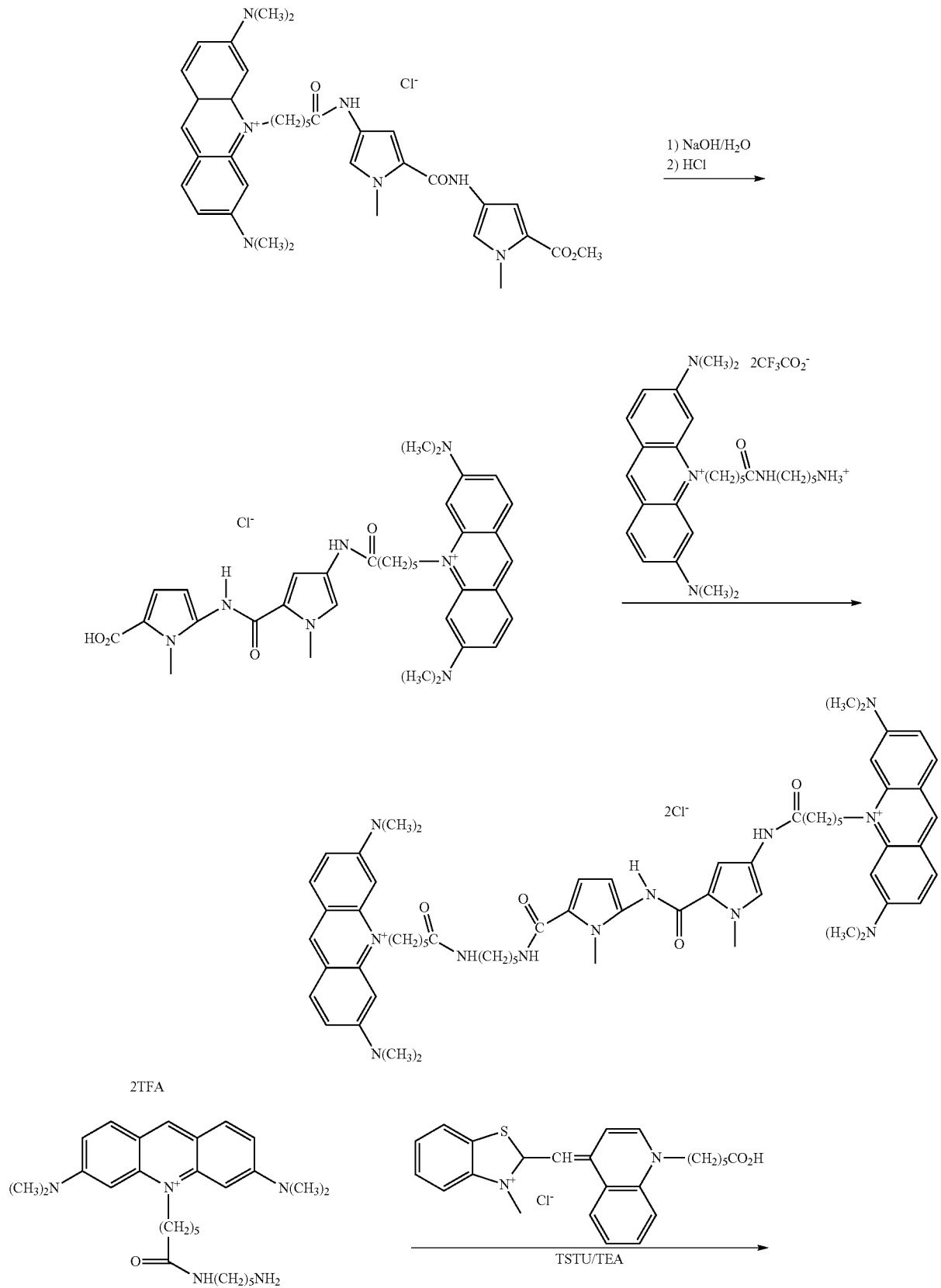

-continued

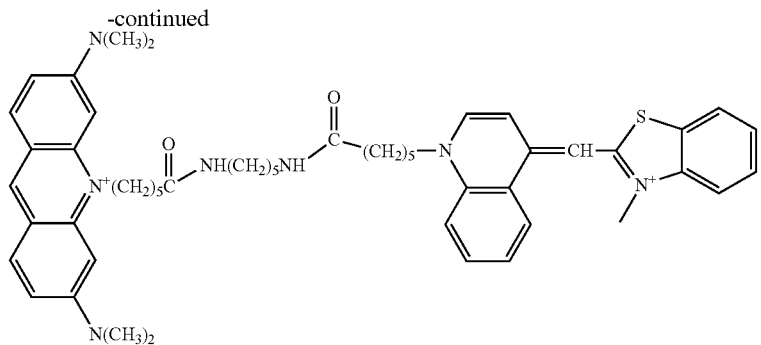

Examples

Example 1

Preparation of Dyes, Buffers, and Gels

Chemicals

Nucleic acid dyes (Compounds A, B, C, D, E, F, and G—Table 1) were prepared as described in U.S. Pat. No. 7,601,498. Agarose powders were from EMD Chemicals, Lonza, and National Diagnostics companies. All other chemicals were from Sigma-Aldrich.

Electrophoresis Buffers:

Tris-acetate-EDTA (TAE) buffer was made as a 10× stock (pH 8.18-8.29) using 48.4 g Tris-base, 10.9 g glacial acetic acid, 2.92 g ethylenediaminetetraacetic acid (EDTA) (free acid, F.W. 292.25) and 1.0 L distilled water.

Tris-borate-EDTA (TBE) buffer was made as a 5× stock (pH 8.13-8.23) using 54.0 g Tris-base, 27.5 g boric acid, 2.92 g EDTA (free acid, F.W. 292.25) and 1.0 L distilled water.

Sodium borate buffer was made as a 20× stock by adding 4.0 g sodium hydroxide and 23 g boric acid (F.W. 61.83) to 400 ml Type I water in a beaker with a magnetic stir bar. The mixture was stirred until the solids completely dissolved. pH was tested and additional boric acid was added until the pH reached 8.0. Volume was adjusted to 500 ml with Type I water and the solution was filter-sterilized with a 0.45 μm filter.

Lithium borate buffer was made as a 25× stock by adding 10.49 g lithium hydroxide monohydrate (F.W. 41.96) and ~54 g boric acid (F.W. 61.83) to 800 mL Type I water in a breaker with a magnetic stir bar. The mixture was stirred until the solids completely dissolved. PH was tested and additional boric acid was added until the pH reached 8.0. Volume was adjusted to 1 L with Type I water and the solution was filter sterilized with a 0.45 μm filter.

Two 6× loading buffers were prepared. Glycerol loading buffer comprised 30% glycerol in water, 0.125% bromophenol blue and 0.125% xylene cyanol. Ficoll-400 loading buffer comprised 15% Ficoll 400 in water, 0.1% Orange G and 0.1% Cresol red Gels:

Agarose gels were prepared by adding 0.42 g or 0.6 g agarose (for 0.7% or 1.0% gels, respectively) to 60 mL 1× running buffer. The mixture was heated until the agarose dissolved completely and the solution was cooled to about 50-60° C.

For post-staining methods, the agarose solution was poured into a gel tray, a comb was added and the solution was allowed to solidify at room temperature (RT) for about 45 minutes.

For in-gel staining methods, Compound A or C was added to the cooled agarose solution to a final concentration of 1 μM. A gel tray, a comb was added and the solution was allowed to solidify at room temperature (RT) for about 45 minutes. 6× loading buffer was premixed with DNA, and DNA samples were loaded onto the gel. The gel was run at 10 volt/cm (length between the electrodes) in 1× lithium borate buffer using the Owl EasyCast Minigel (gel size: 9×11 cm) horizontal electrophoresis system.

For the double-staining methods, Compound A was added to the cooled agarose solution to a final concentration of 1 μM. Pour into gel tray, add comb, and allow gel to solidify at room temperature for about 45 minutes. A gel tray, a comb was added and the solution was allowed to solidify at room temperature (RT) for about 45 minutes. DNA samples were premixed with 6× loading buffer with Compound A (1 μM). Samples were loaded onto the gel and run as above.

For the pre-staining methods, the cooled agarose solution was poured into a gel tray, a comb was added and the solution was allowed to solidify at room temperature (RT) for about 45 minutes. Premix DNA samples were premixed with 6× loading buffer containing Compounds A, D, and F. Samples were loaded onto the gel and run as above.

Example 2

Post-Gel Staining

A 1% agarose gel was prepared as described above for the post-staining method. 0.6 g OmniPur High Strength agarose (EMD Chemicals) was added to 60 ml 1×TBE buffer. DNA samples were loaded in the following order from left to right: (1) GeneRuler 1 kB ladder, (2) Invitrogen 1 kB ladder, (3) New England BioLabs Lambda DNA-HindIII Digest, (4) Promega Lambda DNA-HindIII Digest, (5) Bioline HyperLadder I, (6) Bioline HyperLadder IV, (7) Axygen M-DNA-LR, and (8) Axygen M-DNA-BR. Gel was run at 100 Volt for about two hours. No dye was added to the gel or DNA samples. Following electrophoresis, the gel was submerged in 1× TBE buffer containing Compound A (3 uM), and was agitated for 30 minutes at room temperature. The gel was visualized using the ethidium bromide emission filter on the UVP GelDoc-It Imaging System. Results are shown in FIG. 1.

Example 3

In-Gel Staining

Agarose gels (1%) were prepared as described above for the in-gel staining method using the AquaPorLE agarose from National Diagnostics. Gels were made using 1×TBE buffer, 1×TAE buffer, 1× lithium borate buffer. After cooling to about 50-60° C., Compound A (FIG. 2, panels A-C) or Compound C (FIG. 2, panel D) were added to the agarose solution to a final concentration of 1 um (about 6 ul). Gels were run in the corresponding 1× running buffer at 100 volt for about 2.5 hours.

Figure 2:
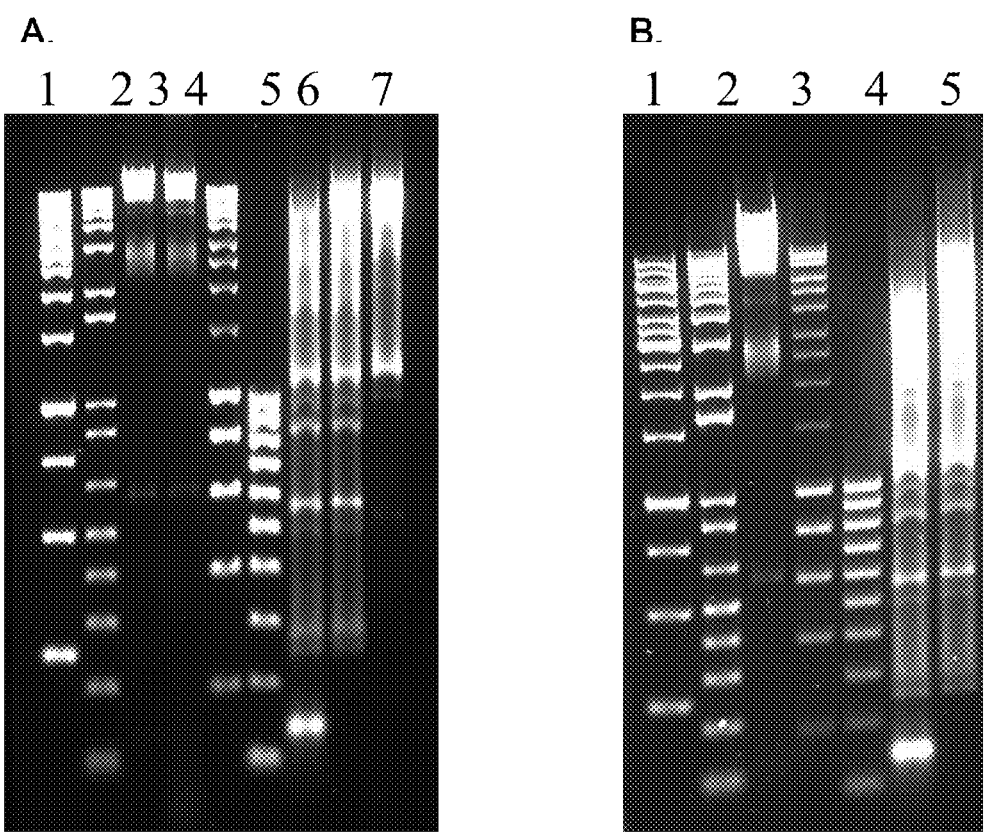
FIG. 2 (FIG. 2) illustrates in-gel staining with Compound B (1 uM) in 1×TBE, TAE and Lithium Borate running buffer and Compound C in 1× Lithium Borate buffer. Agarose gel (1%) was run in (A) 1×TBE running buffer, (B) 1×TAE running buffer, and (C and D) 1× Lithium Borate buffer. Samples in the lanes from left to right are as followed for (A), (C), and (D): (1) GeneRuler 1 kB ladder, (2) Invitrogen 1 kB ladder, (3) New England BioLabs Lambda DNA-HindIII digest, (4) Promega Lambda DNA-HindIII digest, (5) Bioline HyperLadder I, (6) Bioline HyperLadder IV, (7) Axygen M-DNA-LR, (8) Axygen M-DNA-BR, and (9) Axygen M-DNA-HR. The samples in the lanes from left to right for (B) are as followed: (1) GeneRuler 1 kB ladder, (2) Invitrogen 1 kB ladder, (3) New England BioLabs Lambda DNA-HindIII digest, (4) Bioline HyperLadder I, (5) Bioline HyperLadder IV, (6) Axygen M-DNA-LR, and (7) Axygen M-DNA-BR.
Figure 2:
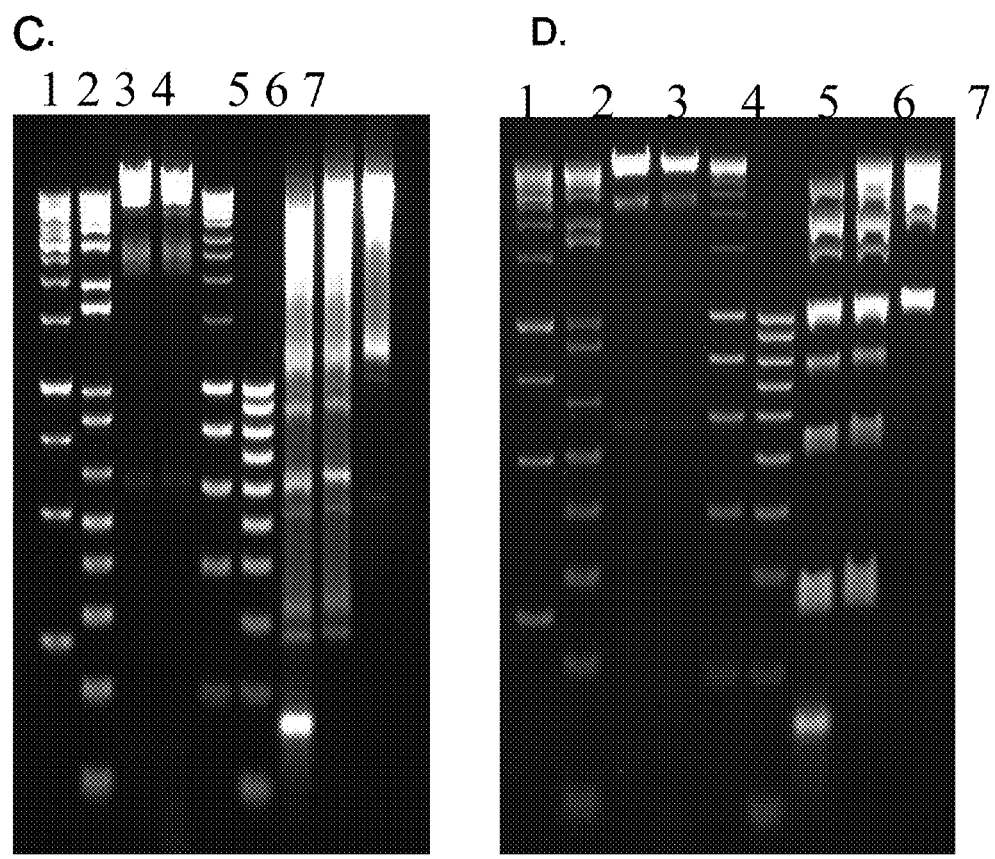

The following DNA markers were loaded onto the gel: GeneRuler 1 kB ladder (Fermentas), Invitrogen 1 kB ladder, New England Biolabs Lambda DNA-HindIII digest, Promega Lambda DNA-HindIII digest, Bioline HyperLadder I and IV, and Axygen M-DNA-LR and M-DNA-BR. Gels were visualized on the UVP GelDoc-It Imaging System using the ethidium bromide emission filter. Results are shown in FIG. 2.

In-gel staining, where the nucleic acid dye is pre-embedded in the gel matrix, is typically preferred over post-staining methods because there is less chance of exposure to potentially harmful dyes and typically requires less of the dye. Nucleic acid staining by the dye takes place as the nucleic acids migrate during electrophoresis. The staining can be viewed either during or following the electrophoresis. However, in-gel staining with dimeric dyes, such as dimeric phenanthridinium dyes when using conventional buffer systems, can be unreliable because the dyes may interfere with nucleic acid migration to an extent that may result in unacceptable band resolution. FIG. 2 (panels A-C) shows results from in-gel staining of various DNA ladders using compound A in three different gel electrophoresis buffers. 2 or 3 of the ladders have reasonably good resolution while the remaining ladders are poorly resolved. In particular, the ladders in the last three lanes on the right in Panels A and C and the last two ladders on the right in Panel B are poorly resolved. Without being bound by theory, it is possible that different procedures and sources of DNA are used for the manufacturing of these DNA ladders by the various vendors. Thus, the widely differing resolutions among the various ladders suggest that effects of the dye on nucleic acid migration is dependent on the nature of the nucleic acid samples (e.g., the relative richness of AT or GC content or the particular way the nucleic acid fragments are produced by a particular restriction enzyme). Blurred band resolution—such as those in FIGS. 2A, 2B and 2C—can also be due to a degraded or a very complex nucleic acid sample. Thus, poor band resolution caused by dye interference can complicate interpretation of results which include blurred band resolution. Thus, if one is to rely on an in-gel nucleic acid staining result, it is desirable for one to use a staining condition where the effect of the dye on nucleic acid migration is minimally dependent on the nature of the nucleic acid sample.

Example 3

Double Staining

Figure 3:
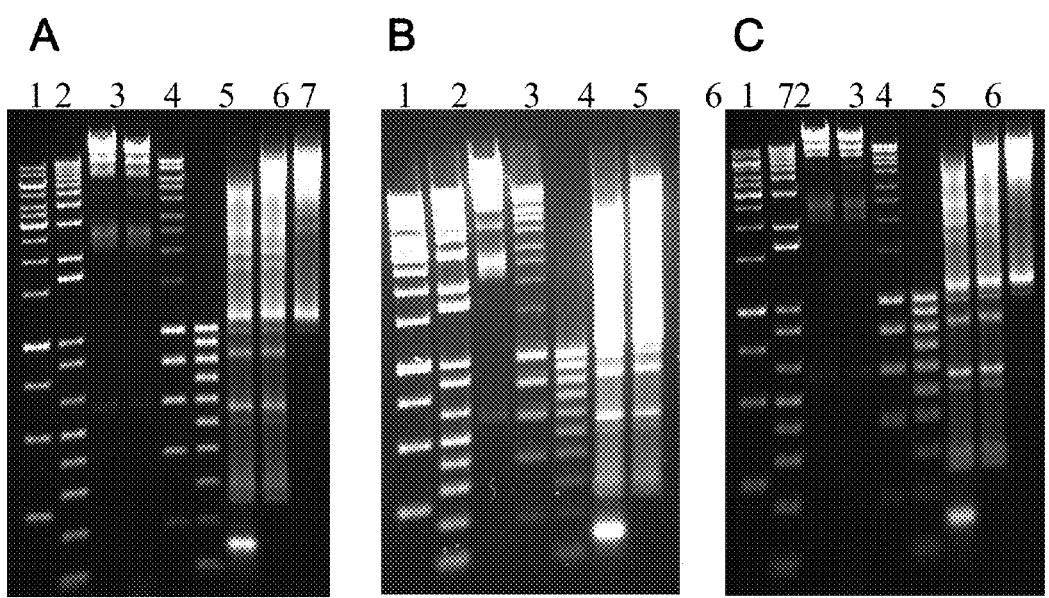
FIG. 3 (FIG. 3) illustrates double staining with Compound A (Table 1). 0.7% Agarose gels were run in (A) 1×TBE, (B) 1×TAE, and (C) 1× lithium borate buffer. Each DNA sample contains 1 uM Compound A pre-mixed before loading onto the gel, and the dye was added to the gel to a 1 uM concentration. The samples in the lanes for (A) and (C) are as followed (from left to right): (1) GeneRuler 1 kB ladder, (2) Invitrogen 1 kB ladder, (3) New England BioLabs Lambda DNA-HindIII digest, (4) Promega Lambda DNA-HindIII digest, (5) Bioline HyperLadder I, (6) Bioline HyperLadder IV, (7) Axygen M-DNA-LR, (8) Axygen M-DNA-BR, and (9) Axygen M-DNA-HR. The samples in the lanes for (B) are as followed: (1) GeneRuler 1 kB ladder, (2) Invitrogen 1 kB ladder, (3) New England BioLabs Lambda DNA-HindIII digest, (4) Bioline Hyperladder I, (5) Bioline HyperLadder IV, (6) Axygen M-DNA-LR, and (7) Axygen M-DNA-BR.

A variation of the in-gel staining method is the "double staining method," where in addition to pre-embedding a nucleic acid dye in the gel matrix the nucleic acid dye is also pre-combined with a nucleic acid sample when the sample is loaded into the gel for electrophoresis. As shown in FIG. 3, this method failed to improve the separation resolution for all ladders. While some of the DNA ladders showed slightly improved resolution, other DNA ladders had even worse separation compared to the results using the in-gel staining method (FIG. 2). The worst results were from the double staining using TAE buffer (FIG. 3B), which is the most widely used gel electrophoresis buffer.

0.7% agarose gels were prepared as described above for the double-staining method. 0.42 g agarose powder was added to 60 ml 1×TBE (FIG. 3, panel A), 1×TAE (FIG. 3, panel B), and 1× lithium borate buffer (FIG. 3, panel C). Before agarose was poured into gel tray, 6 ul Compound A was added to the agarose. The final concentration of Compound A in the gel is 1 µM. DNA markers were premixed with Compound A and a 6× loading buffer as follow: 10 ul DNA plus 2 µl 6× loading buffer containing Compound A. The final concentration of Compound A in each DNA sample is 1 µM.

The following DNA markers were loaded onto the gel: GeneRuler 1 kB ladder (Fermentas), Invitrogen 1 kB ladder, New England Biolabs Lambda DNA-HindIII digest, Promega Lambda DNA-HindIII digest, Bioline HyperLadder I and IV, and Axygen M-DNA-LR and M-DNA-BR. Gels were run at 100 volt for about 2.5 hours. Gels were visualized on the UVP GelDoc-It Imaging System using the ethidium bromide emission filter. Results are shown in FIG. 3.

Example 4

Prestaining

An appealing nucleic acid gel staining method is the pre-staining method, where the nucleic acid binding dye is pre-combined with a nucleic acid sample in a loading buffer and the resulting buffer comprising the nucleic acid-dye complex(s) is loaded into the gel followed by electrophoresis. Unlike the double-staining or in-gel staining methods, this method does not require the nucleic acid binding dye pre-embedded in the gel matrix. This method has the advantage of the in-gel staining or double-staining methods in that visualization can be carried out while the gel is running or after the electrophoresis has been finished. Another advantage of pre-staining is that a gel may be re-used if not all of the wells have been used in a previous running. This offers flexibility and cost saving. Furthermore, for any given nucleic acid binding dye, pre-staining is the safest staining method due to the relatively small amount of the dye used. With these advantages, pre-staining would be the obvious method of choice for gel staining.

Figure 4:
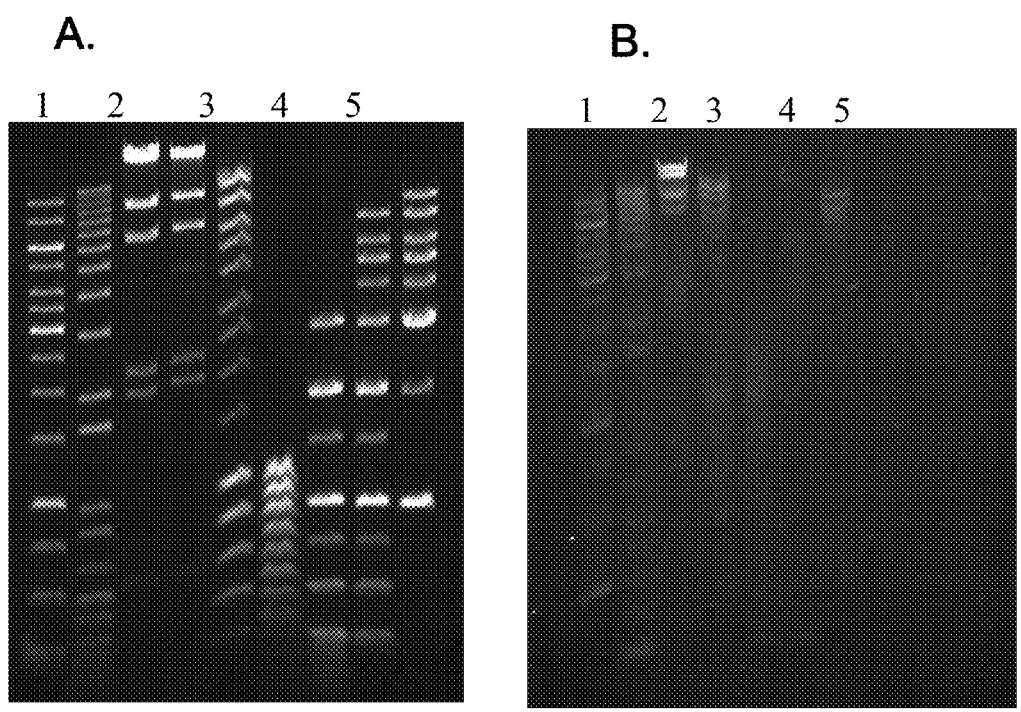
FIG. 4 (FIG. 4) illustrates pre-staining with Compound A (Table 1) in TAE or TBE. 1% Agarose gels were run in (A) 1×TBE and (B) 1×TAE running buffers. No dye was added to the gel. Compound A was added to each DNA sample to a final concentration of 1 uM. The lanes in (A) are as followed (from left to right): (1) GeneRuler 1 kB ladder, (2) Invitrogen 1 kB ladder, (3) New England BioLabs DNA-HindIII digest, (4) Promega Lambda DNA-HindIII digest, (5) Bioline HyperLadder I, (6) Bioline HyperLadder IV, (7) Axygen M-DNA-LR, (8) Axygen M-DNA-BR, and (9) Axygen M-DNA-HR. The samples in (B) are as followed: (1) GeneRuler 1 kB ladder, (2) Invitrogen 1 kB ladder, (3) New England BioLabs Lambda DNA-HindIII digest, (4) Bioline HyperLadder I, (5) Bioline HyperLadder IV, (6) Axygen M-DNA-LR, and (7) Axygen M-DNA-BR.
Figure 5:
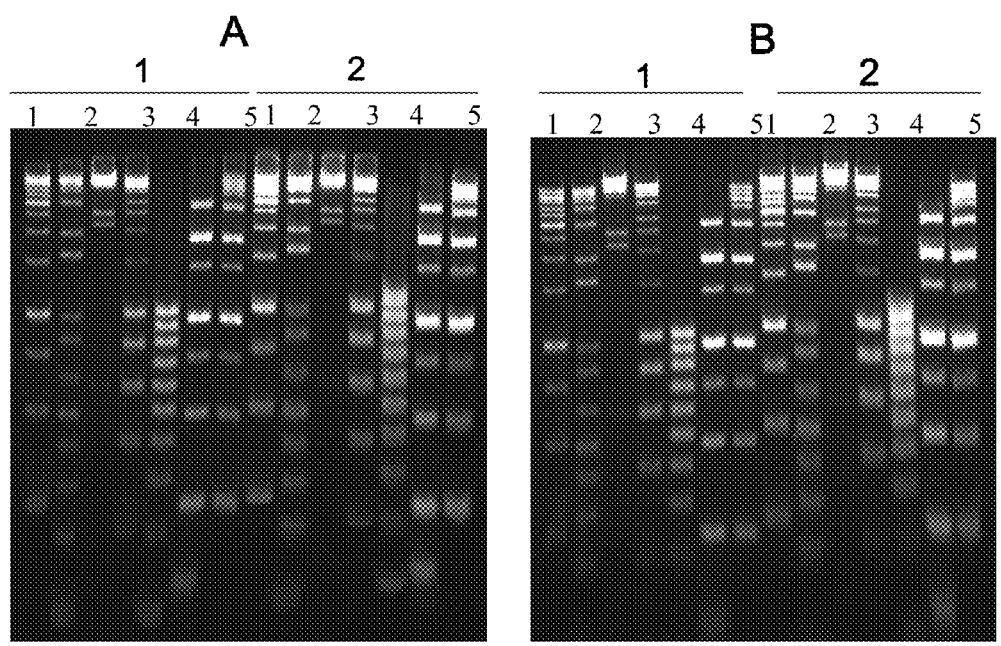
FIG. 5 (FIG. 5) illustrates pre-staining with Compound A (Table 1) in Sodium Borate. Two different types of agarose gels were used to test pre-staining in sodium borate running buffer. 1% AquaPorLE (National Diagnostics) (A) and 1%

However, most nucleic acid dyes simply do not work well for this method under conventional buffer conditions, either because the dyes severely affect nucleic acid migration or because the nucleic acid binding affinities of the dyes are too weak for sensitive detection. Most nucleic acid dyes, due to their positive charge and small size relative to the nucleic acids, rapidly migrate toward the negative end of the electric field during electrophoresis, potentially leaving nucleic acid bands at the positive end of the electric field unstained. High affinity dimeric dyes having a highly positively charged bridge moiety (such as the TOTO and YOYO dyes) have been previously used in pre-staining. However, staining with these high affinity dyes are usually not compatible with downstream product manipulation because the dyes are difficult to remove. Likewise, dimeric phenanthridinium dyes, such as the commercial dye GelRed (U.S. Pat. No. 7,601,498), have generally not been ideal for the pre-staining method because of poor band resolution, band distortion or low sensitivity. FIGS. 4A and 4B show the pre-staining results of several DNA ladders using Compound A in two electrophoresis buffers, TBE and TAE, respectively. In TBE buffer, a few of the ladders showed good resolution and sensitivity. However, some of the ladders (i.e., columns 5, 6, and 9 from left to right) showed distorted bands. Again, since the band distortion could be contributed by factors other than the dye, this staining condition is not sufficiently reliable. The pre-staining carried out in TAE buffer (FIG. 4B) produced very weak and smeared bands and therefore is also not a suitable method. Prestaining in sodium borate buffer produced similarly diffused bands (FIG. 5).

Agarose gels (1%) were prepared as described above for the pre-staining method using agarose powder from National Diagnostics (AquaPor LE and AquaPor 3:1), Lonza (Seakem LE), and EMD Chemicals (OmniPur High Strength). 0.6 g agarose powder was added to 60 ml 1×TAE buffer (FIG. 4), 1×TBE (FIG. 4), 1× sodium borate (FIG. 5), and 1× lithium borate buffer (FIGS. 6, 7, 8). No dye was added to the gels. Gels were run at 100 volts for about 2.5 hours in the corresponding 1× buffer.

The following DNA markers were loaded onto the gel: GeneRuler 1 kB ladder (Fermentas), Invitrogen 1 kB ladder, New England Biolabs Lambda DNA-HindIII digest, Promega Lambda DNA-HindIII digest, Bioline HyperLadder I and IV, and Axygen M-DNA-LR and M-DNA-BR.

Compound A and Compound F were added to separate tubes of 6× loading buffer to a concentration of 6 µM. DNA markers were premixed with either Compound A or F in a 6× loading buffer as follow: 10 µl DNA plus 2 µl 6× loading buffer containing Compound A. A total volume of 12 µl was loaded into each well of the gel. For FIGS. 4, 5, 6, 7, and 8, the final concentration of Compound A or F in each DNA sample is 1 µM.

Compound D was premixed with DNA markers and 6× loading buffer as described for Compounds A and F. The final concentration of Compound D in each DNA sample in FIG. 7 is 5 µM. Following electrophoresis, gels were visualized on the UVP GelDoc-It Imaging System. Results are shown in FIGS. 4-8.

Example 5

Prestaining in Absence of Gel Buffer Containing Lithium Salt

For this experiment, DNA samples were electrophoresed in a pre-cast gel using a different gel buffer than running buffer. A 4-20% TBE precast polyacrylamide gel was loaded with different concentration of the Fermentas GeneRuler Ultra Low Range DNA ladder. The gel was run in a Bio-Rad protean minigel system for one hour at 100 V. DNA samples were prestained with Compound A, Compound D or Compound F as described above. DNA samples loaded are as follow (from left to right): (1) 31.25 ng, (2) 62.5 ng, (3) 125 ng, (4) 250 ng, (5) 500 ng of the GeneRuler Ultra Low Range DNA ladder. The gels were photographed using the UVP GelDoc-It Imagining System using the (a) ethidium bromide and (b) SYBR Green emission filter settings. Results are shown in FIG. 9.

The results show that, although the running buffer contains lithium borate, the gel buffer (i.e., buffer in the gel) is not required to contain a lithium salt of a weak acid in order to produce clear results of DNA separation. In this example, the gel buffer used is Tris borate. The results indicate that any borate-containing buffer (e.g., lithium borate, tris borate, sodium borate, cesium borate, potassium borate, etc.) can be utilized. Thus, the methods for prestaining described herein can be utilized where the gel buffer and running buffer are different.

The present disclosure provides pre-staining methods that produce well resolved bands and sensitive and minimally affected by the nature of nucleic acid samples. Prestaining using methods disclosed herein produces sharp and well-resolved nucleic acid bands with excellent sensitivity. Most importantly, the separation and staining results are not dependent on the nature of the nucleic acid samples (FIGS. 6, 7 and 8). Additionally, the method is safe because only a minimal amount of a cell membrane-impermeable nucleic acid dye is used.

Various modifications, processes, as well as numerous structures relating to the description herein may be applicable, as will be readily apparent to those of ordinary skill in the art, upon review of the specification. Various references, publications, provisional and non-provisional United States or foreign patent applications, and/or United States or foreign patents, have been identified herein, each of which is incorporated herein in its entirety by this reference. Various aspects and features may have been explained or described in relation to understandings, beliefs, theories, underlying assumptions, and/or working or prophetic examples, although it will be understood that any such understanding, belief, theory, underlying assumption, and/or working or prophetic example is not binding. Although the various aspects and features have been described with respect to various embodiments and examples herein, it will be understood that any of same is not limiting with respect to the full scope of the appended claims.

The invention claimed is:

1. A method of detecting the presence or absence of a nucleic acid in a sample, comprising:

combining a sample comprising a nucleic acid with at least one fluorescent nucleic acid binding dye having the formula:

wherein BRIDGE is a substantially neutral covalent linker comprising from about 1 to about 150 non-hydrogen atoms;

$Q_1$ is a phenanthridinium dye, an acridinium dye or an asymmetric cyanine dye;

$Q_2$ is a phenanthridinium dye, an acridinium dye or an asymmetric cyanine dye;

loading said sample into a gel, wherein said gel comprising a gel buffer;

immersing said gel in a running buffer;

wherein said gel buffer or running buffer comprises at least one weak acid and a lithium salt of said at least one weak acid;

electrophoresing said sample; and detecting fluorescence associated with the sample or a lack thereof.

2. The method of claim 1, wherein said running buffer comprises at least one weak acid and a lithium salt of said at least one weak acid.

3. The method of claim 1, wherein said sample further comprises a loading dye.

4. The method of claim 3, wherein said loading dye is xylene cyanol, cresol red, bromophenol blue, orange G or tartrazine.

5. The method of claim 1, wherein $Q_1$ and $Q_2$ are different.

6. The method of claim 1, wherein when $Q_1$ and/or $Q_2$ is a phenanthridinium dye it has the structure of Formula I or Formula II:

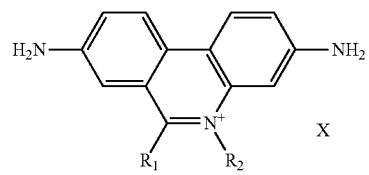

Formula I

-continued

Formula II

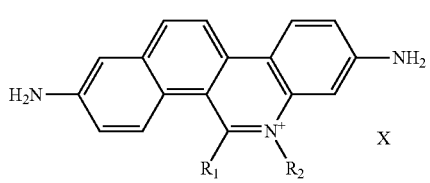

wherein $R_1$ is an aryl, a heteroaryl, an alkyl, H, -BRIDGE-$Q_1$ or -BRIDGE-$Q_2$; $R_2$ is an alkyl, -BRIDGE-$Q_1$ or -BRIDGE-$Q_2$; X is a counter ion and wherein only one of $R_1$ and $R_2$ is -BRIDGE-$Q_1$ or -BRIDGE-$Q_2$.

7. The method of claim 6, wherein said phenanthridinium dye has the structure of Formula I, $R_1$ is a phenyl and $R_2$ is -BRIDGE-$Q_1$ or -BRIDGE-$Q_2$.

8. The method of claim 7, wherein both $Q_1$ and $Q_2$ are the same phenanthridinium dye.

9. The method of claim 6, wherein said phenanthridinium dye has the structure of Formula I, $R_2$ is a phenyl and $R_1$ is -BRIDGE-$Q_1$ or -BRIDGE-$Q_2$.

10. The method of claim 9, wherein both $Q_1$ and $Q_2$ are the same phenanthridinium dye.

11. The method of claim 1, wherein when $Q_1$ and/or $Q_2$ is a acridinium dye it has the structure of Formula III:

Formula III

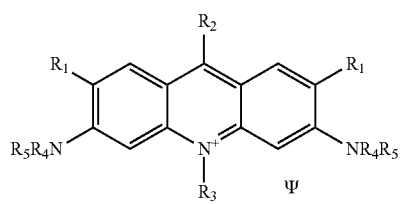

wherein each $R_1$, may be the same or different and is H, or a C1-C2 alkyl; $R_2$ is an H, a C1-C6 alkyl, a C1-C2 perfluoroalkyl, an aryl, an heteroaryl, —$NH_2$, —$NHCH_3$, —CN, —C(=O)$NH_2$, -BRIDGE-$Q_1$ or -BRIDGE-$Q_2$; $R_3$ is an H, a C1-C2 alkyl, -BRIDGE-$Q_1$ and -BRIDGE-$Q_2$; $R_4$ and $R_5$, may be the same or different and is an H, or a C1-C2 alkyl; and Ψ is a counter ion; and only one of $R_2$ and $R_3$ is -BRIDGE-$Q_1$ or -BRIDGE-$Q_2$.

12. The method of claim 11, wherein $R_1$ and $R_2$ are H; $R_3$ is -BRIDGE-$Q_1$ or -BRIDGE-$Q_2$; and $R_4$ and $R_5$ are —$CH_3$.

13. The method of claim 12, wherein both $Q_1$ and $Q_2$ are the same acridinium dye.

14. The method of claim 1, wherein when $Q_1$ and/or $Q_2$ is a asymmetric cyanine dye it has the structure of Formula IV:

Formula IV

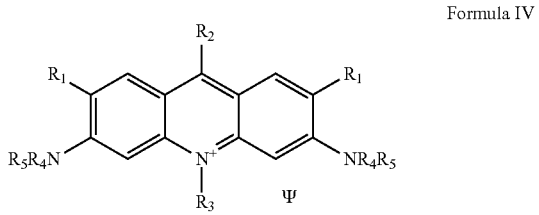

wherein $R_1$ is a substituted or unsubstituted C1-C6 alkyl; $R_2$ is H, halogen or a substituted or unsubstituted aryl; n is 0, 1 or 2; $R_3$ is an H, a substituted or unsubstituted alkyl, a substituted or unsubstituted alkylamino, a substituted or unsubstituted dialkylamino, dialkylamino, a substituted or unsubstituted aryl, a substituted or unsubstituted heterocycle, -BRIDGE-$Q_1$ or -BRIDGE-$Q_2$; $R_4$ is a substituted or unsubstituted C1-C6 alkyl, a substituted or unsubstituted aryl, -BRIDGE-$Q_1$ and -BRIDGE-$Q_2$; $R_5$ and $R_6$ may be the same or different and are H, or —$CH_3$ or $R_5$ and $R_6$ in combination with the carbon atoms they are attached to form a fused benzene ring; Ψ is a counter ion; and only one of $R_3$ and $R_4$ is -BRIDGE-$Q_1$ or -BRIDGE-$Q_2$.

15. The method of claim 14, wherein $R_1$ is —$CH_3$; $R_2$ is H; n is 0; $R_3$ is H; $R_4$ is -BRIDGE-$Q_1$ or -BRIDGE-$Q_2$; and $R_5$ and $R_6$ together with the carbon atoms they are attached to form a fused benzene ring.

16. The method of claim 15, wherein both $Q_1$ and $Q_2$ are the same asymmetric cyanine dye.

17. The method of claim 1, wherein said weak acid has a $pK_a$ of about 8.0 to about 10.5.

18. The method of claim 1, wherein said weak acid is boric acid.

19. The method of claim 1, wherein the gel buffer or running buffer has a pH of about 7.7 to about 9.0.

20. The method of claim 19, wherein the gel buffer or running buffer has a pH of about 8 to about 8.8.

21. The method of claim 1, wherein said gel buffer or running buffer comprises from about 0.5 mM to about 30 mM $Li^+$.

22. The method of claim 1, wherein said gel buffer or running buffer further comprises one or more of a magnesium chelator, a detergent, or a preservative.

23. The method of claim 1, wherein said fluorescent nucleic acid binding dye has the structure:

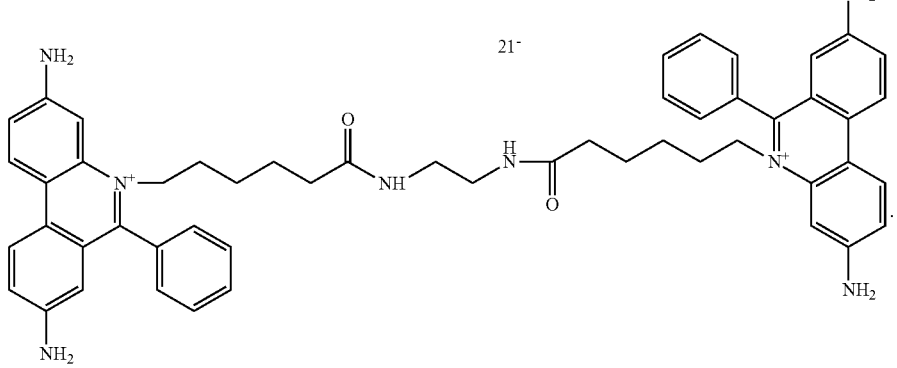

24. The method of claim 1, wherein said fluorescent nucleic acid binding dye has the structure:
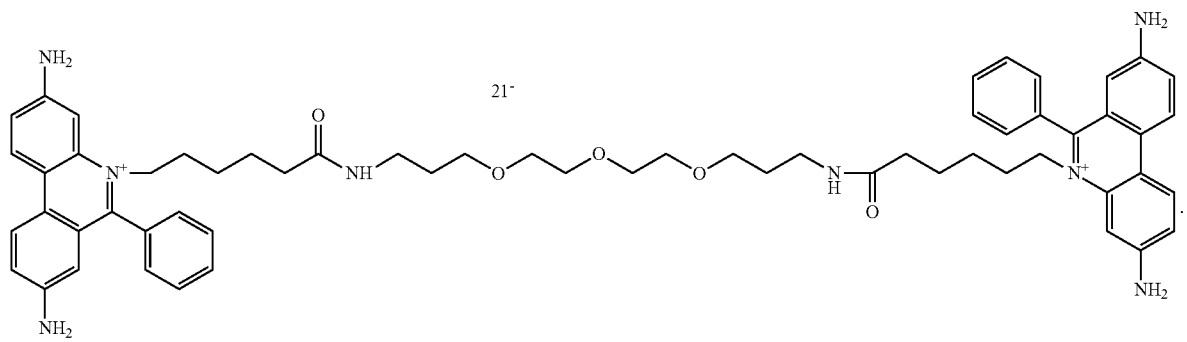 [SMILES: Nc1ccc2c(c1)c(-c1ccccc1)[n+](CCCCCC(=O)NCCCOCCOCCOCCCNC(=O)CCCCC[n+]1c(-c3ccccc3)c3cc(N)ccc3c3ccc(N)cc31)c1cc(N)ccc21]
25. The method of claim 1, wherein said fluorescent nucleic acid binding dye has the structure:
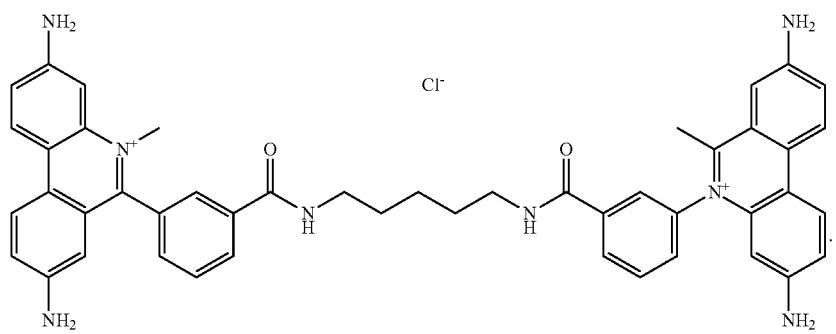 [SMILES: Cc1c2cc(N)ccc2c2ccc(N)cc2[n+]1-c1cccc(C(=O)NCCCCCNC(=O)c2cccc(-c3c4cc(N)ccc4c4ccc(N)cc4[n+]3C)c2)c1 ; [Cl-]]
35
26. The method of claim 1, wherein said fluorescent nucleic acid binding dye has the structure:
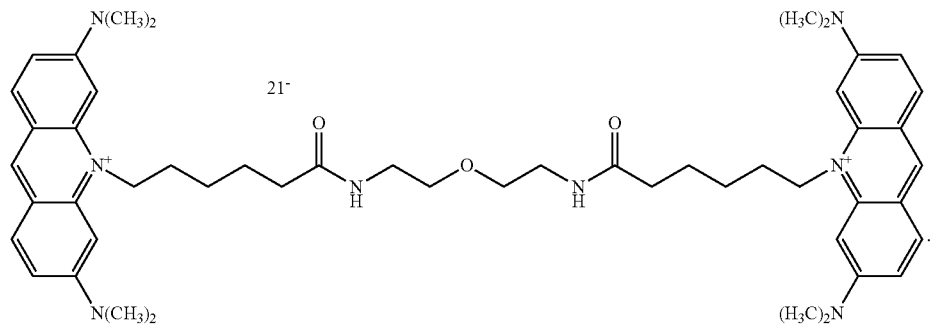
27. The method of claim 1, wherein said fluorescent nucleic acid binding dye has the structure:
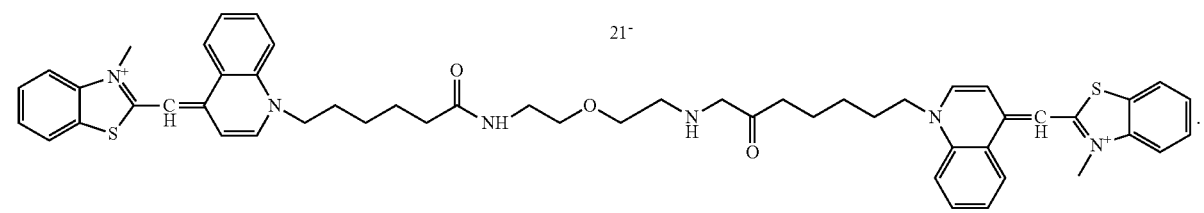 [SMILES: C[n+]1c(C=C2C=CN(CCCCCC(=O)CNCCOCCNC(=O)CCCCCN3C=CC(=Cc4sc5ccccc5[n+]4C)c4ccccc43)c3ccccc32)sc2ccccc21]

28. The method of claim 1, wherein said fluorescent nucleic acid binding dye has the structure:
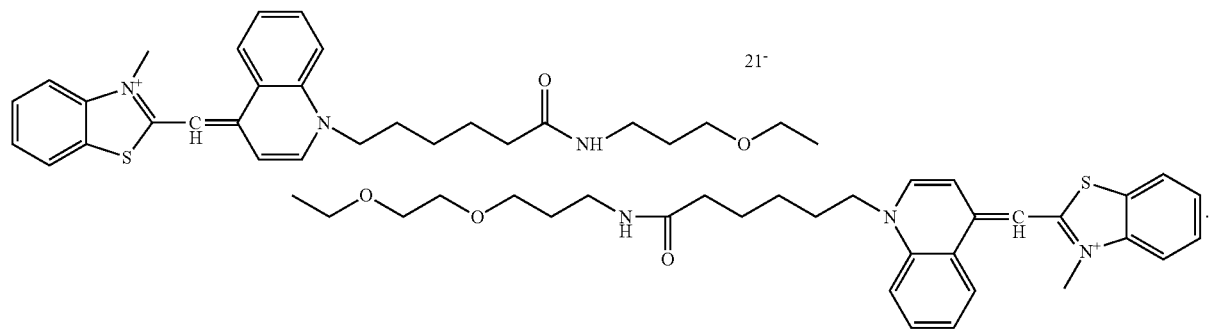
29. The method of claim 1, wherein said fluorescent nucleic acid binding dye has the structure:
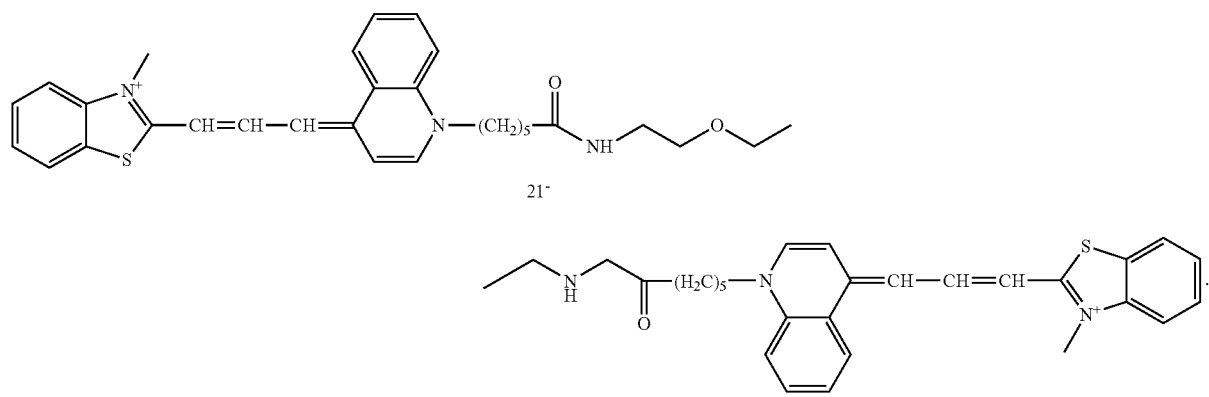
* * * * *